United States Patent [19]

Norbeck et al.

[11] Patent Number: 5,246,931
[45] Date of Patent: Sep. 21, 1993

[54] CARBOCYCLIC NUCLEOSIDE ANALOGS

[75] Inventors: Daniel W. Norbeck, Lindenhurst; Jacob J. Plattner, Libertyville, both of Ill.; Terry J. Rosen, East Lyme, Conn.; David L. Garmaise, Kenosha, Wis.

[73] Assignee: Bristol-Myers Squibb Company, Princeton, N.J.

[21] Appl. No.: 694,538

[22] Filed: May 1, 1991

Related U.S. Application Data

[60] Division of Ser. No. 420,691, Oct. 17, 1989, which is a continuation of Ser. No. 319,385, Mar. 3, 1989, abandoned, which is a continuation of Ser. No. 262,547, Oct. 25, 1988, abandoned.

[51] Int. Cl.$^5$ .................... A61K 31/53; C07D 253/00; C07D 251/00
[52] U.S. Cl. ........................... 514/242; 514/84; 514/241; 514/245; 514/258; 514/262; 514/269; 514/272; 514/274; 514/303; 514/348; 544/182; 544/194; 544/195; 544/211; 544/262; 544/264; 544/280; 544/220; 544/310; 544/311; 544/312; 544/313; 544/314; 544/316; 544/317; 544/318; 544/254; 546/118; 546/296
[58] Field of Search ............... 544/182, 211, 194, 195, 544/214, 223; 514/242, 245, 84, 241

[56] References Cited

U.S. PATENT DOCUMENTS

| | | | |
|---|---|---|---|
| 3,923,792 | 12/1975 | Albrecht et al. | 544/314 |
| 4,016,267 | 4/1977 | Albrecht et al. | 544/276 |
| 4,508,898 | 4/1985 | Ogilvie | 544/211 |

(List continued on next page.)

FOREIGN PATENT DOCUMENTS

| | | |
|---|---|---|
| 49072 | 7/1982 | European Pat. Off. . |
| 0184473 | 6/1986 | European Pat. Off. . |
| 0322854 | 7/1989 | European Pat. Off. . |
| 0330992 | 9/1989 | European Pat. Off. . |
| 0335355 | 10/1989 | European Pat. Off. . |
| 519898 | 3/1984 | Spain . |

OTHER PUBLICATIONS

Kim et al., "Potential Anti-AIDS Drugs", J. Med. Chem., 1987, 30, 862–866.

(List continued on next page.)

*Primary Examiner*—Cecilia Tsang
*Attorney, Agent, or Firm*—Stephen B. Davis

[57] ABSTRACT

A compound of the formula:

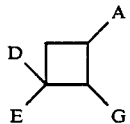

wherein A is a purin-9-yl group, a heterocyclic isostere of a purin-9-yl group, a pyrimidin-1-yl group or a heterocyclic isostere of a pyrimidin-1-yl group; E is hydrogen, —$CH_2OH$ or —OH; and G and D are independently selected from hydrogen, $C_1$ to $C_{10}$ alkyl, —OH, —$CH_2OH$, —$CH_2OR_{20}$ wherein $R_{20}$ is $C_1$ to $C_6$ alkyl, —$CH_2OC(O)R_{21}$ wherein $R_{21}$ is $C_1$ to $C_{10}$ alkyl, —$CH_2OC(O)CH(R_{22})(NHR_{23})$ wherein $R_{22}$ is the side chain of any of the naturally occurring amino acids and $R_{23}$ is hydrogen or —$C(O)CH(R_{24})(NH_2)$ wherein a $R_{24}$ is the side chain of any of the naturally occurring amino acids, —$CH_2SH$, —$CH_2Cl$, —$CH_2F$, —$CH_2Br$, —$CH_2I$, —$C(O)H$, —$CH_2CN$, —$CH_2N_3$, —$CH_2NR_1R_2$, —$CO_2R_1$, —$CH_2CH_2OH$, —$CH_2CH_2OR_{20}$ wherein $R_{20}$ is as defined above, —$CH_2CH_2OC(O)R_{21}$ wherein $R_{21}$ is as defined above, —$CH_2CH_2OC(O)CH(R_{22})(NHR_{23})$ wherein $R_{22}$ and $R_{23}$ are as defined above, —$CH_2CH_2PO_3H_2$, —$CH_2OPO_3H_2$, —$OCH_2PO_3H_2$ and —$CH_2CO_2R_3$ wherein $R_1$ and $R_2$ are independently selected from hydrogen and $C_1$ to $C_{10}$ alkyl and $R_3$ is hydrogen, $C_1$ to $C_{10}$ alkyl, carboxyalkyl or aminoalkyl; or a pharmaceutically acceptable salt thereof.

6 Claims, No Drawings

U.S. PATENT DOCUMENTS

| | | | |
|---|---|---|---|
| 4,617,304 | 10/1986 | Ashton et al. | 544/276 |
| 4,644,001 | 2/1987 | Kjellin et al. | 544/276 |
| 4,782,062 | 11/1988 | Tolman et al. | 544/314 |
| 4,788,181 | 11/1988 | Driscoll et al. | 514/49 |
| 4,918,075 | 4/1990 | Zahler et al. | 544/314 |
| 4,968,690 | 11/1990 | Marquez et al. | 544/314 |
| 4,975,434 | 12/1990 | Marquez et al. | 544/314 |
| 5,126,345 | 6/1992 | Slusarchyk et al. | 514/254 |

OTHER PUBLICATIONS

Beauchamp et al., "Effect Of Acyclic Pyrimidines . . . ," J. Med. Chem., Jan. 31, 1988, 144–149.

Ogilvie et al., "Synthesis of 5-Substituted . . . " Nucleosides and Nucleotides, 2(2), 147–154 (1983).

Allen et al., "Acyclic Pyrimidine Analogues . . . ," Chemotherapy, 31, 151–159 (1985).

Myska et al., "Azauridine In Viral Eye Infections", Lancet, Jun. 3, 1967, pp. 1230–1231.

Rada et al., "Antiviral Action and Selectivity Of 6-Azauridine", Ann. N.Y. Acad. Sci., vol. 214, (1977), pp. 410–447.

Rada, "The Effect Of Cell-Free Extracts . . . " Ann. N.Y. Acad. Sci., vol. 173, 176–184 (1970).

Temple, et al., J. Me. Pharm. Chem. 5 866 (1962).

Marquez, et al., Medicinal Research Reviews, 6 1–40 (1986).

CARBOCYCLIC NUCLEOSIDE ANALOGS

This is a division of U.S. patent application Ser. No. 420,691, filed Oct. 17, 1989, which is a continuation-in-part of U.S. patent application Ser. No. 319,385, filed Mar. 3, 1989, now abandoned which is a continuation-in-part of U.S. patent application Ser. No. 262,547, filed Oct. 25, 1988, now abandoned.

TECHNICAL FIELD

The present invention relates to novel compounds and compositions which have antiviral and antitumor activity, processes for making such compounds, synthetic intermediates employed in these processes and methods for treating a host in need of antiviral or antitumor treatment.

BACKGROUND ART

Viruses are implicated in a variety of animal and human diseases. Numerous approaches have been proposed to combat these pathogens which include, but are not limited to, herpesviruses 1 and 2 (HSV-1 and HSV-2), influenza viruses A, B and C (orthomyxoviruses), parainfluenza viruses 1-4, mumps virus (paramyxovirus), adenoviruses, respiratory syncytial virus, Epstein-Barr virus, rhinoviruses, human immunodeficiency viruses (HIV), polioviruses, coxsackieviruses, echoviruses, rubella virus, varicella-zoster virus, neurodermotropic virus, variola virus, cytomegalovirus, hepatitis A, B and non-A, non-B viruses, papoviruses and rabies virus.

One approach in the development of antiviral compounds has been to identify compounds which interfere with the normal viral metabolism of nucleosides. Because the structures of these compounds are usually closely related to nucleosides which occur naturally in the mammalian host, few have good activity against the virus without untoward side effects. Some of the few compounds having activity are very expensive to produce. Thus, there is a continuing need for new compounds which act to kill viruses, to inhibit viral replication or to block the pathogenic actions of viruses.

The following references disclose various carbocyclic analogs of nucleosides:

Ichikawa, et al., European Patent Application No. EP0330992, published Sep. 9, 1989, discloses 2-hydroxy-3-hydroxymethylcyclobutyl substituted purines and pyrimidines having antiviral activity;

Zahler, et al., European Patent Application No. EP0322854, published Jul. 5, 1989, discloses 2-hydroxy-3-hydroxymethylcyclobutyl substituted purines and pyrimidines having antiviral activity;

Slusarchyk, et al., European Patent Application No. EP0335355, published Oct. 4, 1989, discloses 2,3-bis(hydroxymethyl)cyclobutyl substituted purines and pyrimidines having antiviral activity;

Tolman, et al., U.S. Pat. No. 4,782,062, issued Nov. 1, 1988, discloses 9-((Z)-2-(hydroxymethyl)cyclobutylmethyl)guanine as a viral thymidine kinase inhibitor;

Kjellin, et al., U.S. Pat. No. 4,644,001, issued Feb. 17, 1987, and U.S. Pat. No. 4,548,818, issued Oct. 22, 1985, disclose cyclopropyl-, cyclobutyl- and cyclopentyl-substituted purine analogs which are useful for treating obstructive airway disease or cardiac disease;

Maccoss, et al., European Patent Application No. EP0184473, published Jun. 11, 1986, discloses 2-amino-9-((2)-2-(benzoyloxymethyl)cyclobutylmethyl)-6-benzoylpurine;

Albrecht, et al., U.S. Pat. No. 3,923,792, issued Dec. 2, 1975, discloses cyclopropyl-, cyclopropylmethyl- and cyclopentyl-substituted cytosine analogs which are useful as antibacterial agents;

Albrecht, et al., U.S. Pat. No. 4,016,267, issued Apr. 5, 1977, discloses cyclopropyl-, cyclopropylmethyl- and cyclopentyl-substituted nucleoside analogs which are useful as antibacterial agents;

Ashton, et al., U.S. Pat. No. 4,617,304, issued Oct. 14, 1986, discloses ((hydroxymethylcyclopropyl)methyl)-substituted purine and pyrimidine analogs as antiviral agents;

Temple, et al., J. Med. Pharm. Chem. 5 866 (1962), discloses cyclopropyl-substituted purine analogs which are useful for treating human epidermal carcinoma;

Masoliver, et al., C.A. 107:236375e, Spanish Patent No. ES519898, published Mar. 16, 1984, discloses cyclopropylmethyl-substituted purine analogs; and Marquez, et al., Medicinal Research Reviews, 6 1–40 (1986) discloses substituted-cyclopentyl nucleoside analogs.

DISCLOSURE OF THE INVENTION

In accordance with the present invention there are antiviral compounds of the formula:

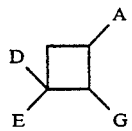

I wherein A is a purin-9-yl group or a heterocyclic isostere of a purin-9-yl group selected from the group consisting of

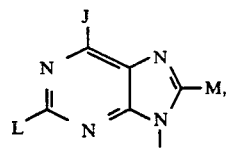

1)

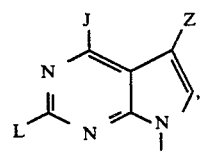

2)

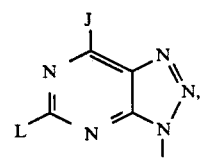

3)

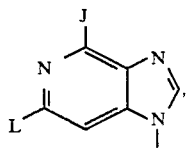 4)

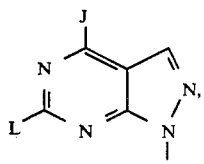 5)

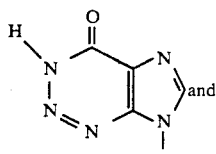 6)

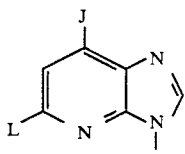 7)

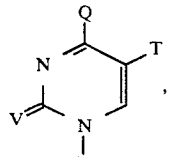 8)

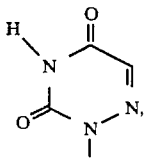 9)

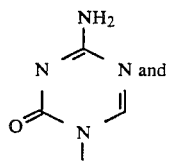 10)

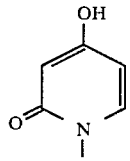 11)

wherein J and L are independently selected from hydrogen, —OH, halogen, alkoxy, —SH, thioalkoxy, —N$_3$,

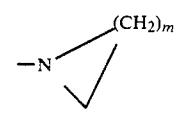

wherein m is 1 to 5, —NR$_1$R$_2$ wherein R$_1$ and R$_2$ are independently selected from hydrogen and C$_1$ to C$_{10}$ alkyl, —NHC(O)R$_3$ wherein R$_3$ is hydrogen, C$_1$ to C$_{10}$ alkyl, carboxyalkyl or aminoalkyl, —N=CHNR$_4$R$_5$ wherein R$_4$ and R$_5$ are independently selected from C$_1$ to C$_{10}$ alkyl, —N(R$_6$)OR$_7$ wherein R$_6$ and R$_7$ are independently selected from hydrogen and C$_1$ to C$_{10}$ alkyl, and —N(R$_8$)NR$_9$R$_{10}$ wherein R$_8$, R$_9$ and R$_{10}$ are independently selected from hydrogen and C$_1$ to C$_{10}$ alkyl; and wherein M is hydrogen, C$_1$ to C$_{10}$ alkyl, halogen,

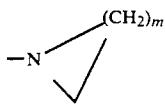

wherein m is 1 to 5, or —NR$_1$R$_2$ wherein R$_1$ and R$_2$ are as defined above; and Z is hydrogen, halogen, formyl, carboxyl, alkoxycarbonyl, carboxamido or cyano; or A is a pyrimidin-1-yl group or a heterocyclic isostere of a pyrimidin-1-yl group selected from the group consisting of wherein
V is O or S;
Q is —OH, —SH, alkoxy, thioalkoxy, halogen,

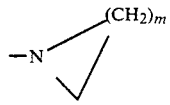

wherein m is 1 to 5, —NR$_1$R$_2$ wherein R$_1$ and R$_2$ are as defined above, or —NHC(O)R$_3$ wherein R$_3$ is as defined above; and T is hydrogen, C$_1$ to C$_{10}$ alkyl, 2-haloethyl, halomethyl, difluoromethyl, trifluoromethyl, halogen, cyano, nitro, vinyl, 2-halovinyl, alkynyl, hydroxmethyl, formyl, azidomethyl, 2-hydroxyethyl, —NR$_1$R$_2$ wherein R$_1$ and R$_2$ are as defined above, —NHOH, —SH, propenyl, 3,3,3-trifluoropropenyl, 2-(alkoxycarbonyl)ethenyl, 2-cyanoethenyl,

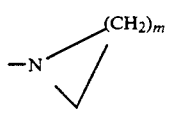

wherein m is 1 to 5, or —CH$_2$NR$_2$R$_2$ wherein R$_1$ and R$_2$ are as defined above; and
wherein E is hydrogen, —CH$_2$OH or —OH; and
G and D are independently selected from hydrogen, C$_1$ to C$_{10}$ alkyl, —OH, —CH$_2$OH, —CH$_2$OR$_{20}$ wherein R$_{20}$ is C$_1$ to C$_6$ alkyl, —CH$_2$OC(O)R$_{21}$ wherein R$_{21}$ is C$_1$ to C$_{10}$ alkyl, —CH$_2$OC-(O)CH(R$_{22}$)(NHR$_{23}$) wherein R$_{22}$ is the side chain of any of the naturally occurring amino acids and R$_{23}$ is hydrogen or —C(O)CH(R$_{24}$)(NH$_2$) wherein R$_{24}$ is the side chain of any of the naturally occurring amino acids, —CH$_2$SH, —CH$_2$Cl, —CH$_2$F, —CH$_2$Br, —CH$_2$I, —C(O)H, —CH$_2$CN, —CH$_2$N$_3$, —CH$_2$NR$_1$R$_2$, —CO$_2$R$_1$, —CH$_2$CH$_2$OH, —CH$_2$CH$_2$OR$_{20}$ wherein R$_{20}$ is as defined above —CH$_2$CH$_2$OC(O)R$_{21}$ wherein R$_{21}$ is as defined above, —CH$_2$CH$_2$OC(O)CH(R$_{22}$)(NHR$_{23}$) wherein R$_{22}$ and R$_{23}$ are as defined above, —CH$_2$CH$_2$PO$_3$H$_2$, —CH$_2$OPO$_3$H$_2$, —OCH$_2$PO$_3$H$_2$ and —CH$_2$CO$_2$R$_3$ wherein R$_1$, R$_2$ and R$_3$ are as defined above, with the proviso that when E is —OH then D is not —OH and with the proviso that when E is hydrogen and D is hydrogen or C$_1$ to C$_{10}$ alkyl then G is not hydrogen or C$_1$ to C$_{10}$ alkyl; or a pharmaceutically acceptable salt thereof.

The term "C$_1$ to C$_{10}$ alkyl" as used herein refers to straight or branched chain alkyl radicals containing from 1 to 10 carbon atoms including, but not limited to, methyl, ethyl, isopropyl, n-butyl, isobutyl, sec-butyl, n-pentyl, 1-methylbutyl, 2,3-dimethylbutyl, 2-methylpentyl, 2,2-dimethylpropyl, n-hexyl, n-heptyl, n-octyl, n-nonyl, n-decyl and the like.

The terms "alkoxy" and "thioalkoxy" as used herein refer to —OR$_{25}$ and —SR$_{25}$, respectively, wherein R$_{25}$ is a C$_1$ to C$_{10}$ alkyl group.

The term "carboxyalkyl" as used herein refers to a carboxylic acid group (—COOH) appended to a C$_1$ to C$_{10}$ alkyl radical.

The term "alkoxycarbonyl" as used herein refers to —C(O)R$_{26}$ wherein R$_{26}$ is an alkoxy group.

The term "aminoalkyl" as used herein refers to an amino group (—NH$_2$) appended to a C$_1$ to C$_{10}$ alkyl radical.

The term "alkynyl" as used herein refers to C$_2$ to C$_6$ straight or branched carbon chain which contains a carbon-carbon triple bond including, but not limited to, ethynyl, propynyl, butynyl and the like.

The term "halo" or "halogen" as used herein refers to Cl, Br, F or I.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxyl, alkoxycarbonyl and carboxamide.

The term "arylalkyl" as used herein refers to an aryl group appended to a loweralkyl radical.

The term "haloalkyl" as used herein refers to a loweralkyl radical in which one or more hydrogen atoms are replaced by halogen including, but not limited to, fluoromethyl, 2-chloroethyl, trifluoromethyl, 2,2-dichloroethyl and the like.

The term "side chain of any of the naturally occurring amino acids" as used herein refers to the functionality appended at the alpha carbon of any of the naturally occurring amino acids and includes, but is not limited to hydrogen (glycine), methyl (alanine), isopropyl (valine), hydroxymethyl (serine), benzyl (phenylalanine), and the like.

The term "heterocyclic isostere of a purin-9-yl group" as used herein refers to a heterocyclic group which has a similar structure and similar properties when compared to a purin-9-yl group. In addition, the isostere may contain different atoms and not necessarily the same number of atoms as long as the isostere possesses the same total or valence electrons in the same arrangement as does a purin-9-yl group. For example, well known isosteric pairs of molecules include the pair carbon monoxide and atmospheric nitrogen and the pair cyanide ion and acetylide ion. Heterocyclic isosteres of a purin-9-yl group include, but are not limited to, compounds of the formula:

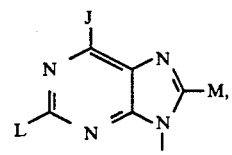

1)

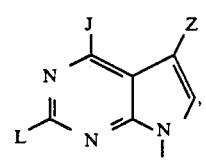

2)

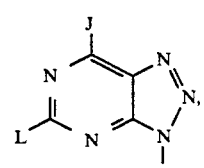

3)

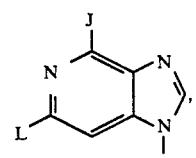

4)

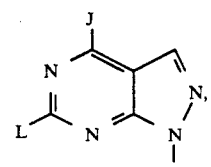

5)

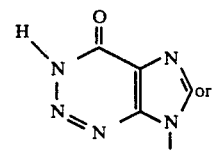

6)

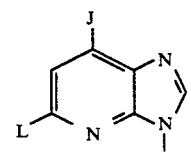

7)

wherein J and L are independently selected from hydrogen, —OH, halogen, alkoxy, —SH, thioalkoxy, —N$_3$,

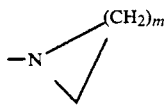

wherein m is 1 to 5, —NR₁R₂ wherein $R_1$ and $R_2$ are independently selected from hydrogen and $C_1$ to $C_{10}$ alkyl, —NHC(O)R₃ wherein $R_3$ is hydrogen, $C_1$ to $C_{10}$ alkyl, carboxyalkyl or aminoalkyl, —N=CHNR₄R₅ wherein $R_4$ and $R_5$ are independently selected from $C_1$ to $C_{10}$ alkyl, —N(R₆)OR₇ wherein $R_6$ and $R_7$ are independently selected from hydrogen and $C_1$ to $C_{10}$ alkyl, and —N(R₈)NR₉R₁₀ wherein $R_8$, $R_9$ and $R_{10}$ are independently selected from hydrogen and $C_1$ to $C_{10}$ alkyl; and wherein M is hydrogen, $C_1$ to $C_{10}$ alkyl, halogen,

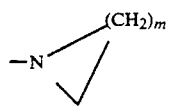

wherein m is 1 to 5, or —NR₁R₂ wherein $R_1$ and $R_2$ are as defined above; and Z is hydrogen, halogen, formyl, carboxyl, alkoxycarbonyl, carboxamido or cyano.

The term "heterocyclic isostere of a pyrimidin-1-yl group" as used herein refers to a heterocyclic group which has a similar structure and similar properties when compared to a pyrimidin-1-yl group. In addition, the isostere may contain different atoms and not necessarily the same number of atoms as long as the isostere possesses the same total or valence electrons in the same arrangement as does a pyrimidin-1-yl group. For example, well known isosteric pairs of molecules include the pair carbon monoxide and atmospheric nitrogen and the pair cyanide ion and acetylide ion. Heterocyclic isosteres of a pyrimidin-1-yl group include, but are not limited to, compounds of the formula:

8)
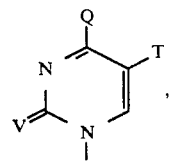

9)
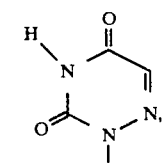

10)
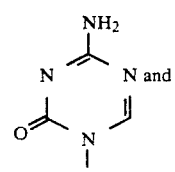

11)
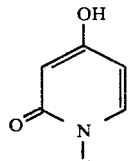

wherein
V is O or S;
Q is —OH, —SH, alkoxy, thioalkoxy, halogen,

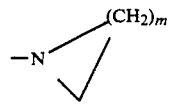

wherein m is 1 to 5, —NR₁R₂ wherein $R_1$ and $R_2$ are as defined above, —NHC(O)R₃ wherein $R_3$ is as defined above; and T is hydrogen, $C_1$ to $C_{10}$ alkyl, 2-haloethyl, halomethyl, difluoromethyl, trifluoromethyl, halogen, cyano, nitro, vinyl, 2-halovinyl, alkynyl, hydroxmethyl, formyl, azidomethyl, 2-hydroxyethyl, —NR₁R₂ wherein $R_1$ and $R_2$ are as defined above, —NHOH, —SH, propenyl, 3,3,3-trifluoropropenyl, 2-(alkoxycarbonyl)ethenyl, 2-cyanoethenyl,

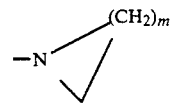

wherein m is 1 to 5, or —CH₂NR₁R₂ wherein $R_1$ and $R_2$ are as defined above.

The compounds of the present invention may be prepared by various methods disclosed in Schemes I to XXV.

According to one method (Scheme I), the adduct of diethyl fumarate and allene (the compound of Formula XIII (Cripps, et al., J. Am. Chem. Soc. 1959, 81, 2723-2728)) is reduced with a reducing agent such as lithium aluminum hydride and then treated with ozone and then dimethyl sulfide to afford the ketone diol of Formula XIV. This compound is, in turn, condensed with O-methyl hydroxylamine and then a suitable reagent to protect the hydroxyl groups, such as t-butyldimethylsilyl chloride (TBS-Cl) to afford the oxime of Formula XV. This compound is, in turn, treated with a reducing agent, preferably Na(BH₃)O₂CCF₃ in tetrahydrofuran (THF) to afford the amine of Formula XVI. This compound is, in turn, treated with a reagent such as chlorotrimethylsilane in methanol to remove the TBS protecting groups and afford the amine hydrochloride of Formula XVII. As demonstrated in subsequent Schemes, compounds of Formula XVI and XVII are key intermediates used in the synthesis of purines, pyrimidines, and their heterocyclic isosteres.

According to one method (Scheme II), the compound of Formula XVII is condensed with 2-amino-4,6-dichloropyrimidine in the presence of a tertiary amine base to afford the pyrimidine of Formula XIX. This compound, is in turn, converted to the pyrimidine of Formula XXI by way of azo coupling with 4-chlorobenzenediazonium chloride and reduction with zinc in acetic acid. The purine of Formula XXII is then prepared by treatment of the pyrimidine of Formula XXI with triethyl orthoformate and acid, or preferably, diethoxymethyl acetate, followed by ammonia in methanol and then a protic acid in methanol. Compounds of Formula XXIII, are in turn, obtained by treating the compound of Formula XXII with various nucleophiles. For instance, treatment of the compound of Formula XXII with aqueous acid affords the compound of Formula XXIII in which $J=OH$; alternatively, treatment of the compound of Formula XXII with ammonia in an alcoholic solvent affords the compound of Formula XXIII in which $J=NH_2$; alternatively, treatment of the compound of Formula XXII (or its diacetate) with hydrogen in the presence of a noble metal catalyst (and then $NH_3$ in MeOH for the diacetate) affords the compound of Formula XXIII in which $J=H$.

According to one method (Scheme III), the compound of Formula XXIII in which $J=OH$ is prepared by the condensation of the compound of Formula XVI with the compound of Formula XXIV in a suitable solvent such as DMF in the presence of a tertiary amine base to afford the compound of Formula XXV. Reduction of this compound by zinc in formic acid, followed by removal of the zinc (or reduction by hydrogen over a noble metal catalyst in formic acid), heating in formic acid, removal of formic acid, treatment with aqueous ammonia, and crystallization from water affords the compound of Formula XXIII.

According to one method (Scheme IV), the compound of Formula XVI is condensed with triemthylsilyl isocyanate and then treated with silica gel to afford the compound of Formula XXVI. This compound is in turn, condensed with either (E)-3-methoxy-2-methylpropenoyl chloride or (E)-3- ethoxyacryloyl chloride to afford compounds of Formula XXVII. These compounds are, in turn, treated with either aqueous acid or base to cause cyclization to compounds of the Formula XXVIII. The compounds are, in turn, treated at elevated temperature with hexamethy disilazane and formamide to afford compounds of the Formula XXIX.

According to one method (Scheme V), the compound of Formula XVII is condensed with 5-amino-4,6-dichloropyrimidine (the compound of Formula XXX) in the presence of a tertiary amine base to afford the pyrimidine of Formula XXXI. This compound is, in turn, treated with triethylorthoformate and acid or preferably diethoxymethyl acetate followed by ammonia in methanol followed by a protic acid in methanol to afford the pyrimidine of Formula XXXII. This compound is, in turn, converted into purines of the Formula XXXIII by the methods outlined above in Scheme II for the conversion of purines of the Formula XXII into purines of the Formula XXIII.

According to one method (Scheme VI), the compound of Formula XXXIV (Cripps, et al. J. Am. Chem. Soc. 1959, 81, 2723-2728) is treated with diphenylphosphoryl azide, triethylamine, and an alcohol such as benzyl alcohol or t-butyl alcohol to afford compounds of the Formula XXXV in which $R_{15}$ is benzyl or t-butyl. These compounds are in turn hydroborated with $BH_3$ in THF to afford the compound of Formula XXXVI in which E is H, or hydroxylated with potassium permanganate to afford the compound of Formula XXXVII in which E is OH. Compounds of the Formula XXXVII are, in turn, converted into compounds of the Formula I by the methods analogous to those outlined above for the preparation of compounds of the Formulas XXII, XXIII, XXVIII, XXIX, XXXII, and XXXIII.

According to one method (Scheme VI), the compound of Formula XXXVIII (Caserio, et al. J. Am. Chem Soc. 1958, 80, 5507-5513) is converted by the action of di-t-butyl dicarbonate to the compound of Formula XXXIX in which $R_{15}$ is t-butyl. This compound is, in turn, treated with ozone and then dimethylsulfide followed by hydroxylamine and hydrogen over a noble metal catalyst to afford the compound of the Formula XL in which $R_{15}$ is t-butyl. This compound is, in turn, converted into compounds of the Formula I by methods analogous to those used in the preparation of compounds of the Formula XXXIII, but removing the t-butyloxycarbonyl protecting group with 4.5M HCl in dioxane.

According to one method (Scheme VII), compounds of the Formula XLI are protected at the 3'-hydroxymethyl group to afford compounds of the Formula XLII, in which TBS may represent any protecting group. In the preferred example, compounds of the Formula XLI are treated with t-butyldimethylsilyl chloride (TBS-Cl) to afford compounds of the Formula XLII in which TBS represents t-butyldimethylsilyl. Compounds of the Formula XLII are in turn treated with methanesulfonyl chloride to afford compounds of the Formula XLIII. These compounds are in turn treated with various nucleophiles and then deprotected. In the preferred example, in which TBS is t-butyldimethylsilyl, the protecting group is removed by trimethylsilyl chloride in methanol. When the nucleophile is azide, X in the compound of Formula XLIV is azido; when the nucleophile is a halide, X is halo; when the nucleophile is cyanide, X is cyano. Treatment of the compound of the Formula XLIV when X is B with tri-n-butyl tin hydride affords the compound of the Formula XLIV in which X is H.

According to one method (Scheme VIII), compounds of the Formula XLI are treated with various acid chlorides or acid anhydrides to afford compounds of the Formulas XLV, XLVI, and XLVII.

According to one method (Scheme IX), the optically pure compound of Formula XLVIII (R is $C_1-C_4$ alkyl) is reduced with a reducing agent such as di-isobutylaluminum hydride to afford the diol of Formula XLIX. The diol is treated with a suitable reagent to protect the hydroxyl groups, such as t-butyldimethylsilyl chloride, and then treated with an oxidizing agent, such as meta-chloroperoxybenzoic acid (mCPBA) to afford the epoxide of Formula LI. This cyclopropyl compound is expanded to the cyclobutanone of Formula LII by treatment with lithium iodide and the ketone is, in turn, converted to the O-methyl oxime ether of the Formula LIII by treatment with O-methyl hydroxylamine in the presence of a base such as pyridine. The oxime ether is reduced with a reducing agent, such as sodium borohydride, in the presence of an equivalent amount of trifluoroacetic acid to afford the amine of Formula LIV. As demonstrated in subsequent Schemes, the compound of Formula LIV is a key intermediate used in the synthesis of compounds of the invention.

According to one method (Scheme X), allene is condensed with a fumarate diester of the Formula LVI (R is $C_1-C_4$ alkyl) to afford the compound of Formula XLVIII. This compound is reduced with a reducing agent, such as lithium aluminum hydride, to the diol of Formula XLIX, which is, in turn, treated with a suitable reagent to protect the hydroxyl groups, such as t-butydimethylsilyl chloride, to afford the compound of Formula L. This compound, in turn, is treated with ozone, followed by dimethyl sulfide, to give the ketone of Formula LII which is, in turn, selectively reduced with a reducing agent such as L-selectride to afford the alcohol of Formula LVII. The protecting groups are removed by treatment with a reagent such as chlorotrimethylsilane to afford the triol of Formula LVIII which is treated with benzaldehyde dimethyl acetal to afford the compound of Formula LIX. The cyclic benzaldehyde acetal of Formula LIX is converted to the compound of Formula LX by treatment with a brominating agent, such as N-bromosuccinimide, in the presence of a base such as barium carbonate. This compound is, in turn, treated with tetra-n-butylammonium fluoride to generate the compound of Formula LXI. The compound of Formula LXI is converted to the ketone of Formula LXII by treatment with ozone, followed by dimethyl sulfide. This compound is, in turn, reduced with a reducing agent, preferably, $(AcO)_3BHNa$, generated in situ from glacial acetic acid and sodium borohydride, to afford the diol of Formula LXIII, which, in turn, is treated with a suitable reagent to protect the hydroxyl groups, such as t-butyldiphenylsilyl chloride to afford the compound of Formula LXIV. This compound is then converted to the compound of Formula LXV by treatment with a reducing agent, such as lithium triethylborohydride. The alcohol is derivatized with methane sulfonyl chloride and the resulting mesylate treated with an azide salt, such as lithium azide, to afford the compound of Formula LXVI. The azide of Formula LXVI is then reduced by hydrogenation in the presence of a catalyst such as palladium on carbon to afford the amino compound of the Formula LXVII. As demonstrated in subsequent Schemes, the compound of Formula LXVII is a key intermediate used in the synthesis of compounds of the invention.

According to one method (Scheme XI), 1,3-dibromo-2,2-dimethoxypropane is condensed with a malonate diester (R is $C_1$-$C_4$ alkyl) of the Formula LXIX to afford the cyclobutane dicarboxylate derivative of Formula LXX. This compound, in turn, is reduced with a reducing agent, such as lithium aluminum hydride, to afford the diol of Formula LXXI which is, in turn, hydrolyzed with a mineral acid, such as hydrochloric acid, to afford the ketone of Formula LXXII. The ketone is then converted to the O-methyl oxime ether by treatment with O-methyl hydroxylamine in the presence of an amine base such as pyridine, followed by treatment with a suitable reagent to protect the hydroxyl groups, such as t-butydimethylsilyl chloride, to afford the compound of Formula LXXIV. The oxime ether is reduced with a reducing agent, such as sodium borohydride, in the presence of an equivalent amount of trifluoroacetic acid to afford the amine of Formula LXXV. As demonstrated in subsequent Schemes, the compound of Formula LXXV is a key intermediate used in the synthesis of compounds of the invention.

According to one method (Scheme XII), methylenecyclobutyl nitrile (LXXVI) is hydrolyzed in aqueous base to the acid of Formula XXXIV, which is then converted to the Cbz-protected amino compound of Formula XXXV by treatment with diphenylphosphonyl azide, in the presence of a tertiary amine base, followed by treatment with benzyl alcohol. This compound is then converted to the keto derivative of Formula LXXVII by treatment with ozone and dimethyl sulfide. This compound, in turn, reduced with a reducing agent such as K-selectride to the corresponding alcohol of Formula LXXVIII which is, in turn, treated with a suitable reagent to protect the hydroxyl groups, such as t-butydimethylsilyl chloride, to afford the compound of Formula LXXIX. This compound is then converted to the amino compound of Formula LXXX by hydrogenolysis in the presence of a catalyst, such as 10% palladium on carbon. As demonstrated in subsequent Schemes, the compound of Formula LXXX is a key intermediate used in the synthesis of compounds of the invention.

According to one method (Scheme XIII), the compound of Formula LXXXI is reduced with a reducing agent, such as diborane to the triol of Formula LXXXII. This compound is then treated with a suitable reagent to protect the primary hydroxyl groups, such as t-butydimethylsilyl chloride, followed by treatment of the secondary hydroxyl group with methanesulfonyl chloride, to afford the compound of Formula LXXXIV. The mesylate (LXXXIV) is treated with lithium azide to afford the azido compound of Formula LXXXV, which is, in turn, reduced by catalytic hydrogenation to afford the amino compound of the Formula LXXXVI. As demonstrated in subsequent Schemes, the compound of Formula LXXXVI is a key intermediate used in the synthesis of compounds of the invention.

According to one method (Scheme XIV), the compounds of Formulas LXXXIX–XCIII are prepared by the condensation of the compound of Formula XXIV with an amino compound, such as one of the compounds of Formulas LIV, LXVII, LXXV, LXXX or LXXXVI, in a suitable solvent, such as DMF, in the presence of a tertiary amine base to afford the compounds of Formula LXXXVII. Reduction of the nitro group with zinc in formic acid or by catalytic hydrogenation, followed by heating in formic acid and then treatment with $NH_4OH$ affords the compounds of Formulas LXXXIX–XCIII. The compound of Formula XCII is then converted to the compound of Formula XCIV by treatment with diethylphosphonomethyl triflate in the presence of a suitable base, such as sodium hydride, followed by cleavage of the phosphonate ester.

According to one Scheme (Scheme XV), an amino compound, for example one of the compounds of Formulas LIV, LXVII, LXXV, LXXX or LXXXVI, is condensed with 5-amino-4,6-dichloropyrimidine (XXX) in the presence of a tertiary amine base to afford a pyrimidine of Formula XCV. This compound, in turn, is converted to a 6-chloropurine derivative of Formula XCVI by treatment with dimethoxymethyl acetate. This compound, in turn, is treated with ammonia in methanol to afford the compounds of Formula XCVII. The hydroxyl protecting groups are removed by treatment of the compound of Formula XCVII with a reagent such as chlorotrimethylsilane/methanol to afford the purine compounds of Formulas XCVIII–CII. The compound of Formula CI is then converted to the compound of Formula CIII by treatment with diethylphosphonomethyl triflate in the presence of a suitable base, such as sodium hydride, followed by cleavage of the phosphonate ester.

According to one Scheme (Scheme XVI) an amine, such as one of the compounds of Formulas LIV, LXVII, LXXV, LXXX or LXXXVI, is condensed with trimethylsilylisocyanate and then treated with silica gel to afford the compounds of Formula CIV. This compound is in turn, condensed with either (E)-3-methoxy-2-methylpropenoyl chloride or (E)-3-ethoxyacryloyl chloride to afford compounds of Formula CV. These compounds are, in turn, treated with either aqueous acid or base to cause cyclization to compounds of the Formula CVI-CXV. The compounds of the Formula CVI-CXV are, in turn, treated at elevated temperature with hexamethyldisilazane and formamide to afford compounds of the Formulas CXVII-CXXVI. The compounds of Formula CIX and CXIV are then converted to the compounds of Formula CXVI by treatment with diethylphosphonomethyl triflate in the presence of a suitable base, such as sodium hydride, followed by cleavage of the phosphonate ester to afford the compounds of Formula CXVI. The compounds of Formula CXX and CXXV are converted to the compounds of Formula CXXVII by treatment with diethylphosphonomethyl triflate in the presence of a suitable base, such as sodium hydride, followed by cleavage of the phosphonate ester to afford the compounds of Formula CXXVII.

According to one Scheme (Scheme XVII), in which A is as defined for Formula I, the compound of Formula CXXVIII is dehydrobrominated by treatment with a base, such as potassium hydroxide, in a suitable solvent, such as toluene, to the unsaturated cyclobutanecarboxylic acid of Formula CXXIX, which is converted to the corresponding methyl ester (CXXX in which R is methyl) with diazomethane. The unsaturated ester of Formula CXXX is then condensed with a pyrimidine or purine base, or a heterocyclic isostere thereof, in a Michael addition to afford the compound of Formula CXXXI. This compound, in turn, is reduced by treatment with a reducing agent, such as lithium borohydride or lithium aluminum hydride, to the hydroxymethyl derivative of Formula CXXXII.

According to one Scheme (Scheme XVIII), in which A is as defined for Formula I, diethyl ketene acetal (CXXXIII) and a propiolate ester (R is $C_1$-$C_4$ alkyl) of Formula CXXXIV are condensed to afford the cyclobutyl compound of Formula CXXXV. This compound is then condensed with a pyrimidine or purine base, or a heterocyclic isostere thereof, in a Michael addition to afford the compound of Formula CXXXVI. This compound is further converted to the hydroxymethyl compound of Formula CXXXVII by reduction with a reducing agent such as lithium aluminum hydride. The diethyl ketal is hydrolyzed to the ketone of Formula CXXXVIII in acidic solution and the ketone is subsequently reduced with a reducing agent, such as sodium borohydride, to afford the compound of Formula CXXXIX. This compound is then treated with a suitable reagent to protect the primary hydroxyl group, such as t-butydimethylsilyl chloride to afford the compound of Formula CXXXX. This compound is converted to the compound of Formula CXXXXI by treatment with diethylphosphonomethyl triflate in the presence of a suitable base, such as sodium hydride, followed by removal of the hydroxyl protecting groups by treatment with a reagent such as bromotrimethylsilane to afford the compound of Formula CXXXXI.

According to one method (Scheme XIX), the compounds of Formula XLI, in which A is guanine or adenine, are treated with Aldrithiol-2 in the presence of tributylphosphine to afford the compounds of Formula CXXXXII. These compounds, in turn, are reduced with sodium in liquid ammonia to afford the compounds of Formula CXXXXIII.

According to one method (Scheme XX), a chloropyrimidine of the Formula CXXXXIV is condensed with an aminocyclobutane, such as the compound of Formula XVII in the presence of a tertiary amine base at ambient or elevated temperature to afford the compounds of Formula CXXXXV. These compounds are, in turn, cyclized in acidic solution to afford compounds of the Formula CXXXXVI. These compounds are then treated with a suitable reagent to protect the primary hydroxyl groups, such as acetic anhydride in the presence of a tertiary amine base to afford the compounds of the Formula CXXXXVII. These compounds are, in turn, brominated with a suitable brominating agent, such as N-bromoacetamide to afford the compounds of Formula CXXXXVIII. The removal of the hydroxyl protecting groups by treatment with a basic reagent such as ammonia in methanol affords the compounds of Formula CXXXIX According to one method (Scheme XXI A), a vinyl thioether of the Formula (CL), wherein $R^{27}$ is alkyl, phenyl or substituted phenyl, is condensed with a fumaric or maleic acid diester of the Formula CLI, wherein $R^{28}$ and $R^{29}$ are independently selected from loweralkyl, aryl and arylalkyl, in the presence of a Lewis acid catalyst such as aluminum trichloride or ethylaluminum dichloride, in a suitable solvent at a temperature in the range of $-78°$ C. to $110°$ C., to give a cyclobutyl sulfide of the Formula CLII. Preferably, phenyl vinyl sulfide is condensed with dimethyl fumarate in the presence of ethylaluminum dichloride in methylene chloride at ambient emperature. Oxidation of a sulfide of the Formula CLII with an oxidant such as 3-chloroperoxybenzoic acid (mCPBA), other peracids, hydrogen peroxide in acetic acid or oxone ⓡ (a commercially available mixture of sulfuric acid potassium salt and potassium hydrogen peroxymonosulfate), gives a sulfone diester of the Formula CLIII.

According to one method (Scheme XXI B), a vinyl thioether of the Formula CL, wherein $R^{27}$ is alkyl, phenyl or substituted phenyl, is condensed with maleic anhydride (CLIV), in the presence of a Lewis acid catalyst such as aluminum trichloride or ethylaluminum dichloride, in a suitable solvent at a temperature in the range $-78°$ C. to $110°$ C., to give an anhydride of the Formula CLV. Preferably, phenyl vinyl sulfide is condensed with maleic anhydride in the presence of ethylaluminum dichloride in methylene chloride at ambient temperature. Treatment of the compound of Formula CLV with an alcohol such as methanol under acidic conditions yields a diester of Formula CLII. Oxidation of the sulfide of the Formula CLII with an oxidant such as mCPBA, other peracids, hydrogen peroxide in acetic acid or oxone ⓡ, gives a sulfone diester of the Formula CLIII. Alternately, oxidation of a sulfide of the Formula CLV with an oxidant such as mCPBA, hydrogen peroxide in acetic acid, other peracids or OXONE gives a sulfone diester of the Formula CLVI. Treatment of a compound of Formula CLVI with an alcohol such as methanol under acidic conditions yields a diester of the Formula CLIII.

According to one method (Scheme XXII) a sulfone of the Formula CLIII is coupled with a nucleophile of the Formula CLVII, wherein A is a purin-9-yl group or a heterocyclic isostere of a purin-9-yl group as defined for Formula I, under conditions suitable to effect elimination of the elements of $HSO_2R^{27}$ to afford the compound of the Formula CLIX, for example at a sufficiently elevated temperature or in the presence of a suitable base such as sodium hydride, potassium hydride, diazabicycloundecene, diazabicyclononane or diazabicyclooctane, in solvents such as DMF or DMSO at ambient or elevated temperature to yield compounds of the Formula CLIX, presumably via the conjugate addition of compounds of the Formula CLVII to the double bond in the intermediate of the Formula CLVIII. Optionally, treatment of the reaction mixture containing product CLIX with a suitable base in a suitable solvent, preferably with sodium methoxide in methanol, increases the proportion of the preferred isomer of compounds of the Formula CLIX. Reduction of compounds of the Formula CLIX with a reducing agent such as lithium aluminum hydride or sodium borohydride-methanol yields compounds of the Formula XLI. In certain cases, treatment of compounds of the Formula XLI with aqueous acids such as hydrochloric acid, with aqueous bases such as sodium hydroxide or with ammonia yields other compounds of Formula CLIX, wherein the group A has been modified by this treatment.

According to one method (Scheme XXIII A), a mixture of a vinyl halide of the Formula CLX, wherein X is selected from Cl, Br, and I, and maleic anhydride in a suitable solvent is irradiated with ultraviolet light in the presence of a sensitizer to yield a compound of the Formula CLXI. Preferably, vinyl bromide and maleic anhydride in ethyl acetate are irradiated with a medium pressure mercury vapor lamp in the presence of acetophenone to yield a compound of the Formula CLXI with X=Br. Treatment of a compound of the Formula CLXI with an alcohol such as methanol under acidic conditions yields a diester of the Formula CLXII, wherein $R^{28}$ and $R^{29}$ are independently selected from loweralkyl, aryl and arylalkyl.

According to one method (Scheme XXIII B), a cyclobutyl sulfide of the Formula CLII, wherein $R^{28}$ and $R^{29}$ are independently selected from loweralkyl, aryl and arylalkyl, is treated with one equivalent of an oxidant such as mCPBA, other peracids, hydrogen peroxide in acetic acid or oxone ® to give a sulfoxide diester Of the Formula CLXIII.

According to one method (Scheme XXIII C), compounds of Formula XLXIV, prepared as described by Cripps, et al. in *J Am Chem Soc.* 81, 2723-8 (1959) utilizing, in addition to diethyl fumarate, other esters of fumaric acid, wherein $R^{28}$ and $R^{29}$ are independently selected from loweralkyl, aryl and arylalkyl, are treated with ozone and then with dimethyl sulfide to afford the ketone diesters of the formula CLXV. Treatment of these compounds with a reducing agent such as sodium borohydride, sodium cyanoborohydride, or diisobutylaluminum hydride in a suitable solvent yields compounds of the Formula CLXVI. Alcohols of the Formula CLXVI can be activated toward elimation by methods well known in the art, for example by treatment with methanesulfonyl chloride or paratoluenesulfonyl chloride and triethylamine, or with acetic anhydride in pyridine, to yield compounds of the Formula CLXVII.

According to one method (Scheme XXIV), a cyclobutane of the Formula CLXII, wherein $R^{28}$ and $R^{29}$ are independently selected from loweralkyl, aryl and arylalkyl; and X is a leaving group such as Cl, Br, I, alkyl sulfoxide, acetate, or an aryl sulfonate or alkyl sulfonate well known in the art (e.g., OTs or OMs), is coupled with a nucleophile of the Formula CLVII, wherein A is a purin-9-yl group or a heterocyclic isostere of a purin-9-yl group as defined for Formula I, under conditions suitable to effect elimination of the elements of HX to afford the compound of the Formula CLIX, for example at a sufficiently elevated temperature or in the presence of a base such as sodium hydride, potassium hydride, diazabicycloundecene, diazabi-cyclononane, or diazabicyclooctane in solvents such as dimethylformamide or dimethylsulfoxide at ambient or elevated temperature, to yield compounds of the Formula CLIX, presumably via the conjugate addition of compounds of the Formula CLVII to the double bond in the intermediate of the Formula CLVIII. Reduction of compounds of the Formula CLIX with a reducing agent such as lithium aluminum hydride or sodium borohydride-methanol yields compounds of the Formula XLI.

According to one method (Scheme XXV), a cyclobutane of the Formula CLXI, wherein X is a leaving group such as Cl, Br, I, alkyl sulfoxide, aryl sulfoxide, alkyl sulfone, aryl sulfone, acetate, or an aryl sulfonate or alkyl sulfonate well known in the art (e.g., OTs or OMs) is coupled with a nucleophile of the Formula CLVII, wherein A is a purin-9-yl group or a heterocyclic isostere of a purin-9-yl group as defined for Formula I, under conditions suitable to effect elimination of the elements of HX to afford the compound of the Formula CLXIX, for example at a sufficiently elevated temperature or in the presence of a base such as sodium hydride, potassium hydride, diazabicycloundecene, diazabicyclononane, or diazabicyclooctane in solvents such as dimethylformamide or dimethylsulfoxide at ambient or elevated temperature, to yield compounds of the Formula CLXIX (wherein $R^{28}$ and $R^{29}$ are independently selected loweralkyl, aryl and arylalkyl), presumably via the conjugate addition of compounds of the Formula CLVII to the double bond in the intermediate of the Formula CLXVIII. Treatment of a compound of the Formula CLXIX with alcohol under acidic conditions yields a diester of the Formula XLIX. Optionally, treatment of the reaction mixture with a suitable base in a suitable solvent, preferably with sodium methoxide in methanol, increases the proportion of the preferred isomer of compounds of the Formula XLIX. Reduction of compounds of the Formula XLIX with a reducing agent such as lithium aluminum hydride or sodium borohydride-methanol yields compounds of the Formula XLI. In certain cases, treatment of compounds of the Formula XLI with aqueous acids such as hydrochloric acid, with aqueous bases such as sodium hydroxide, or with ammonia yields other compounds of the Formula XLI wherein the group A has been modified by this treatment.

SCHEME I

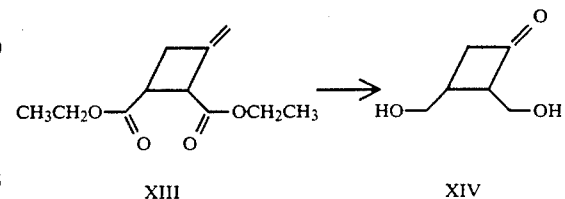

XIII      XIV

-continued
SCHEME I
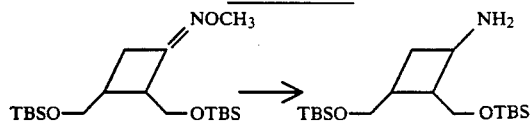
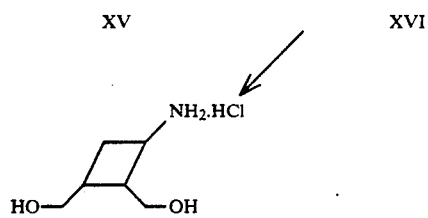
SCHEME II
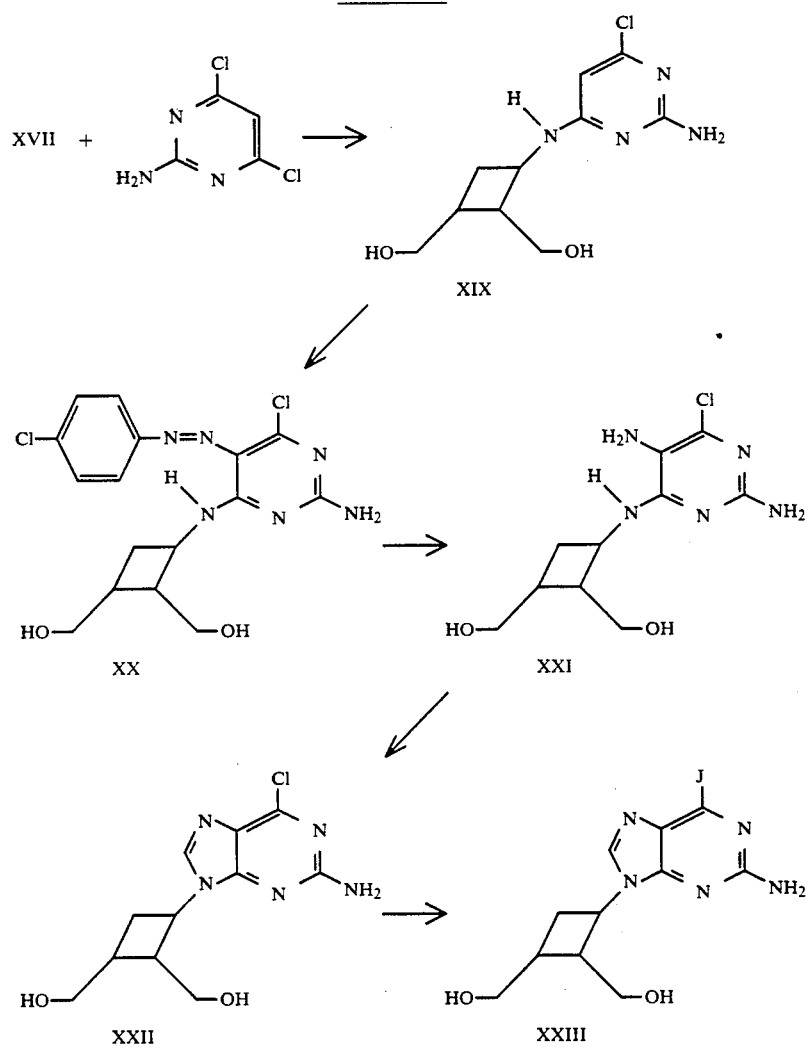

SCHEME III
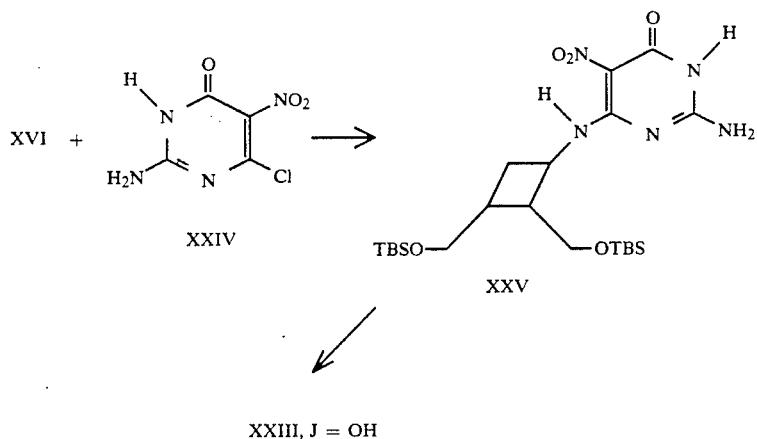
XXIII, J = OH
SCHEME IV
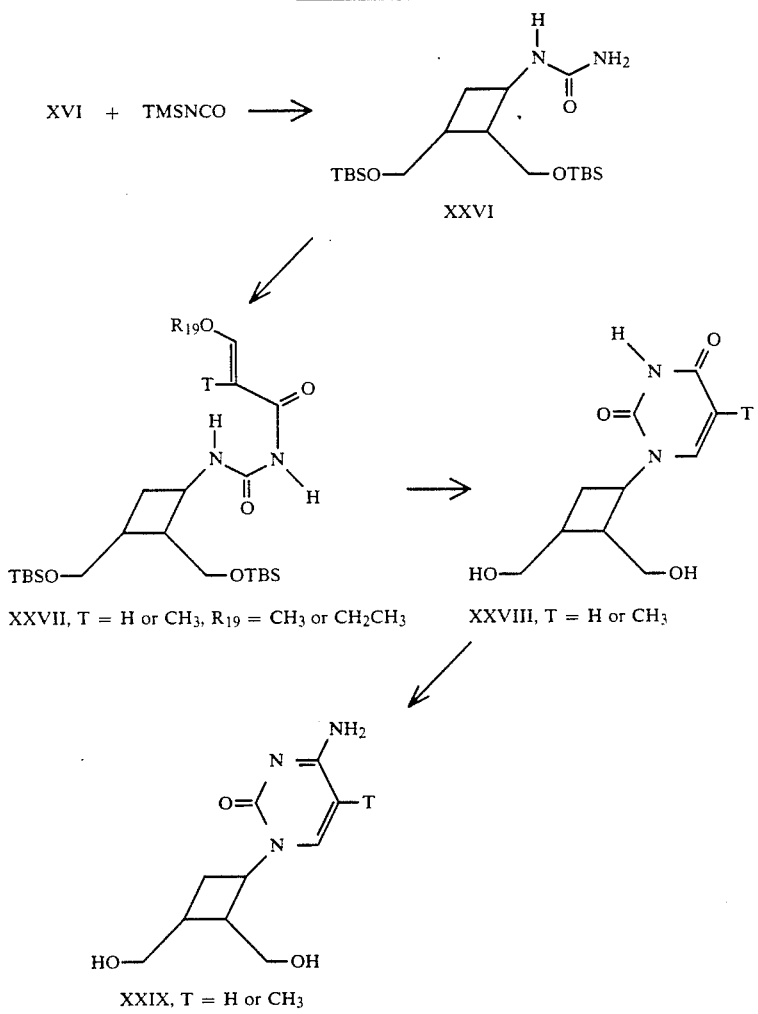

5,246,931
21
SCHEME V
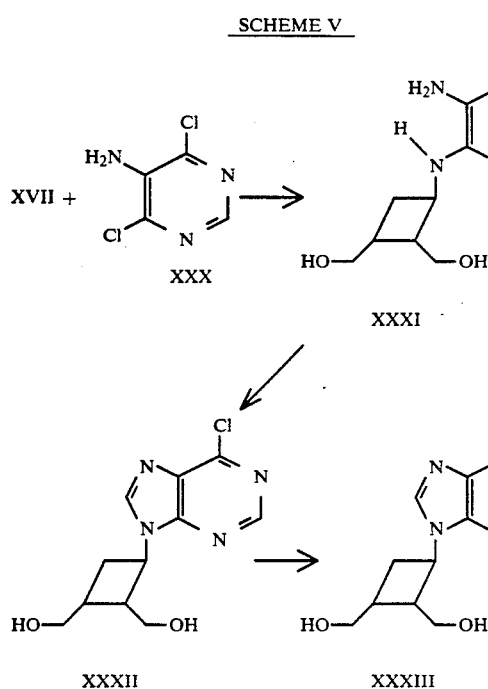
SCHEME VI
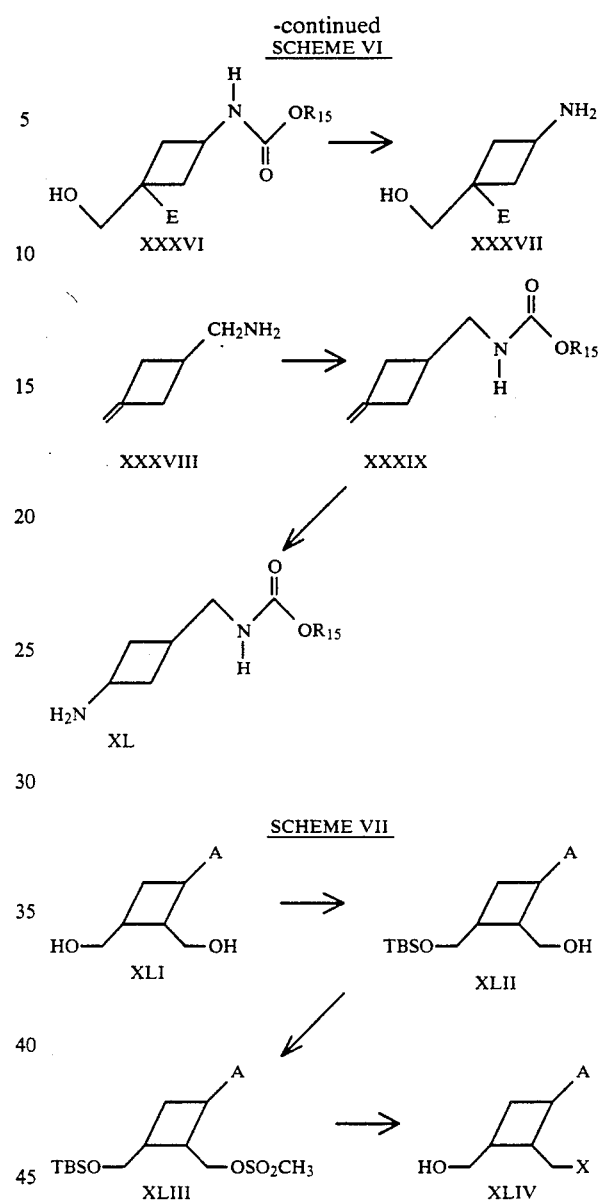
22
SCHEME VII
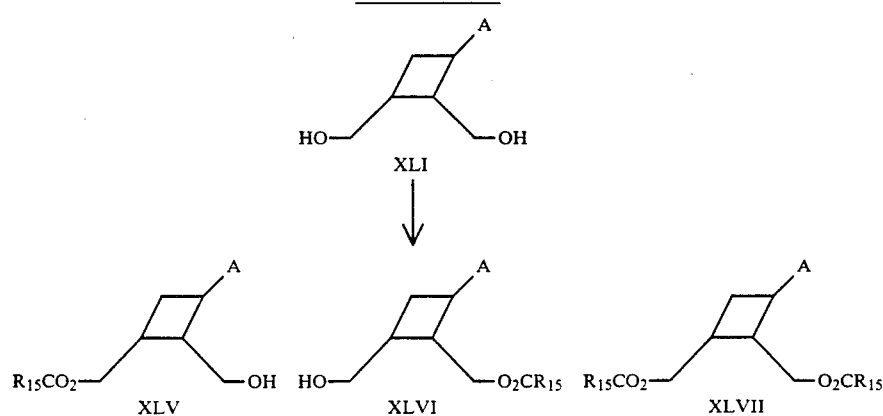
SCHEME VIII SCHEME IX
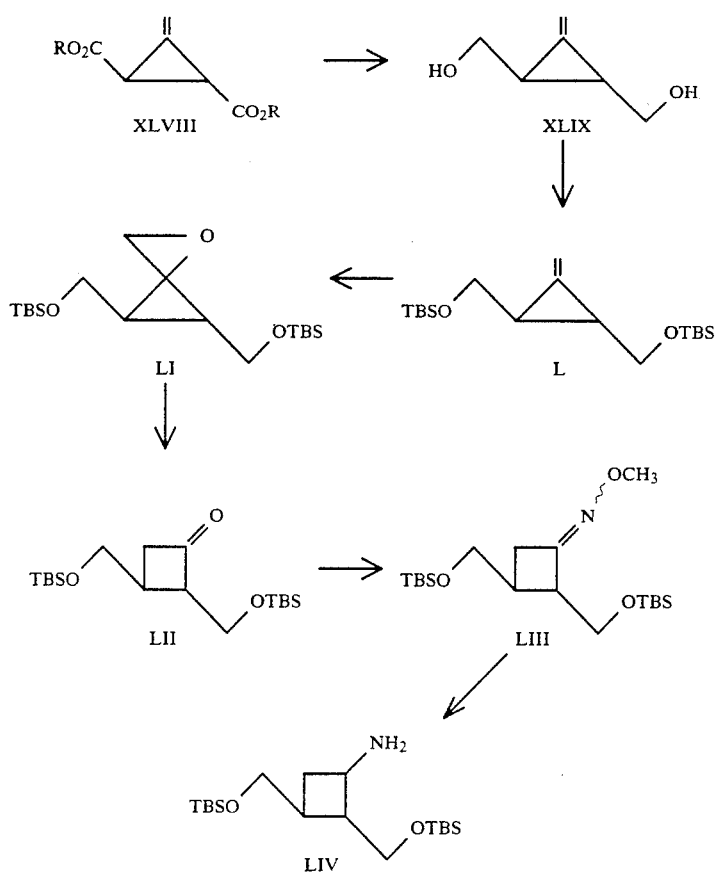
SCHEME X
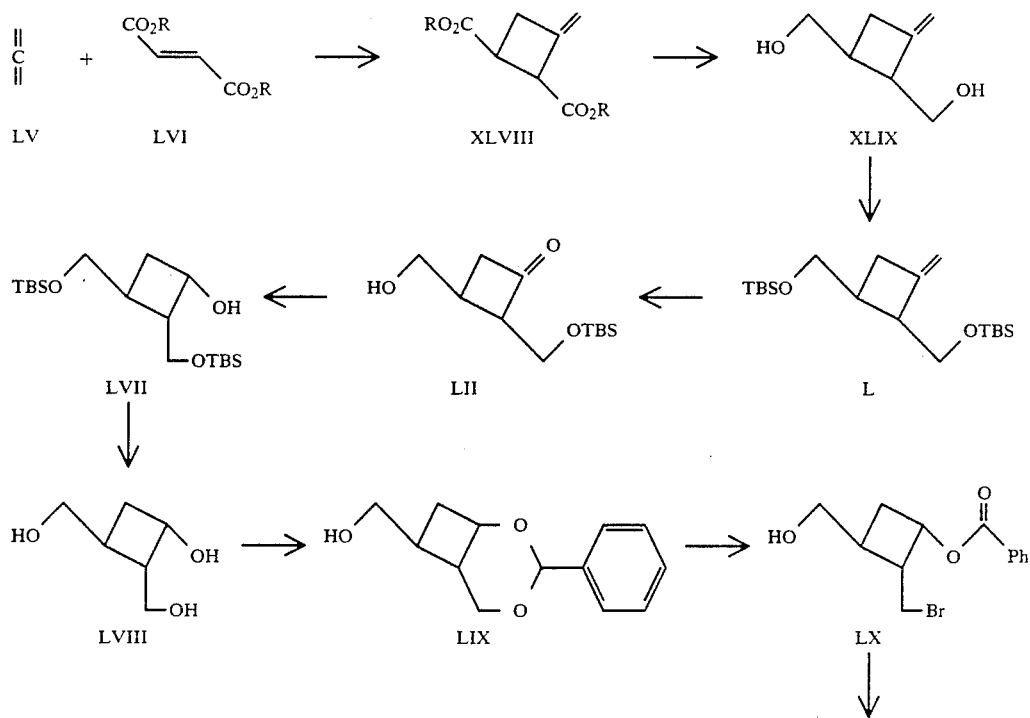

5,246,931
-continued
SCHEME X
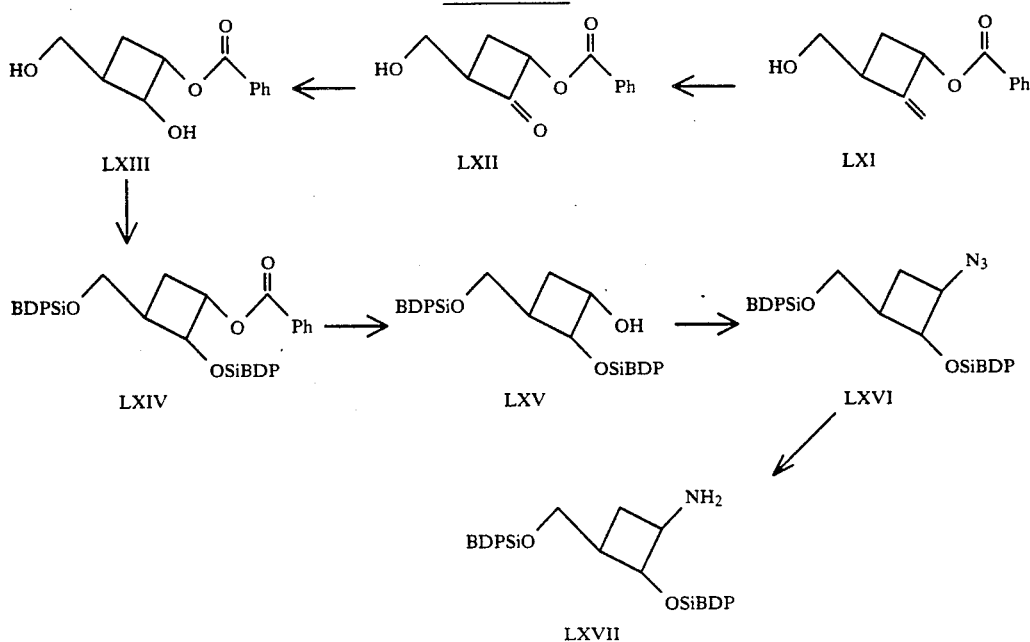
SCHEME XI
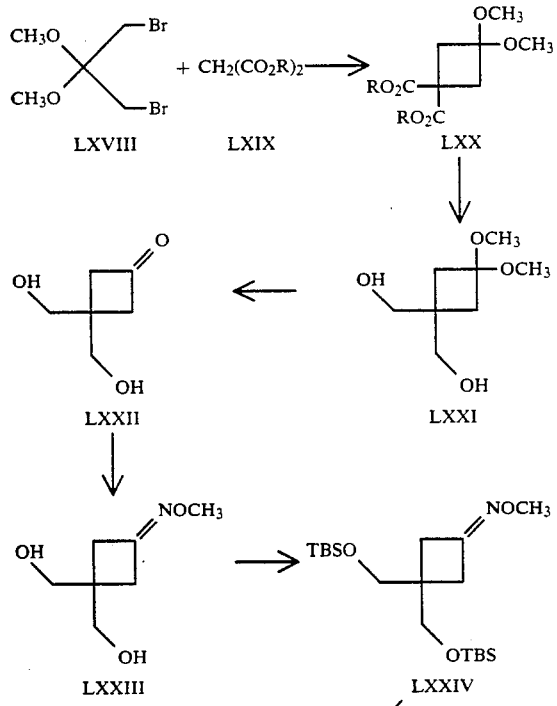
SCHEME XII
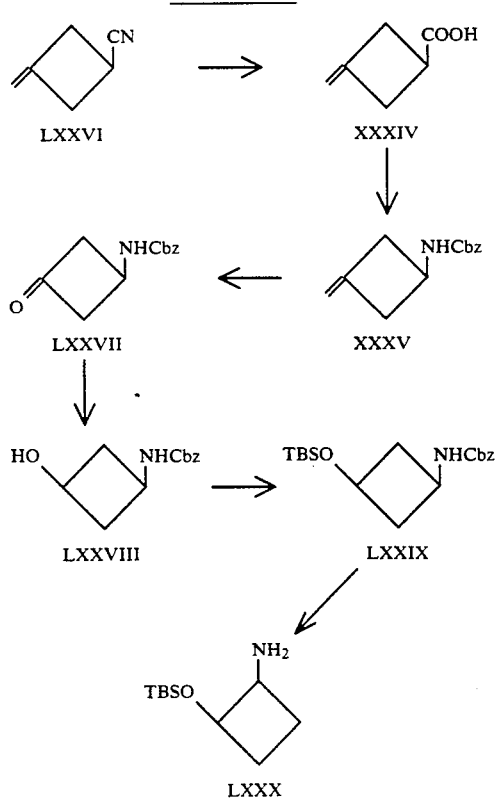

5,246,931
SCHEME XIII
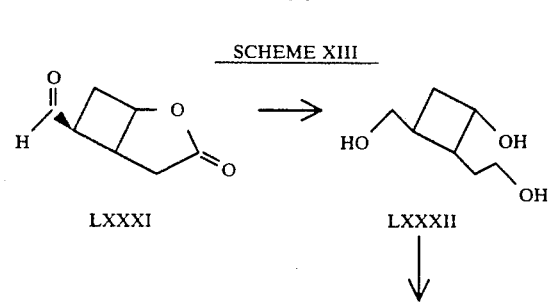
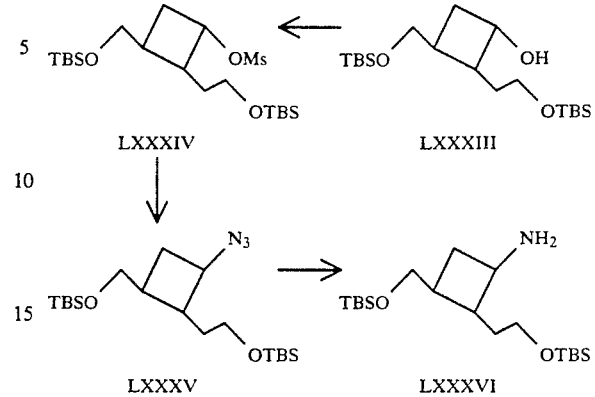
SCHEME XIV
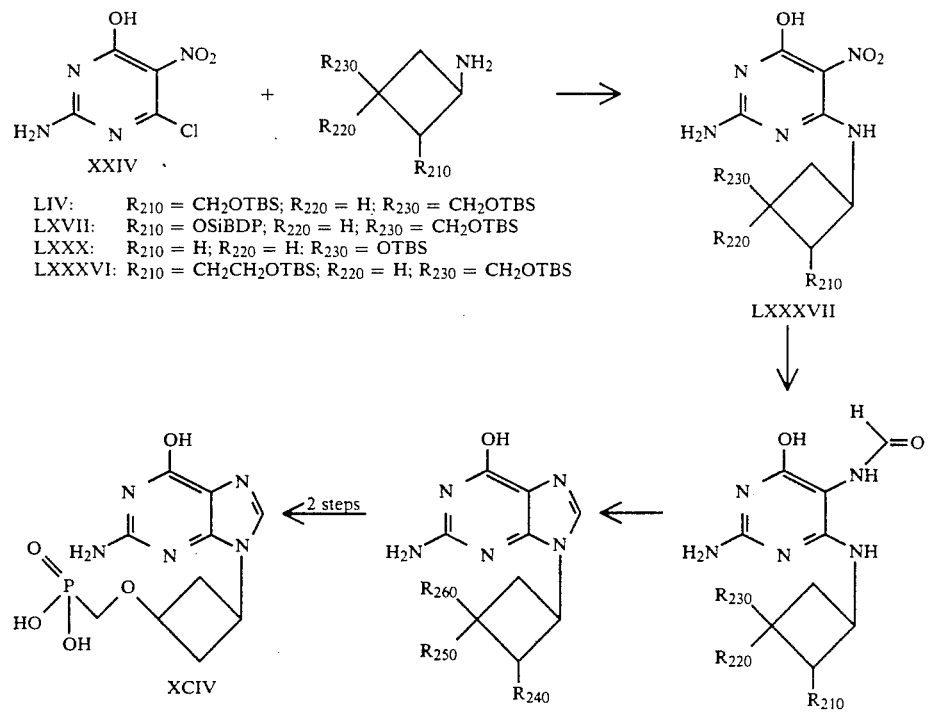
LIV:     $R_{210} = CH_2OTBS; R_{220} = H; R_{230} = CH_2OTBS$
LXVII:   $R_{210} = OSiBDP; R_{220} = H; R_{230} = CH_2OTBS$
LXXX:    $R_{210} = H; R_{220} = H; R_{230} = OTBS$
LXXXVI:  $R_{210} = CH_2CH_2OTBS; R_{220} = H; R_{230} = CH_2OTBS$
LXXXIX:  $R_{240} = CH_2OH; R_{250} = H; R_{260} = CH_2OH$
XC:      $R_{240} = OH; R_{250} = H; R_{260} = CH_2OH$
XCI:     $R_{240} = H; R_{250} = CH_2OH; R_{260} = CH_2OH$
XCII:    $R_{240} = H; R_{250} = H; R_{260} = OH$
XCIII:   $R_{240} = CH_2CH_2OH; R_{250} = H; R_{260} = CH_2OH$

SCHEME XV

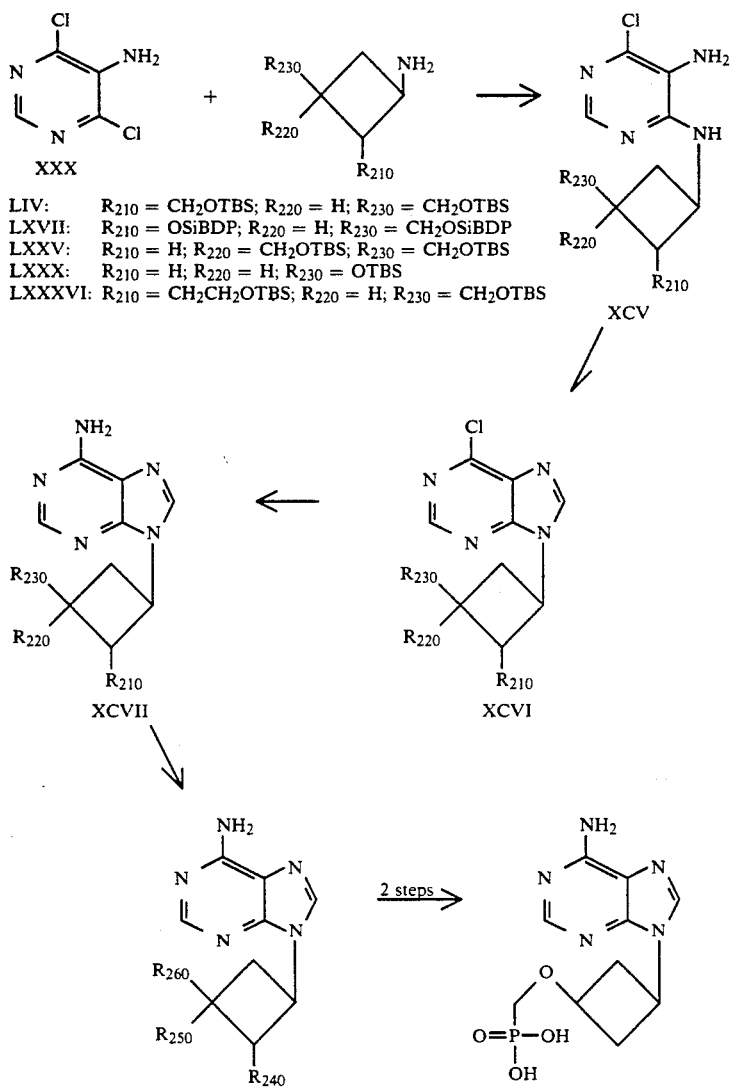

| | |
|---|---|
| LIV: | $R_{210} = CH_2OTBS$; $R_{220} = H$; $R_{230} = CH_2OTBS$ |
| LXVII: | $R_{210} = OSiBDP$; $R_{220} = H$; $R_{230} = CH_2OSiBDP$ |
| LXXV: | $R_{210} = H$; $R_{220} = CH_2OTBS$; $R_{230} = CH_2OTBS$ |
| LXXX: | $R_{210} = H$; $R_{220} = H$; $R_{230} = OTBS$ |
| LXXXVI: | $R_{210} = CH_2CH_2OTBS$; $R_{220} = H$; $R_{230} = CH_2OTBS$ |

| | |
|---|---|
| XCVIII: | $R_{240} = CH_2OH$; $R_{250} = H$; $R_{260} = CH_2OH$ |
| IC: | $R_{240} = OH$; $R_{250} = H$; $R_{260} = CH_2OH$ |
| C: | $R_{240} = H$; $R_{250} = CH_2OH$; $R_{260} = CH_2OH$ |
| CI: | $R_{240} = H$; $R_{250} = H$; $R_{260} = OH$ |
| CII: | $R_{240} = CH_2CH_2OH$; $R_{250} = H$; $R_{260} = CH_2OH$ |

SCHEME XVI

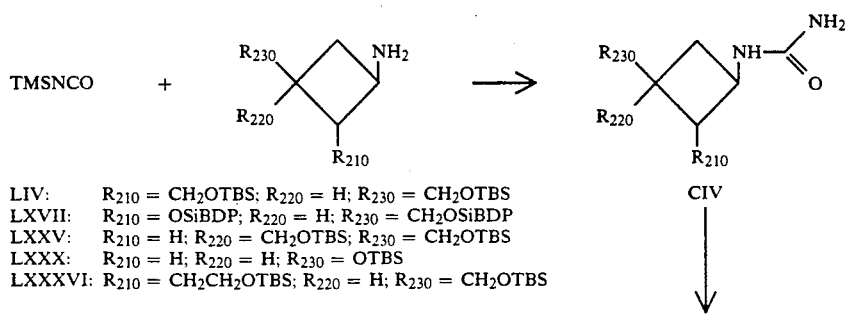

| | |
|---|---|
| LIV: | $R_{210} = CH_2OTBS$; $R_{220} = H$; $R_{230} = CH_2OTBS$ |
| LXVII: | $R_{210} = OSiBDP$; $R_{220} = H$; $R_{230} = CH_2OSiBDP$ |
| LXXV: | $R_{210} = H$; $R_{220} = CH_2OTBS$; $R_{230} = CH_2OTBS$ |
| LXXX: | $R_{210} = H$; $R_{220} = H$; $R_{230} = OTBS$ |
| LXXXVI: | $R_{210} = CH_2CH_2OTBS$; $R_{220} = H$; $R_{230} = CH_2OTBS$ |

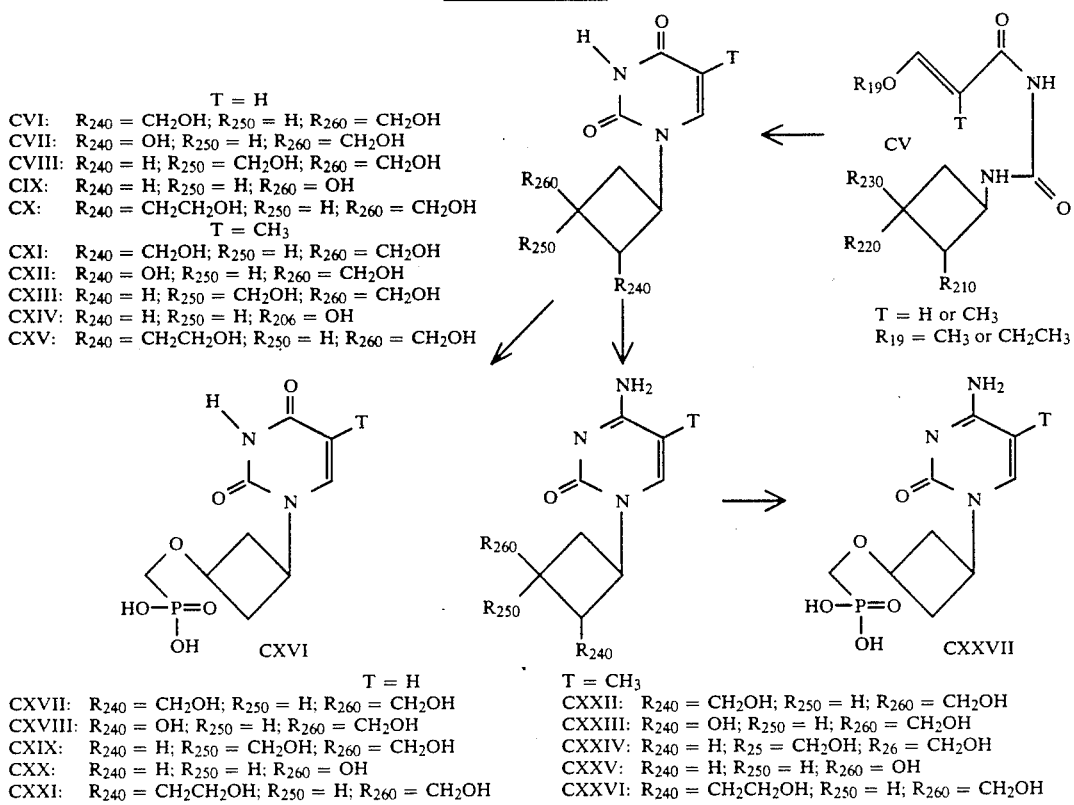

SCHEME XIX
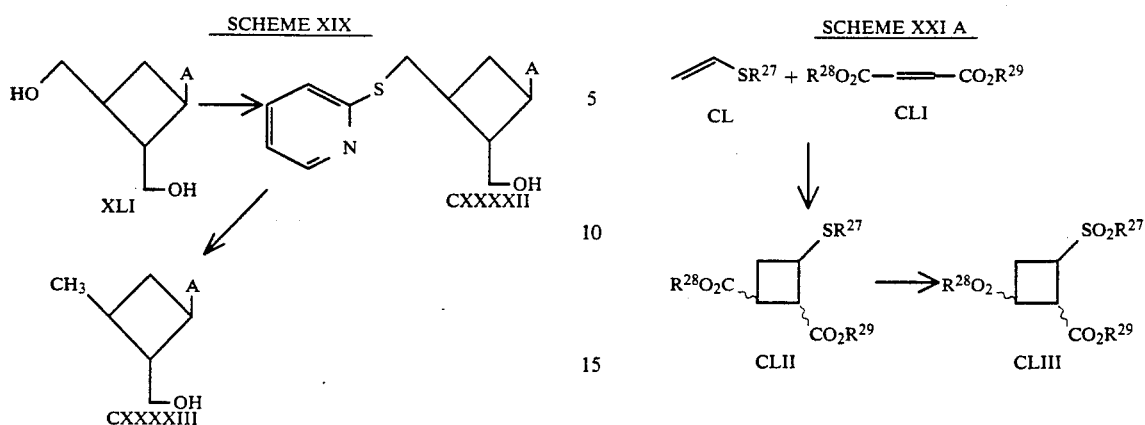
SCHEME XXI A
SCHEME XX
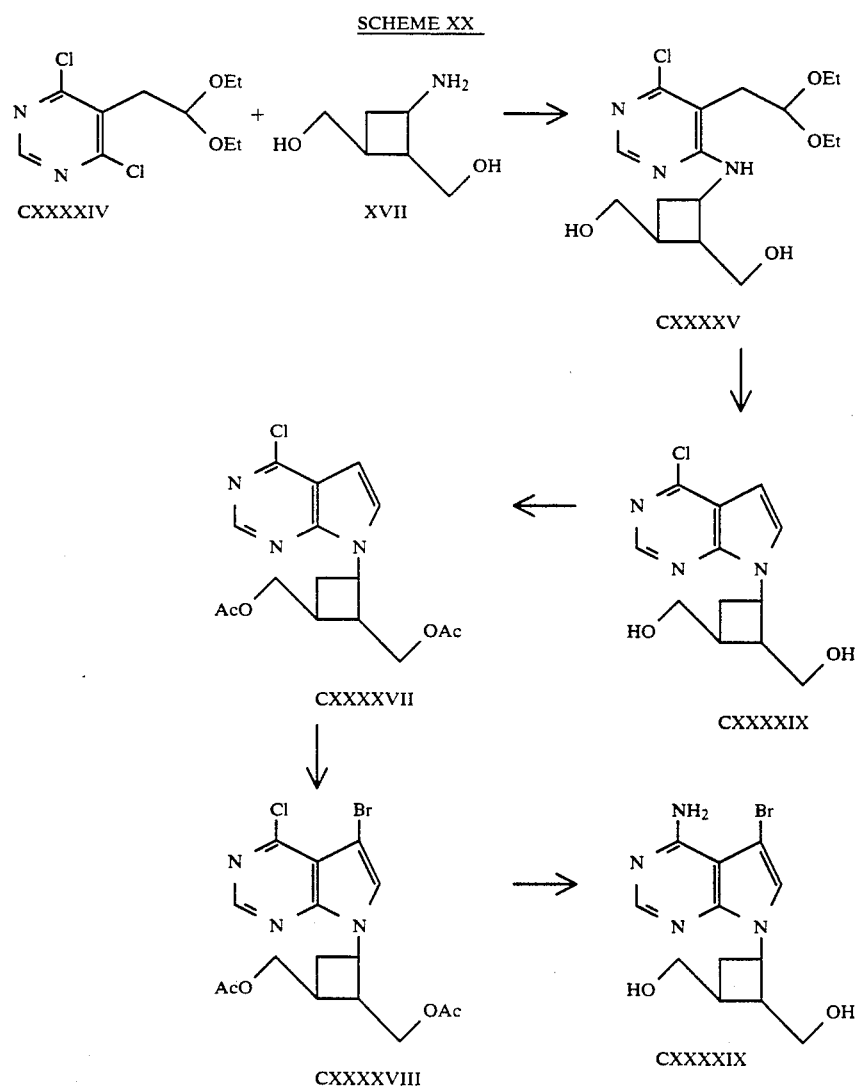

SCHEME XXI B
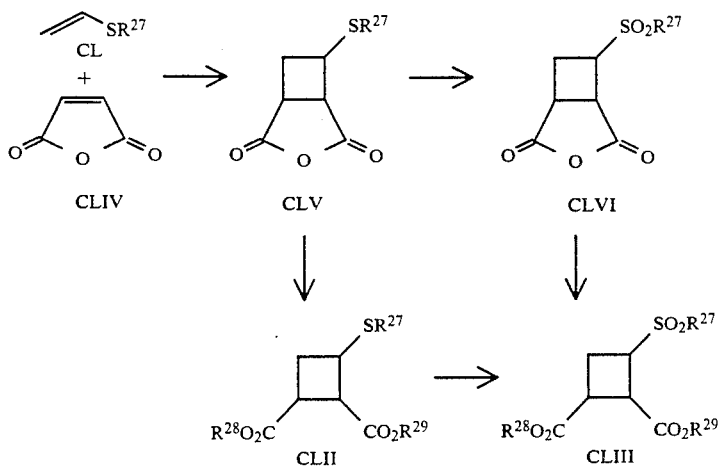
SCHEME XXII
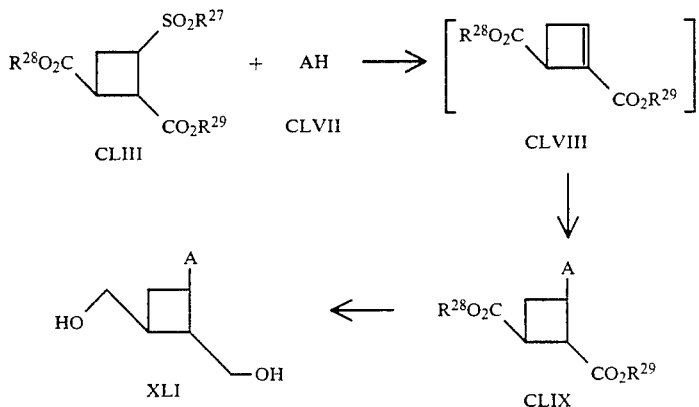
SCHEME XXIII A
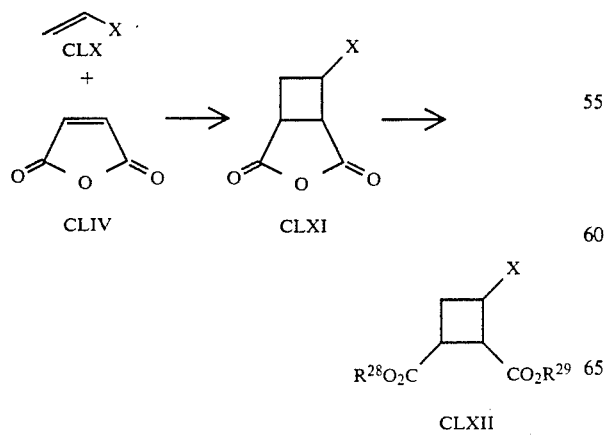
SCHEME XXIII B
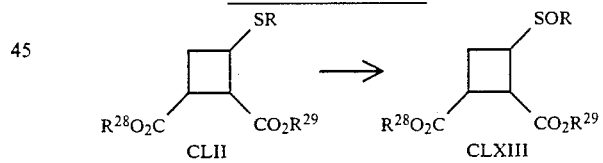
SCHEME XXIII C
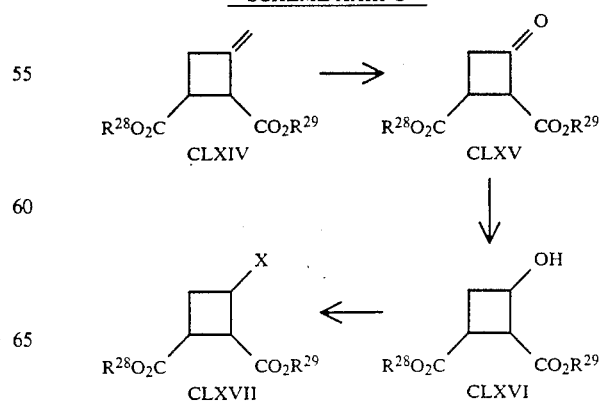

SCHEME XXIV

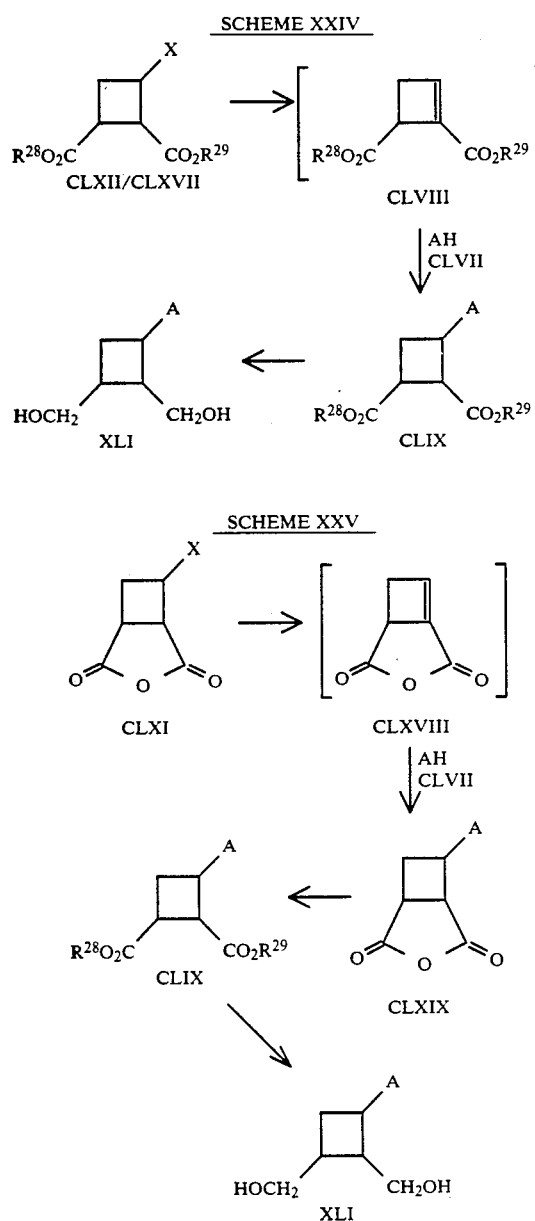

SCHEME XXV

Useful intermediates for the preparation of compounds of the invention include compounds of the formula:

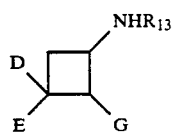

wherein
E is hydrogen, —$CH_2OH$, —$CH_2OR_{11}$, —OH or —$OR_{11}$; and
G and D are independently selected from hydrogen, $C_1$ to $C_{10}$ alkyl, —OH, —$OR_{11}$, —$CH_2OH$, —$CH_2OR_{11}$, —$CH_2OC(O)R_{21}$ wherein $R_{21}$ is as defined above, —$CH_2OC(O)CH(R_{22})(NHR_{23})$ wherein $R_{22}$ and $R_{23}$ are as defined above, —$CH_2SH$, —$CH_2Cl$, —$CH_2F$, —$CH_2Br$, —$CH_2I$, —C(O)H, —$CH_2CN$, —$CH_2N_3$, —$CH_2NR_{12}R_2$, —$CO_2R_1$, —$CH_2CH_2OH$, —$CH_2CH_2OR_{11}$, —$CH_2CH_2OC(O)R_{21}$ wherein $R_{21}$ is as defined above, —$CH_2CH_2OC(O)CH(R_{22})(NHR_{23})$ wherein $R_{22}$ and $R_{23}$ are as defined above, —$CH_2OPO_3H_2$, —$CH_2CH_2PO_3H_2$, —$CH_2PO_3H_2$, —$OCH_2PO_3H_2$ and —$CH_2CO_2R_3$ wherein $R_{12}$ is hydrogen, $C_1$ to $C_{10}$ alkyl, $R_3$ is hydrogen, $C_1$ to $C_{10}$ alkyl, carboxyalkyl or aminoalkyl, $R_{11}$ is $C_1$ to $C_6$ alkyl or a hydroxy protecting group, and $R_{13}$ is hydrogen or an N-protecting group; with the proviso that when E is —OH then D is not —OH.

Other useful intermediates for the preparation of the compounds of the invention include compounds of the formula:

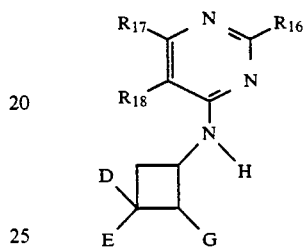

wherein
E is hydrogen, —$CH_2OH$, —$CH_2OR_{11}$, —OH or —$OR_{11}$;
G and D are independently selected from hydrogen, $C_1$ to $C_{10}$ alkyl, —OH, —$OR_{11}$, —$CH_2OH$, —$CH_2OR_{11}$, —$CH_2OC(O)R_{21}$ wherein $R_{21}$ is as defined above, —$CH_2OC(O)CH(R_{22})(NHR_{23})$ wherein $R_{22}$ and $R_{23}$ are as defined above, —$CH_2SH$, —$CH_2Cl$, —$CH_2F$, —$CH_2Br$, —$CH_2I$, —C(O)H, —$CH_2CN$, —$CN_2N_3$, —$CH_2NR_{12}R_2$, —$CO_2R_1$, —$CH_2CH_2OH$, —$CH_2CH_2OR_{11}$, —$CH_2CH_2OC(O)R_{21}$ wherein $R_{21}$ is as defined above, —$CH_2CH_2OC(O)CH(R_{22})(NHR_{23})$ wherein $R_{22}$ and $R_{23}$ are as defined above, —$CH_2OPO_3H_2$, —$CH_2CH_2PO_3H_2$, —$CH_2PO_3H_2$, —$OCH_2PO_3H_2$ and —$CH_2CO_2R_3$ wherein $R_{12}$ is hydrogen, $C_1$ to $C_{10}$ alkyl or an N-protecting group, $R_2$ is hydrogen or $C_1$ to $C_{10}$ alkyl, $R_3$ is hydrogen, $C_1$ to $C_{10}$ alkyl, carboxylakyl or aminoalkyl, $R_{11}$ is $C_1$ to $C_6$ alkyl or a hydroxy protecting group, and $R_{13}$ is an N-protecting group;
$R_{16}$ is hydrogen, —$NH_2$ or —OH;
$R_{17}$ is —OH or halogen; and
$R_{18}$ is —$NO_2$ or —$NH_2$; with the proviso that when E is —OH then D is not —OH.

Other useful intermediates for the preparation of the compounds of the invention include compounds of the formula:

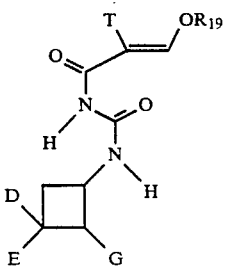

wherein

E is hydrogen, —CH$_2$OH, —CH$_2$OR$_{11}$, —OH or —OR$_{11}$;

G and D are independently selected from hydrogen, C$_1$ to C$_{10}$ alkyl, —OH, —OR$_{11}$, —CH$_2$OH, —CH$_2$R$_{11}$, —CH$_2$OC(O)R$_{21}$ wherein R$_{21}$ is as defined above, —CH$_2$OC(O)CH(R$_{22}$)(NHR$_{23}$) wherein R$_{22}$ and R$_{23}$ are as defined above, —CH$_2$SH, —CH$_2$Cl, —CH$_2$F, —CH$_2$Br, —CH$_2$I, —C(O)H, —CH$_2$CN, —CH$_2$N$_3$, —CH$_2$NR$_{12}$R$_2$, —CO$_2$R$_1$, —CH$_2$CH$_2$OH, —CH$_2$CH$_2$OR$_{11}$, —CH$_2$CH$_2$OC(O)R$_{21}$ wherein R$_{21}$ is as defined above, —CH$_2$CH$_2$OC(O)CH(R$_{22}$)(NHR$_{23}$) wherein R$_{22}$ and R$_{23}$ are as defined above, —CH$_2$OPO$_3$H$_2$, —CH$_2$CH$_2$PO$_3$H$_2$, —CH$_2$PO$_3$H$_2$, —OCH$_2$PO$_3$H$_2$ and —CH$_2$CO$_2$R$_3$ wherein R$_{12}$ is hydrogen, C$_1$ to C$_{10}$ alkyl or an N-protecting group, R$_2$ is hydrogen or C$_1$ to C$_{10}$ alkyl, R$_3$ is hydrogen, C$_1$ to C$_{10}$ alkyl, carboxyalkyl or aminoalkyl, R$_{11}$ is C$_1$ to C$_6$ alkyl or a hydroxy protecting group, and R$_{13}$ is an N-protecting group; and R$_{19}$ is C$_1$ to C$_6$ alkyl; with the proviso that when E is —OH then D is not —OH.

Other useful intermediates for the preparation of the compounds of the invention include compounds of the formula:

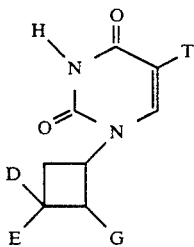

wherein

E is hydrogen, —CH$_2$OH, —CH$_2$OR$_{11}$, —OH or —OR$_{11}$;

G and D are independently selected from hydrogen, C$_1$ to C$_{10}$ alkyl, —OH, —OR$_{11}$, —CH$_2$OH, —CH$_2$OR$_{11}$, —CH$_2$OC(O)R$_{21}$ wherein R$_{21}$ is as defined above, —CH$_2$OC(O)CH(R$_{22}$NHR$_{23}$) wherein R$_{22}$ and R$_{23}$ are as defined above, —CH$_2$SH, —CH$_2$Cl, —CH$_2$F, —CH$_2$Br, —CH$_2$I, —C(O)H, —CH$_2$CN, —CH$_2$N$_3$, —CH$_2$NR$_{12}$R$_2$, —CO$_2$R$_1$, —CH$_2$CH$_2$OH, —CH$_2$CH$_2$OR$_{11}$, —CH$_2$CH$_2$OC(O)R$_{21}$ wherein R$_{21}$ is as defined above, —CH$_2$CH$_2$OC(O)CH(R$_{22}$)(NHR$_{23}$) wherein R$_{22}$ and R$_{23}$ are as defined above, —CH$_2$OPO$_3$H$_2$, —CH$_2$CH$_2$PO$_3$H$_2$, —CH$_2$PO$_3$H$_2$, —OCH$_2$PO$_3$H$_2$ and —CH$_2$CO$_2$R$_3$ wherein R$_{12}$ is hydrogen, C$_1$ to C$_{10}$ alkyl or an N-protecting group, R$_2$ is hydrogen or C$_1$ to C$_{10}$ alkyl, R$_3$ is hydrogen, C$_1$ to C$_{10}$ alkyl, carboxyalkyl or aminoalkyl, R$_{11}$ is C$_1$ to C$_6$ alkyl or a hydroxy protecting group, and R$_{13}$ is an N-protecting group; and T is hydrogen, C$_1$ to C$_{10}$ alkyl, 2-haloethyl, halomethyl, difluoromethyl, trifluoromethyl, halogen, cyano, nitro, vinyl, 2-halovinyl, alkynyl, hydroxmethyl, formyl, azidomethyl, 2-hydroxyethyl, —NR$_{12}$R$_2$ wherein R$_{12}$ and R$_2$ are as defined above, —NHOH, —SH, propenyl, 3,3,3-trifluoropropenyl, 2-(alkoxycarbonyl)ethenyl, 2-cyanoethenyl,

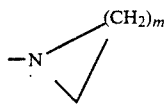

wherein m is 1 to 5, or —CH$_2$NR$_{12}$R$_2$ wherein R$_{12}$ and R$_2$ are as defined above; with the proviso that when E is —OH then D is not —OH.

The term "N-protecting group" as used herein refers to those groups intended to protect nitrogen atoms against undesirable reactions during synthetic procedures and includes, but is not limited to, acyl, acetyl, pivaloyl, t-butylacetyl, trichloroethoxycarbonyl, t-butyloxycarbonyl (Boc), benzyloxycarbonyl (Cbz) or benzoyl groups or other nitrogen protecting groups known to those skilled in organic synthesis such as those disclosed in Greene, "Protective Groups in Organic Synthesis", pp. 218-287, (J. Wiley & Sons, 1981).

The term "hydroxy protecting group" as used herein refers to those groups intended to protect a hydroxy group against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl and tetrahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; acyl groups such as acetyl and benzoyl; sulfonates such as mesylate and tosylate; or other hydroxy protecting groups known to those skilled in organic synthesis such as those disclosed in Greene, "Protective Groups in Organic Synthesis", pp. 10-71, (J. Wiley & Sons, 1981).

The following examples will serve to further illustrate preparation of the novel compounds of the invention.

EXAMPLE 1

9-(2',3'-Bis(hydroxymethyl)cyclobutyl)guanine

Step A:
1,2-bis(hydroxymethyl)-3-methylenecyclobutane

To a stirred solution of 40.0 g (0.188 mol) of 1,2-bis(ethoxycarbonyl-3-methylenecyclobutane (Cripps, H. N.; Williams, J. K.; Sharkey, W. H. J. Am. Chem. Soc. 1959, 81, 2723-2728) in 1.4 L of diethyl ether at 0° C. was added 14.4 g (0.379 mol) of lithium aluminum hydride in small portions. After 2 h at 0° C., 14.4 mL of H$_2$O, 14.4 mL of 15% aq. NaOH, and then 44.0 mL of H$_2$O were added sequentially. The resulting white solid was removed by filtration and washed thoroughly with diethyl ether. Concentration of the combined filtrates under reduced pressure afforded 17.1 g (71%) of the title compound as an oil, judged to be 95% pure by NMR: Rf 0.27 (silica gel, 1:1/acetone:hexane); IR (CDCl$_3$) cm−1; $^1$H NMR (CDCl$_3$) 1.66 (bs, 1H, OH), 2.24-2.41 (m, 2H), 2.44 (bs, 1H, OH), 2.57-2.71 (m, 1H), 2.87-2.96 (m, 1 H), 3.54, 3.58 (2 dd, 2H, J=J'=12 Hz, CH$_2$O), 3.79, 3.84 (2 dd, 2H, J=10.5 Hz, J'=4.5 Hz, CH$_2$O), 4.78, 4.82 (2 ddd, 2H, J=J'=J''=2.5 Hz, C=CH$_2$); $^{13}$C NMR (CDCl$_3$, CDCl$_3$=77.00 ppm)146.21, 105.39, 66.13, 63.74, 51.70, 38.67, 31.86; DCI- NH$_3$ MS, m/z 129 (M+1)+, 146 (M+NH$_4$+)+.

Step B: 2,3-Bis(hydroxymethyl)cyclobutanone

Through a solution of 15.0 g (0.117 mol) of the product from Step A of Example 1 in 872 mL of $CH_2Cl_2$ and 218 mL of MeOH at $-78°$ C. was passed a stream of ozone. When a persistent blue color appeared, the solution was purged with nitrogen and then treated with 68.0 mL (0.926 mol) of dimethyl sulfide. After 30 min, the reaction mixture was allowed to warm to room temperature and then concentrated under reduced pressure. Chromatography of the residue on 1 kg of silica gel with a hexane to 1:1/hexane:acetone gradient afforded 10.9 g (72%) of the title compound as an oil, judged to be 90% pure by NMR: Rf 0.17 (silica gel, 1:1/hexane:acetone); IR ($CDCl_3$) 3620, 3430, 2940, 2880, 1775, 1030 cm−1; $^1H$ NMR ($CDCl_3$) 1.61, 2.18 (2 bs, OH), 2.54 (ddddd, 1H, J=J′=J″=J‴=J⁗=8 Hz, J⁗′=5.5 Hz, H-3), 2.86, 2.99 (2 ddd, 2H, J=17 Hz, J′=8 Hz, J″=2.5 Hz, H-4) 3.36 (ddddd, 1H, J=J′=J″=8 Hz, J‴=J⁗=2.5 Hz) 3.74 (dd, 1H, J=11 Hz, J′=8 Hz, 3—CH HOH), 3.77-3.90 (m, 2H, 2—CH 2OH) 4.00 (dd, 1H, J=11 Hz, J′=5.5 Hz, 3—CHH OH); DCI-NH$_3$ MS, m/z 131 (M+1)$^+$, 148 (M+1+NH$_3$)$^+$.

Step C: 2,3-Bis(((1,1-dimethylethyl)dimethylsilyl)oxymethyl)-cyclobutanone O-Methyl Oxime To a stirred solution of 10.9 g (83.8 mmol) of the product from Step B from Example 1 in 88 mL of pyridine was added 7.70 g (92.2 mmol) of O-methylhydroxylamine hydrochloride. After 2 h at room temperature, 117 mL of pyridine and 40.0 g (265 mmol) of t-butyldimethylsilyl chloride was added. After 60 h at room temperature, the reaction mixture was concentrated under reduced pressure to a volume of 80 mL, diluted with 600 mL of $CH_2Cl_2$, washed with 100 mL of $H_2O$, dried over $MgSO_4$, and concentrated under reduced pressure. Chromatography of the residue on 1.25 kg of silica gel with a hexane to 97:3/hexane:acetone gradient afforded 24.9 g (77 %) of the title compound as an oil, judged by NMR to be a 1.5:1 mixture of geometrical isomers of 95% purity: Rf 0.68 (silica gel, 9:1/hexane-:acetone); IR ($CHCl_3$) 2950, 2930, 2890, 2850, 1675, 1470,1460, 1255, 1100, 1040, 1000 cm−1; $^1H$ NMR ($CDCl_3$) 0.04, 0.05 (2 s, 6 H, ($CH_3$)$_2$Si), 0.89 (s, 9 H, ($CH_3$)$_3$) 2.38-2.64 (m, 2 H), 2.71-2.89 (m, 1 H), 3.60-3.74 (m, 2 H), 3.78, 3.82 (2 s, 3 H, OCH$_3$), 3.78-3.95 (m, 2 H); DCI-NH$_3$ MS, m/z 388 (M+1+NH$_3$)$^+$.

Step D: 2,3-Bis(((1,1-dimethylethyl)dimethylsilyl)oxymethyl)-cyclobutylamine To a stirred suspension of 1.04 g (27.5 mmol) of NaBH$_4$ in 50 mL of dry THF was added dropwise over 5 min 2.12 mL (27.5 mmol) of trifluoroacetic acid. To this mixture was then added a solution of 2.30 g (5.94 mmol) of the product from Step C of Example 1 in 16.0 mL of THF. After 16 h at room temperature, the reaction mixture was diluted with 300 mL of $CH_2Cl_2$, washed with 100 mL of saturated aqueous NaCl, dried over MgSO$_4$, and concentrated under reduced pressure. Chromatography of the residue on 200 g of silica gel with a 95:5 to 90:10/$CH_2Cl_2$: MeOH gradient afforded 1.53 g (72%) of the title compound as an oil, judged to be 95% pure by NMR: Rf 0.65 (silica gel, 60:30:1/hexane:acetone:triethylamine); IR ($CDCl_3$) 3670, 3375, 2955, 2930, 2885, 2855, 1470, 1460, 180, 1360, 1255, 1195, 1095, 1060 cm−1; $^1H$ NMR ($CDCl_3$) 0.04 (s, 6 H, ($CH_3$)$_2$Si), 0.90 (s, 9 H, ($CH_3$)$_3$C), 1.38 (ddd, 1 H, J=11 Hz, J′=10 Hz, J″=9 Hz, H-4), 1.80-1.96 (m, 2 H, H-2 and H-3), 2.24 (ddd, 1 H, J=11 Hz, J=8 Hz, J′=7.5 Hz, H-4), 3.09 (ddd, 1 H, J=9 Hz, J′=J″=8 Hz, H-1), 3.56 (d, 2 H, J=4 Hz, CH$_2$O), 3.59, 3.69 (2 dd, 2 H, J=10.5 Hz, J′=4 Hz, CH$_2$O); DCI-NH$_3$ MS, m/z 360 (M+1)$^+$.

Step E: 2,3-Bis(hydroxymethyl)cyclobutylamine hydrochloride

To a stirred solution of 1.87 g (5.20 mmol) of the product from Step D of Example 1 in 66 mL of MeOH was added 1.60 mL (12.60 mmol) of trimethylsilyl chloride. After 1 h at room temperature, the reaction mixture was concentrated under reduced pressure. Evaporation of 3×10 mL of MeOH afforded 742 mg (85 %) of the title compound as an oil, judged to be 95% pure by NMR: Rf 0.02 (silica gel, $CH_2Cl_2$:MeOH:NH$_3$); $^1$NMR (CD$_3$OD) 1.82 (ddd, 1H, J=11 Hz, J′=J″=9 Hz, H-4), 2.16 (ddddd, 1 H, J=J′=J″=11 Hz, J‴=J⁗=5.5 Hz, H-3), 2.30-2.40 (m, 2 H, H-2, H-4), 3.49 (ddd, 1 H, J=J′=J″=9 Hz, H-1), 3.55, 3.60 (2 dd, 2 H, J=6 Hz, J′=4 Hz, CH$_2$O), 3.61, 3.65 (2 dd, 2 H, J=6 Hz, J′=4 Hz, CH$_2$O); DCI-NH$_3$ MS, m/z 132 (M+1)$^+$.

Step F: 3-((2′-Amino-6′-chloro-4′-pyrimidinyl)amino)-1,2-bis(-hydroxymethyl)cyclobutane To a stirred solution of 364 mg (2.18 mmol) of the product from Step E of Example 1 in 30 mL of EtOH was added 1.51 mL (10.8 mmol) of triethylamine and 536 mg (3.27 mmol) of 2-amino-4,6-dichloropyrimidine. After 26 h at reflux, the cooled reaction mixture was concentrated under reduced pressure. The residue was then desalted by passage through a 12 mL column of Dowex SBR (OH—) resin in 8:2/MeOH:H$_2$O and then concentrated under reduced pressure. Chromatography of the residue on 40 g of silica gel with a 90:10 to 85:15/$CH_2Cl_2$ gradient afforded 294 mg (52%) of the title compound, judged to be 95% pure by NMR: Rf 0.29 (silica gel, 85:15/$CH_2Cl_2$:MeOH); $^1H$ NMR (CD$_3$OD) 1.64 (ddd, 1H, J=J′=J″=10 Hz, H-4), 1.90-2.03 (m, 1 H), 2.0-2.15 (m, 1 H), 2.37 (ddd, 1 H, J=10 Hz, J′=J″=8 Hz, H-4), 3.52, 3.57 (2 dd, 2 H, J=12 Hz, J′=7 Hz, CH$_2$O), 3.59, 3.66 (2dd, 2 H, J=12 Hz, J′=7 Hz, CH$_2$O), 3.90-4.02 (bm, 1 H, H-1), 5.82 (s, 1 H, H-5′); DCI-NH$_3$ MS, m/z 259, 261 (M+1)$^+$.

Step G: 3-((6′-Chloro 2′,5′-diamino-4′-pyrimidinyl)amino)-1,2-bis(hydroxymethyl)cyclobutane To a stirred solution of 294 mg (1.14 mmol) of the product from Step F of Example 1 and 2.00 g (14.69 mmol) of sodium acetate trihydrate in 5.0 mL of acetic acid and 5.0 mL of water was added over 30 min a cold (0°-5° C.) solution of 4-chlorobenzenediazonium chloride (prepared from 160 mg (1.25 mmol) of 4-chloroaniline, 1.2 mL of water, 0.35 mL of 12N HCl, and 95 mg (1.51 mmol) of sodium nitrite in 1.2 mL of water). After 17 h at room temperature, the yellow precipitate was collected by filtration, washed with cold water, and dried under vacuum to afford 343 mg of the 5′-((4″-chlorophenyl)azo) derivative. Without further purification, this azo compound was dissolved in 7.4 mL of ethanol, 7.4 mL of water, and 0.74 mL of acetic acid at 75° C. and treated with 221 mg (3.38 mmol) of zinc dust. After 1.5 h, the reaction mixture was allowed to cool, filtered, the solids washed with ethanol, and the combined filtrates concentrated under reduced pressure. Chromatography of the residue on 30 g of silica gel with a $CH_2Cl_2$ to 85:15/$CH_2Cl_2$:MeOH gradient afforded 176 mg (56%) of the title compound, judged to be 95% pure by NMR: Rf 0.29 (silica gel 85:15/$CH_2Cl_2$:MeOH); $^1$H NMR ($CD_3OD$) 1.77 (ddd, 1 H, J=11 Hz, J'=J"=9 Hz, H-4), 1.92–2.04, 2.10–2.20 (2 m, 2 H, H-1, H-2), 2.41 (ddd, 1 H, J=11 Hz, J'=8 Hz, J'=7.5 Hz, H-4), 3.54, 3.60 (2 dd, 2 H, J=12 Hz, J'=6 Hz, $CH_2O$), 3.62, 3.68 (2 dd, 2 H, J=12 Hz, J'=7 Hz, $CH_2O$), 4.40 (ddd, 1 H, J=J'=J"=9 Hz, H-3); DCI-$NH_3$ MS, m/z 274 (M+1)$^+$.

Step H:
3-(2'-Amino-6'-chloro-9'H-purin-9'-yl)-1,2-bis(hydroxymethyl)cyclobutane A solution of 171 mg (0.625 mmol) of the product from Step G of Example 1 in 20 mL of diethoxymethyl acetate was heated to reflux. After 22 h, the reaction mixture was allowed to cool and then concentrated under reduced pressure. To a solution of the residue in 30 mL of toluene was added 6.5 mg of p-toluenesulfonic acid. After 1.0 h at room temperature, the reaction mixture was concentrated under reduced pressure and then dissolved in 7.0 mL of methanol saturated with $NH_3$ at 0° C. After 1 h at room temperature, the reaction mixture was concentrated under reduced pressure and then co evaporated with 3×3 mL of MeOH. To a solution of the residue in 12.0 mL of MeOH was added p-toluenesulfonic acid until the apparent pH of the reaction mixture was 3, as judged by spotting the reaction mixture on wet pH paper. After 1 h at room temperature, the reaction mixture was neutralized with $NH_3$ saturated MeOH and concentrated under reduced pressure. Chromatography of the residue on 25 g of silica gel with a 95:5 to 85:15/$CH_2Cl_2$:MeOH gradient afforded 74 mg (42%) of the title compound as a white amorphous solid, judged to be 95% pure by NMR: Rf 0.30 (silica gel, 85:15/$CH_2Cl_2$ MeOH); $^1$H NMR ($CD_3OD$) 2.17–2.27, 2.85–2.94 (2 m, 2 H, H-1, H-2), 2.89 (ddd, 1 H, J=11 Hz, J'=J"=9 Hz, H-4), 2.55 (ddd, 1 H, J=11 Hz, J'=8 Hz, J"=7 Hz, H-4), 3.64–3.74 (m, 4 H, 2 $CH_2O$), 4.64 (ddd, 1H, J=J'=9 Hz, J"=8 Hz, H-3), 8.19 (s, 1 H, H-8'); DCI-$NH_3$ MS, m/z 284, 286 (M+1)$^+$.

Step I: 9-(2',3'-Bis(hydroxymethyl)cyclobutyl)guanine

A solution of 70 mg (0.247 mmol) of the product from Step H of Example 1 in 7.0 mL of 1N HCl was heated to reflux for 5 h, allowed to cool, concentrated under reduced pressure, and then coevaporated with 3×5 mL of EtOH. The residue was dissolved in 1 mL of $H_2O$, neutralized with 15N aqueous $NH_3$, and then concentrated under reduced pressure. Trituration of the residue with 1 mL of hot EtOH, decantation, and drying under vacuum afforded 59 mg (90%) of the title compound as an amorphous white solid: Rf=0.28 (silica gel, 6:4/$CH_2Cl_2$:MeOH); $^1$H NMR ($D_2O$, TSP=0.00 ppm) 2.17 (ddd, 1 H, J=J'=10 Hz, J"=9 Hz, H-4'), 2.16–2.28, 2.58–2.66, 2.69–2.78 (3 m, 3 H, H-4', H-2', H-3'), 3.72, 3.74 (2 d, 4 H, J=6 Hz, 2 $CH_2O$), 4.51 (ddd, 1 H, J=J'=J"=9 Hz, H-1') 7.97 (s, 1 H, H-8); DCI-$NH_3$ MS, m/z 266 (M+1)$^+$.

Alternate Procedure

Step J:
3-((2'-Amino-3,'4'-dihydro-5'-nitro-4'-oxo-6'-pyrimidinyl)-amino)-1,2-bis((1,1-dimethylethyl)dimethylsilyl)oxymethyl)cyclobutane A solution of 3.00 g (8.34 mmol) of the product from Step D of Example 1, 1.84 mL (12.5 mmol) of triethylamine, and 1.58 g (8.29 mmol) of 6-chloro-3,4-dihydro-5-nitro-4-oxopyrimidine (Temple, C.; Smith, B. H.; Montgomery, J. A. J. Org. Chem. 1975, 40, 3141–3142) in 20 mL of dry DMF was heated under nitrogen at 50° C. After 3 h, the cooled reaction mixture was poured into 500 mL of ether, washed with 250 mL of $H_2O$, dried over $MgSO_4$ and then concentrated under reduced pressure. Chromatography of the residue on 300 g of silica gel with a 100:0 to 95:5/$CH_2Cl_2$:MeOH gradient afforded 2.40 g (56%) of the title compound as a yellow glass, judged to be 95% pure by NMR: Rf 0.48 (silica gel, 9:1/$CH_2Cl_2$:MeOH); $^1$H NMR ($CDCl_3$) 0.04, 0.05 (2 s, 12 H, 2 ($CH_3)_2$Si), 0.90, 0.91 (2 s, 18 H, 2 ($CH_3)_3$Si), 1.71 (ddd, 1 H, J=11 Hz, J'=J"=9 Hz, H-4), 2.08–2.20 (m, 1 H, H-1), 2.30 (dddd, 1 H, J=J'=9 Hz, J"=J'"=5 Hz, H-2), 2.39 (ddd, 1 H, J=11 Hz, J'=J"=8 Hz, H-4), 3.56–3.74 (m, 4 H, 2 $CH_2O$), 4.45 (dddd, 1 H, J=J'=9 Hz, J"=J'"=8 Hz, H-3), 1.57, 5.24, 8.40 (3 bs, 3 H, NH, $NH_2$), 9.74 (d, 1 H, J=8 Hz, NH); DCI $NH_3$ MS, m/z 484 (M+H)$^+$.

Step K: 9-(2',3'-Bis(hydroxymethyl)cyclobutyl)guanine

A stirred solution of 2.40 g (4.67 mmol) of the product from Step J of Example 1 in 190 mL of 96% formic acid (remainder $H_2O$) was degassed with argon and then treated with 12.0 g (184 mmol) of zinc dust (325 mesh) at room temperature. After 1.5 h at room temperature, the reaction mixture was filtered through a medium glass frit, concentrated to 25 mL, transferred to a steel bomb, degassed with a stream of argon, sealed, and then heated with stirring at 180° C. A small amount of white precipitate quickly dissolved and the reaction mixture became pale yellow. After 2.5 h, the reaction mixture was cooled in an ice bath, carefully vented, and then concentrated under reduced pressure. Residual formic acid was removed by coevaporation with $H_2O$ until the pH was 4. The resulting solid was suspended in 50 mL of $H_2O$, removed by filtration, dried in vacuo to a weight of 1.1 g, dissolved in 20 mL of 15 M $NH_4OH$, concentrated under reduced pressure, and then coevaporated with 10 ml of $H_2O$ to afford 940 mg of a pale yellow solid. This material was suspended in 15 mL of EtOH, heated to 80° C., cooled to 0° C., and then filtered to afford 347 mg of a pale yellow solid. The mother liquor was concentrated under reduced pressure, and the gummy yellow residue was crystallized from $H_2O$ and washed with acetone to afford 353 mg of an off white solid. This material was combined with the previous crop, dissolved in 30 mL of $H_2O$ at 60° C., treated with 550 mg of Darco G-60 charcoal for 2 min, and filtered through a 0.45 micron filter. The charcoal was washed with 3×10 mL of $H_2O$ at 60° C. and the combined filtrates were concentrated under reduced pressure, crystallized from $H_2O$ (ca. 50 mg/mL), washed with acetone, and dried at 60° C. under vacuum to afford 550 mg (44%) of the title compound as a white powder. This material was identical by TLC and $^1$H NMR to the product of Step I of Example 1.

EXAMPLE 2

1-(2',3'-Bis(hydroxymethyl)cyclobutyl)uracil

Step A:
N-((2,3-Bis((1,1-dimethylethyl)dimethylsilyl)oxymethyl)cyclobutyl)urea To a stirred solution of 950 mg (2.64 mmol) of the product from Step D of Example 1 in 50 mL of dry THF was added 0.84 mL (5.34 mmol) of trimethylsilyl isocyanate (85%, remainder hexamethyldisiloxane) and 0.74 mL (5.30 mmol) of triethylamine. After 16 h at reflux, 0.42 mL (2.67 mmol) of trimethylsilylisocyanate and 0.37 ml (2.65 mmol) of triethylamine were added. After a total of 40 h at reflux, 0.84 mL (5.34 mmol) of trimethyl isocyanate and 0.74 (5.30 mmol) of triethylamine were added. After a total of 80 h at reflux, the cooled reaction mixture was concentrated under reduced pressure. Chromatography of the residue on 50 g of silica gel with a 95:5 to 85:15/$CH_2Cl_2$:MeOH gradient afforded 825 mg (78%) of the title compound as an oil judged by NMR to be 90% pure: Rf 0.17 (silica gel, 60:30:1/hexane:acetone:triethylamine); $^1$H NMR ($CDCl_3$) 0.04, 0.06 (2 s, 12 H, 2 $(CH_3)_2Si$)), 0.90 (s, 18 H, 2 $(CH_3)_3C$), 1.54 (ddd, 1 H, J=11 Hz, J'=J"=9 Hz, H 4), 1.80–1.92, 2.09–2.18 (2 m, 2 H, H-2, H-3), 2.35 (ddd, 1 H, J =11 Hz, J=J'=9 Hz), 3.52 (dd, 1 H, J=10 Hz, J'=6 Hz, CH HO), 3.54–3.67 (m, 3 H, H-1, 2 CH HO), 3.75 (dd, 1 H, J=11 Hz, J'=5 Hz), 4.56 (bd, 1 H, J=6 Hz, NH), 4.90 (bs, 2 H, $NH_2$); DCI-$NH_3$ MS, m/z 403 $(M+1)^+$.

Step B: 1-(2,'3'-Bis(hydroxymethyl)cyclobutyl)uracil

To a stirred solution of 401 mg (0.996 mmol) of the product from Step A of Example 2 in 15 mL of pyridine was added 200 uL (1.50 mmol) of (E )-3-ethoxyacryloyl chloride. After 5 h at room temperature, the reaction mixture was concentrated under reduced pressure. Chromatography of the residue on 50 g of silica gel with a 5:0 to 5:1/hexane:acetone gradient afforded 273 mg (54%) of N-(N'-(2',3'-Bis((1,1-dimethylethyl)dimethylsilyl)oxymethyl)cyclobutyl)carbamoyl)-3-ethoxypropenamide as a colorless oil, judged to be 85% pure by TLC: Rf 0.53 (60:30:1/hexane:acetone:triethylamine); DCI- $NH_3$ MS, m/z 501 $(M+1)+$. Without further purification, 273 mg (0.545 mmol) of this propenamide was dissolved in 16.3 mL of 2 M $H_2SO_4$ and heated to reflux. After 1.5 h, the solution was allowed to cool, the pH adjusted to 6 with solid $NaHCO_3$, the solution saturated with NaCl, and then continuously extracted with EtOAc for three days. The organic extract was dried over $MgSO_4$ and concentrated under reduced pressure. Chromatography of the residue on 10 g of silica gel with a 9:1 to 8:2/$CH_2Cl_2$:MeOH gradient afforded 67 mg (54%, 24% overall) of the title compound as an amorphous solid judged by NMR to be greater than 95% pure: Rf 0.35 (silica gel, 80:20/$CH_2Cl_2$:MeOH); $^1$H NMR ($CDCl_3$, TSP=0.00 ppm) 1.97 (ddd, 1 H, J=J'=J"=11 Hz, H-4'), 2.08–2.20 (m, 1 H, H-3'), 2.47 (ddd, 1 H, J=11 Hz, J'=J"=8 Hz, H-4'), 2.59 (dddd, 1 H, J=J'=9 Hz, J"=J'''=6 Hz, H-2'), 3.62–3.74 (m, 4 H, 2 $CH_2O$), 4.57 (ddd, 1 H, J=J'=J"=9 Hz, H-1'), 5.87 (d, 1 H, J=8 Hz, H-5), 7.84 (d, 1H, J=8 Hz, H 6); FAB MS, m/z 227 $(M+1)^+$.

EXAMPLE 3

1-(2',3'-Bis(hydroxymethyl)cyclobutyl)cytosine

To 95 mg (0.42 mmol) of the product from Step B of Example 2 was added 440 microliters (2.1 mmol) of hexamethyldisilazane and 34 microliters (0.82 mmol) of formamide and the resulting mixture was heated with stirring in a sealed tube at 140° C. After 85 h, 10 mL of MeOH was added to the cooled reaction mixture, the tube resealed, and heated at 65° C. After 3 h, the cooled reaction mixture was concentrated under reduced pressure, dissolved in 10 mL of water, treated with 50 mg of Darco G-60 charcoal, filtered, and concentrated under reduced pressure. Chromatography of the residue on 15 g of silica gel with a 10:0 to 7:3/$CH_2Cl_2$:MeOH gradient afforded 68 mg (72%) of the title compound as an amorphous solid, judged by NMR to be 95% pure: Rf 0.27 (silica gel, 7:3/$CH_2Cl_2$:MeOH); $^1$H NMR ($D_2O$, TSP=0.00 ppm) 1.90 (ddd, 1 H, J=J'=J"=10 Hz, H-4'), 2.06–2.19 (m, 1 H, H- 3'), 2.44–2.58 (m, 2 H, H-2', H-4'), 3.64–3.71 (m, 4 H, 2 $CH_2O$), 4.52 (ddd, 1 H, J=10 Hz, J=J'=9 Hz, H-1'), 6.03 (d, 1 H, J=7.5 Hz, H-5), 7.79 (d, 1 H, J=7.5 Hz, H-6); FAB MS, m/z 226 $(M+1)^+$, 248 $(M+Na)^+$.

EXAMPLE 4

9-(2',3'-Bis(hydroxymethyl)cyclobutyl)adenine

Step A:
3-((5'-Amino-6'-chloro-4'-pyrimidinyl)amino)-1,2-bis(hydroxymethyl)cyclobutane A solution of 382 mg (2.28 mmol) of the pruduct from Step E of Example 1, 558 mg (3.4 mmol) of 5-amino-4,6-dichloropyrimidine, and 1.59 mL (11.4 mmol) of triethylamine in 25 mL of n-butanol was heated to reflux. After 20 h, 0.30 mL (2.15 mmol) of triethylamine was added, and after 5 h more at reflux, the cooled reaction mixture was concentrated under reduced pressure, passed through a column containing 12 mL of Dowex SBR (OH—) resin in 8:2/MeOH:$H_2O$, and then concentrated under reduced pressure. Chromatography of the residue on 50 g of silica gel with a 100:0 to 85:15/$CH_2Cl_2$:MeOH gradient afforded 384 mg (65%) of the title compound, judged to be 95% pure by NMR: Rf 0.33 (silica gel, 85:15/$CH_2Cl_2$:MeOH); $^1$H NMR ($CD_3OD$) 1.76 (ddd, 1 H, J=11 Hz, J'=J"=9 Hz, H-4), 1.95–2.08 (m, 1 H, H-1), 2.16–2.26 (m, 1 H, H-2), 2.46 (ddd, 1 H, J =11 Hz, J'=J"=9 Hz, H-4), 3.55, 3.61 (2 dd, 2 H, J=11 Hz, J'=6 Hz, $CH_2O$), 3.63, 3.70 ( 2 dd, 2 H, J=11 Hz, J'=7 Hz, $CH_2O$), 4.12 (ddd, 1 H, J=J'=J"=9 Hz, H 1), 7.76 (s, 1 H, H-2'); DCI-$NH_3$ MS, m/z 259, 261 $(M+H)^+$.

Step B:
3-(6'-chloro-9'H-purin-9'-yl)-1,2-bis(hydroxymethyl)cyclobutane

A solution of 352 mg (1.36 mmol ) of the product from Step A of Example 4 in 25 mL of diethoxymethyl acetate was heated to reflux. After 16 h, the cooled solution was concentrated under reduced pressure. To a solution of the residue in 27 mL of toluene was added 13.6 mg of p-toluenesulfonic acid. After 1 h at room temperature, the reaction mixture was concentrated under reduced pressure and then dissolved in 30 mL of MeOH which had been saturated at room temperature with $NH_3$. After 1 h at room temperature, the reaction mixture was concentrated under reduced pressure and coevaporated with 3×5 mL of MeOH. To a solution of the residue in 25 mL of MeOH was added p-toluenesulfonic acid until the pH appeared to be 3 by spotting the reaction mixture on moist pH paper. After 1.5 h at room temperature, the reaction mixture was neutralized with NH$_3$ saturated MeOH and then concentrated under reduced pressure. Chromatography of the residue on 25 g of silica gel with a 95:5 to 85:15/CH$_2$Cl$_2$:MeOH gradient afforded 254 mg (70%) of the title compound, judged to be 93% pure by NMR: Rf 0.34 (silica gel, 85:15/CH$_2$Cl$_2$:MeOH); $^1$H NMR (CD$_3$OD) 2.20-2.33 (m, 1 H, H-1), 2.49 (ddd, 1 H, J=11 Hz, J'=J''=9 Hz, H-4), 2.64 (ddd, 1 H, J=11 Hz, J'=J''=9 Hz, H-4), 3.01 (dddd, 1 H, J =J'=9 Hz, J''=J'''=6 Hz, H-2), 366-3.78 (m, 4 H, 2 CH$_2$O), 4.88 (ddd, 1 H, J=J'=J''=9 Hz, H-1), 8.68, 8.73 (2 s, 2 H, H-2 and H-8); DCI NH$_3$ MS, m/z 269, 271 (M+H)$^+$.

Step C: 9-(2,'3'-Bis(hydroxymethyl)cyclobutyl)adenine

A solution of 102.5 mg (0.38 mmol) of the product from Step B of Example 4 in 3 mL of MeOH and 5 mL of liquid NH$_3$ was heated at 60° C. in a sealed tube. After 48 h, the reaction mixture was cooled to −78° C. and the tube was opened. After the NH$_3$ had evaporated, the reaction mixture was concetrated under reduced pressure. Crystallization of the residue from 0.7 mL of MeOH afforded 75 mg (79%) of the title compound with m.p. 179°-182° C. Recrystallization of a portion of this material raised the m.p. to 181°-183° C.: Rf 0.19 (silica gel, 8:2/CH$_2$Cl$_2$:MeOH); $^1$H NMR (D$_2$O, TSP=0.00 ppm) 2.21 (ddd, 1 H, J=J'=10 Hz, J''=9 Hz, H-4'), 2.21-2.36 (m, 1 H, H-3'), 2.70 (ddd, 1 H, J=10 Hz, J'=J''=8 Hz, H-4'), 2.80 (dddd. 1 H, J=J'=9 Hz, J''=J'''=5 Hz, H-2'), 3.75, 3.77 (2 d, 4 H, J=5 Hz, 2 CH$_2$O), 4.66 (ddd, 1 H, J=J'=9 Hz, J''=8 Hz, H-1'), 8.14, 8.27 (2 s, 2 H, H-2 and H-8); DCI NH$_3$ MS, m/z 250 (M+H)$^+$; FAB MS, m/z 250 (M+H)$^+$; exact mass calcd for C$_{11}$H$_{16}$N$_5$O$_2$ (M+H)$^+$ 250.1304, found 250.1303.

EXAMPLE 5

9-((3'-Hydroxymethyl)cyclobutyl)guanine

Step A:
N-(Benzyloxycarbonyl-3-methylenecyclobutanamine

To a stirred solution of 26.7 g (238 mmol) of 3-methylenecyclobutane carboxylic acid (Cripps, H. N.; Williams, J. K.; Sharkey, W. H. J. Am. Chem. Soc. 1959, 81, 2723-2728) in 100 mL of toluene at 0° C. was added 36.4 mL (262 mmol) of triethylamine and then 72.1 g (262 mmol) of diphenylphosphoryl azide. The reaction mixture was then heated at 80° C., and after 1 h, 28.33 g (262 mmol) of benzyl alcohol was added. After 15 h at 85° C., the cooled reaction mixture was poured into 1 L of ether, washed with saturated aqueous NaHCO$_3$, and then saturated aqueous NaCl, dried over MgSO$_4$, and then concentrated under reduced pressure. Chromatography of the residue in three portions on 1400 g of silica gel with 80:20/hexane:EtOAc afforded 35.4 g (63%) of the desired compound.

MS DCI/NH$_3$ M?Z: 218 (M+H)$^+$, 235 (M+NH$_4$)$^+$; $^1$H NMR (CDCl$_3$) 2.60 (m, 2H), 3.05 (m, 2H), 4.20 (m, 1H), 4.83 (m, 2H), 5.21 (s, 2H), 7.45 (m, 5H).

Step B:
3-((N-benzyloxycarbonyl)amino)cyclobutanemethanol

To a stirred solution of 17.47 g (80.5 mmol) of the product from Step A of Example 5 in 25 mL of THF was added 145 mL (145 mmol) of 1M BH$_3$ in THF.

After 2 h at room temperature, 80 mL of 6N aqueous NaOH was added. After the vigorous release of H$_2$ had subsided, 22 mL of 30% H$_2$O$_2$ was then added. After 45 min, solid K$_2$CO$_3$ was added. After the reaction mixture had stirred for an additional 30 min, the reaction mixture was filtered through celite, diluted with 500 mL of EtOAc, washed with saturated aqueous NaCl, dried over Na$_2$SO$_4$, and then concentrated under reduced pressure. Chromatography of the residue on 1200 g of silica gel with a 1:1 to 9:1 ethyl acetate/hexane gradient afforded 12.01 g (63.5%) of the desired compound.

Step C: 3-Amino-cyclobutanemethanol

A stirred solution of 12.01 g (51.1 mmol) of the product from Step B of Example 5 in 200 mL of MeOH was hydrogenated over 1.2 g of 20% Pd/C, filtered, and then concentrated under reduced pressure to afford 4.98 g (96%) of the desired compound.

Step D:
3-((2'-Amino6'-chloro-4'-pyrimidinyl)amino)cyclobutanemethanol

A solution of 4.98 g (49.3 mmol) of the product from Step C of Example 5, 16.17 g (98.6 mmol) of 2-amino-4,6-dichloropyrimidine, and 6.36 mL (49.3 mmol) of triethylamine in 40 mL of 2-methoxyethanol was heated to reflux. After 2 h, the reaction mixture was allowed to cool, diluted with 100 mL of dichloromethane, and filtered. The filtrate was then concentrated under reduced pressure, triturated with 100 mL of 10% isopropanol in EtOAc, filtered, and then concentrated under reduced pressure. Chromatography of the residue on 500 g of silica gel with a 95:5 to 90:10/EtOAc: isopropanol gradient afforded 7.10 g (63%) of the desired compound: Rf 0.50 (silica gel, 90:10/EtOAc:isopropanol); DCI NH$_3$ MS, m/z 229, 231 (M+H)$^+$.

Step E:
3-((6'-Chloro-2,'5'-diamino-4'-pyrimidinyl)amino)-cyclobutanemethanol

Following the procedure of Step G of Example 1, but substituting 4.762 g (37.3 mmol) of the product from Step D of Example 5 for the product from Step F of Example 1, afforded, after purification of the crude product by chromatography on 500 g of silica gel with 90:10/EtOAc: isopropanol, 1.22 g (27%) of the desired compound: Rf 0.43 (silica gel, 9:1/EtOAc: isopropanol); DCI NH$_3$ MS, m/z 244, 246 (M+H)$^+$.

Step F:
3-(2'-Amino-6'-chloro-9'H-purin-9'-yl)cyclobutanemethanol

To a stirred solution of 1.22 g (5.37 mmol) of the product from Step E of Example 5 in 10 mL of DMF at 0° C. was added a solution of 0.50 mL of concentrated aqeuous HCl in 10 mL of triethyl orthoformate. The solution was allowed to gradually warm to room temperature. After 15 h, the reaction mixture was concentrated under reduced pressure and then coevaporated with 3×10 mL of water. The residue was dissolved in 50 mL of 50% aqueous HOAc. After 5 h, the reaction mixture was concentrated under reduced pressure. The residue was dissolved in 50 mL of 10% NH$_3$ in MeOH. After 4 h, the reaction mixture was concentrated under reduced pressure. Chromatrography of the residue on 150 g of silica gel with 85:15/CH$_2$Cl$_2$:MeOH afforded 1.018 g (75%) of the desired compound: Rf 0.26 (silica gel, 90:10/CH$_2$Cl$_2$:MeOH); DCI NH$_3$ MS, m/z 254, 256 (M+H)+.

Step G: 9-(3'-(Hydroxymethyl)cyclobutyl)guanine

A solution of 1.018 g (4.02 mmol) of the product from Step F of Example 5 in 30 mL of 1N HCl was heated to reflux for 5 h and then concentrated under reduced pressure. The residue was dissolved in a small amount of water and the pH was adjusted to 7 with 1N NaOH. The resulting precipitate was removed by filtration, redissolved in MeOH, filtered, and then concentrated under reduced pressure and dried in vacuo to afford 666 mg (70%) of the desired compound as a white powder: Rf 0.21 (silica gel, 80:20:1/CH$_2$Cl$_2$MeOH:NH$_3$); DCI NH$_3$ MS, m/z 236 (M+H)+.

EXAMPLE 6

3-(2',6'-Diamino-9'H-purin-9'-yl)-1,2-bis(hydroxymethyl)cyclobutane

To a solution of 100 mg (0.272 mmol) of the product of Example 22 in 5 ml of EtOH was aded 10 ml of liquid ammonia and the resulting mixture was heated at 100° C. in a steel bomb. After 15 hours, the reaction mixture was allowed to cool, the ammonia allowed to evaporate and the remaining solution was concentrated under reduced presure. Chromatography of the residue on 10 g of C-18 bonded silica gel with a 100:0 to 60:40/water:methanol gradient afforded 45.6 mg (64%) of the title compound as a white solid. $^1$H NMR (D$_2$O, TSP=0.00 ppm) 2.16 (ddd, 1H, J=J'=J"=9Hz, H-4), 2.14-2.30 (m, 1H), 2.60-2.75 (m, 2 H), 3.68-3.80)m, 4 H, 2 CH$_2$O), 4.48 (ddd, 1 H, J=J'=J"=9 Hz, H-3), 7.98 (s, 1 H, H-8'); FAB MS, m/z 265 (M+H).

EXAMPLE 7

3-(2'-Amino-9'H-purin-9'-yl)-1,2-bis(hydroxymethyl)-cyclobutane

To a solution of the product of Example 24 in 50 mL of MeOH was added 5 mL of concentrated NH$_4$OH. After 24 hours, the solution was concentrated under reduced pressure. Chromatography of the residue on silica gel with 95:5 to 60:40 gradient of CHCl$_3$/MeOH afforded 480 mg of the tiltle compound. Analysis calculated for C$_{11}$H$_{15}$N$_5$O$_2$ 0.1 H$_2$O: C, 52.62; H, 6.10: N, 27.89. Found: C, 52.80; H, 6.14; N, 27.73. DCI/NH$_3$ MS, m/z 250 (M+H)+.

EXAMPLE 8

3-(6'-Chloro-9'H-purin-9'-yl)cyclobutylmethanol

Step A: 3-((N-t-butyloxycarbonyl)amino)methylenecyclobutane

In a round bottom flask were placed 5.0 g of 3-methylenecyclobutane carboxylic acid (see Step A of Example 5) and 75 mL of t-butylalcohol. To the system were added 10.6 mL of diphenylphosphoryl azide and 6.8 mL of triethylamine. The reaction mixture was heated at reflux for 14 h, concentrated, and diluted with ether. This solution was washed with aqueous phosphoric acid, aqueous sodium bicarbonate, and brine, and then dried over sodium sulfate. The crude material was purified by chromatography to afford 4.0 g of the desired compound.

Step B: 3-((N-t-butyloxycarbonyl)amino)cyclobutanemethanol

In a round bottm flask were placed 3.85 g of the product from Step A of Example 8 and 10 mL of THF. To the system, at 0° C., was added 42 mL of 1M BH3 in THF. The reaction mixture was stirred at 0° C. for 30 min and room temperature for 3 h. Then 10 mL of 1M BH3 in THF was added to the system, and the mixture was stirred at room temperature for 1 h. The system was cooled to 0° C., and 26 mL of 6M aqueous NaOH was cautiously added to the system followed by 7.7 mL of 30% H$_2$O$_2$. The mixture was stirred at room temperature overnight. To the system was added solid K$_2$CO$_3$ followed by ethyl acetate and water. The layers were separated, and the organic layer was washed with aqueous phosphoric acid, aqueous sodium bicarbonate, and brine, and then dried and concentrated. The crude material was purified by column chromatography to afford 2.1 g of the desired compound.

Step C: 3-(Hydroxymethyl)cyclobutylamine hydrochloride

In a round bottom flask were placed 0.94 g of the product from Step B of Example 8 and 19 mL of 4M HCl in 1:2 H$_2$O/THF, and this solution was stirred at room temperature for 1 h and then concentrated to afford the desired compound.

Step D: 3-((5'-Amino-6'-chloro-4'-pyrimidinyl)amino)cyclobutanemethanol

In a round bottom flask were placed the crude material from Step C of Example 8, 10.8 mL of n-butanol, 2.7 mL of triethylamine, and 1.55 g of 5-amino-4,6-dichloropyrimidine. The mixture was heated at 120° C. for 10 h, concentrated, and purified by column chromatography to afford 923 mg of the desired compound: m.p. 152°-156° C.

Step E: 3-(6'-chloro-9'H-purin-9'-yl)cyclobutanemethanol

In a round bottom flask were placed 0.86 g of the product from Step D of Example 8, 10 mL of triethylorthoformate, 5 mL of N-methylpyrrolidinone, and 0.5 mL of concentrated HCl. The reaction mixture was stirred at room temperature for 1.5 h, 0.2 mL more HCl and 2 mL more of triethylorthoformate were added, and after a total of 3 h, the reaction mixture was concentrated. Flash chromatography afforded 0.33 g of the desired compound as a light yellow oil. Also isolated was 200 mg of 6-chloro-9-(3'-formyloxymethylcyclobutyl)purine.

EXAMPLE 9

3-(6'-Chloro-9'H-purin-9'-yl)-N-butyloxycarbonylaminomethylcyclobutane

Step A: N-t-butyloxycarbonyl-1-aminomethyl-3-methylenecyclobutane

In a round bottom flask were placed 10 g of 1-aminomethyl-3-methylenecyclobutane (Caserio, F. F.; Parker, S. H.; Piccolini, R.; Roberts, J. D. J. Am. Chem. Soc. 1958, 80, 5507-5513) and 80 mL of dichloromethane. To this solution, at 0° C., were added 43.4 mL of triethylamine followed by 24.5 g of di-t-butyl dicarbonate over a period of 20 min. The reaction mixture was stirred for 3 days, washed with aqueous phosphoric acid, saturated aqueous sodium bicarbonate and brine, dried, and then concentrated to afford 19.7 g of the title compound.

Step B:
N-t-Butoxycarbonyl-3-aminomethylcyclobutanone

In a round bottom flask were placed 9 g of the product from Step A of Example 9, 100 mL of methanol, and 400 mL of dichloromethane. The solution was cooled to −78° C., and ozone was bubbled through the reaction mixture until the solution was blue. The system was flushed with nitrogen for 2.5 h, and then treated with 34 mL of dimethylsulide. After 1 h at −78° C., 0° C. for 1 h, and room temperature for 1 h, the solution was stored in a refrigerator at 5° C. overnight before being concentrated. The crude material was purified by column chromatography to afford the title compound.

Step C:
N-t-butyloxycarbonyl-3-aminomethylcyclobutanamine

In a round bottom flask were placed 4 g of the product from Step B of Example 9 and 12 mL of methanol. In a separate flask were placed 1.46 g of hydroxylamine hydrochloride, 18 mL of water, and 1.76 g of sodium bicarbonate. The resulting solution was added to the intitial flask, and the resulting mixture was stirred at room temperature for 3 h. The reaction mixture was then diluted with ethyl acetate, washed with saturated aqueous sodium bicarbonate, and dried. The solution was concentrated to afford 4.0 g of the oxime as a white solid, m.p. 94°-98° C. This oxime was dissolved in 250 mL of methanol. To the system was added 4 g of Raney nickel, and the mixture was placed under 4 atm of hydrogen for 4 h. The catalyst was removed by filtration through celite. Concentration afforded 3.53 g of the title compound.

Step D:
3-((5'-Amino-6'-chloro-4'-pyrimidinyl)amino)-N-butyloxycarbonyl-aminomethylcyclobutane The procedure of Step D of Example 8 was repeated, replacing the product of Step C of Example 8 with the product of Step C of Example 9 to obtain the title compound as a foamy yellow solid. The diasteromeric mixture was separated by column chromatography: cis isomer, m.p. 149°-152° C.; trans isomer, 89°-94° C.

Step E:
3-(6'-Chloro-9'H-purin-9'-yl)-N-butyloxycarbonylaminomethylcyclobutane

The procedure of Step E of Example 8 was repeated replacing the product from Step D of Example 8 with the product from Step D of Example 9 to obtain the title compound as a white solid, m.p. 106°-110° C.

EXAMPLE 10

1-((3'-Hydroxymethyl)cyclobutyl)thymine

In a round bottom flask were placed 2.68 g of 3-methoxymethacrylic acid chloride and 25 mL of benzene. To the system was added 6.4 g of silver cyanate, and the mixture was heated at reflux for 40 min. In a round bottom flask were placed 1.0 g of the product from Step C of Example 5, 30 mL of DMF, and 10 mL of ether, and the system was cooled to −15° C. To the system was added 12.5 mL of the acylisocyanate prepared above, the solution was stirred at −15° C. for 2 h and allowed to stand in a refrigerator overnight. The reaction mixture was concentrated and the crude material was purified by column chromatography to afford 1.7 g of a solid, m.p. 120°-121° C. In a round bottom flask were placed 150 mg of this material and 5 mL of 2N aqueous sulfuric acid, and the reaction mixture was heated at reflux for 2 h. The mixture was brought to pH 7 with aqueous barium hydroxide, filtered, and the filtrate was concentrated. This reaction was repeated using 450 mg of the material prepared above, and the crude products from each reaction were combined and subjected to column chromatography to afford 429 mg of the title compound, m.p. 162°-164° C.

EXAMPLE 11

1-((3'-Hydroxymethyl)cyclobutyl)uracil

The procedure of Example 10 was repeated, replacing 3-methoxymethacrylic acid chloride with 3-ethoxyacrylic acid chloride to obtain the title compound, m.p. 44°-52° C.

EXAMPLE 12

1-((3'-Hydroxymethyl)cyclobutyl)cytosine

The procedure of Example 3 is repeated, replacing the product of Step B of Example 2 with the product of Example 11 to obtain the desired compound.

EXAMPLE 13

9-(((3'-(1,1-dimethylethyl)dimethylsilyl)oxymethyl)-2'-(hydroxymethyl)cyclobutyl)guanine To a solution of 1 mmol of the product from Step K of Example 1 in 20 mL of pyridine is added 1.5 equivalents of t-butyldimethylsilyl chloride. After 24 h at room temperature, the reaction mixture is concentrated under reduced pressure. Chromatography of the residue affords the desired product.

EXAMPLE 14

9-(((3'-(1,1-dimethylethyl)dimethylsilyl)oxymethyl)-2'-(methanesulfonyloxymethyl)cyclobutyl)guanine To a solution of 0.5 mmol of the product obtained from several executions of the procedure of Example 13 in 10 mL of dichloromethane at −60° to 0° C. is added 1.5 equivalents of triethylamine and 1.1 equivalents of methanesulfonyl chloride. After 1 h, the reaction mixture is treated with 1 equivalent of ethanol and then concentrated under reduced pressure. Rapid chromatography affords the desired compound.

EXAMPLE 15

9-(((3'-(1,1-dimethylethyl)dimethylsilyl)oxymethyl)-2'-(bromomethyl)cyclobutyl)guanine To a solution of 0.5 mmol of the product obtained from several executions of the procedure of Example 14 in 3 mL of DMF is added 1.1 equivalent of tetra-n-butylammonium bromide and the resulting mixture is heated at 50° C. for 24 h. The reaction mixture is then concentrated under reduced pressure and chromatography of the residue affords the desired compound.

EXAMPLE 16

9-(3'-hydroxymethyl-2'-bromomethylcyclobutyl)guanine

A solution of 0.5 mmol of the product obtained from several executions of the procedure of Example 15 in 2 mL of MeOH is treated with 1 equivalent of trimethylsilyl chloride. After 1 h at room temperature, the reaction mixture is concentrated under reduced pressure. Chromatography of the residue affords the desired compound.

EXAMPLE 17

9-(3'-Hydroxymethyl-2'-methylcyclobutyl)guanine

A solution of 0.5 mmol of the product obtained from several executions of the procedure of Example 15 in 5 mL of toluene at reflux is treated with 1 equivalent of tri-n-butyltin hydride. After 1 h, the reaction mixture is concentrated, and then deprotected and purified accroding to the procedure of Example 16 to afford the title compound.

EXAMPLE 18

9-(3'-Hydroxymethyl-2'-azidomethylcyclobutyl)guanine

The procedures of Examples 15 and 16 are repeated, but tetra-n-butylammonium azide is substituted for tetra-n- butylammonium bromide.

EXAMPLE 19

9-(3'-Hydroxymethyl-2'-aminomethylcyclobutyl)guanine

The product of Example 18 is dissolved in water and hydrogenated over Pd on carbon to afford the desired compound.

EXAMPLE 20

9-(2,'3,'-Bis(acetoxymethyl)cyclobutyl)guanine

To a stirred solution of 207 mg (0.780 mmol) of the product from Step K of Example 1 in 10 mL of acetonitrile is added 287 uL (2.06 mmol) of triethylamine, 7 mg (0.0585 mmol) of 4-dimethylaminopyridine, and 177 uL (1.87 mmol) of acetic anhydride. After 3 hours at room temperature, the clear solution is treated with 1 mL of methanol, concentrated under reduced pressure, redissolved in 2 mL of methanol, and then added to 50 mL of water. The resulting precipitate was removed by filtration, washed with water, and then dried under vacuum at 60° C. to afford 226 mg (83%) of the title compound as a white solid. $^1$H NMR (CDCl$_3$) 2.03, 2.11 (2s, 6 H, 2 CH$_3$), 2.29–2.46 (m, 2 H), 2.54–2.65 (m, 1 H), 2.96–3.05 (m, 1 H), 4.18–4.30 (m, 4 H, 2 CH$_2$O), 4.52 (ddd, 1 H, J=J'=J"=9 Hz, H-1'), 7.59 (s, 1 H, H-8).

EXAMPLE 21

3-(6'-Chloro-9'H-purin-9'-yl)-aminomethylcyclobutane hydrochloride

In a round bottom flask were placed the product of Step E of Example 9 (210 mg) and 1.4 mL of 4.5M HCl in dioxane. After 1.5 hours, the reaction mixture was concentrated to afford the title compound as a white solid. m.p. >250° C. (d).

EXAMPLE 22

9-(2',3'-Bisacetoxymethyl)cyclobutyl)-2-amino-6-chloropurine

To a stirred solution of 208 mg (0.595 mmol) of the product of Example 20 in 1.83 mL (19.6 mmol) of POCl$_3$ was added 93 uL (0.58 mmol) of N,N-diethylaniline, and the resulting mixture was heated at 70° C. After 1 hour, the excess POCl$_3$ was removed by evaporation at reduced pressure. The residue was then dissolved in 100 mL of dichloromethane and washed with 5×50 mL of water, dried over MgSO$_4$, and then concentrated under reduced pressure. Chromatography of the residue on 20 g of silica gel with 95:5/CH$_2$Cl$_2$:MeOH afforded 153 mg (70%) of the title compound as a light yellow oil. DCI NH$_3$ MS, m/z 368, 370 (M+H)$^+$.

EXAMPLE 23

9-(2',3'-Bis(hydroxymethyl)cyclobutyl-8-bromoguanine

To a suspension of 265 mg (1.00 mmol) of the product from Step K of Example 1 in 50 mL of water was added 9.0 mL (1.75 mmol) of a 0.194M solution of bromine in water in several small portions. After 4 hours, the reaction was cooled in an ice bath. The product was then removed by filtration, washed with water and acetone, and then dried over P$_2$O$_5$ to afford 232 mg (67%) of the title compound as an off-white solid. $^1$H NMR (D$_2$O, TSP=0.00 ppm) 2.12 (m, 1 H), 2.47 (ddd, 1 H, J=11 Hz, J'=J"=9 Hz, H-4), 2.75 (ddd, 1 H, J=11 Hz, J'=J"=10 Hz, H-4), 3.34–3.43 (m, 1H), 3.70 (d, 1 H, J=6 Hz, CH$_2$O), 3.80 (d, 1 H, J=6 Hz, CH$_2$O), 4.74 (ddd, 1 H, J=10 Hz, J'=J"=9 Hz, H-1). FAB MS, m/z 344,346 (M+H)$^+$.

EXAMPLE 24

9-(2',3'-Bis(acetoxymethyl)cyclobutyl)-2-aminopurine

A mixture of 2.63 g (7.15 mmol) of the product from Example 22, 1.18 g (14.3 mmol) of anhydrous sodium acetate, 1.0 g of 10% Pd on carbon and 100 mL of methanol was stirred under 1 atmosphere of hydrogen. After 12 hours, the reaction mixture was filtered and concentrated to a residue under reduced pressure. To the residue was added water and ethyl acetate, and the phases were separated. The aqueous phase was extracted with several portions of ethyl acetate and the combined organic extracts were concentrated under reduced pressure. Chromatography of the residue on silica gel with a 100:0 to 90:10/ethyl acetate:methanol gradient afforded 1.60 g (67%) of the title compound as an oil. DCI NH$_3$ MS, m/z 334 (M+H)$^+$.

EXAMPLE 25

[1'R,2'R,3'R]-9-(2',3')-Bis(hydroxymethyl)cyclobutyl)-guanine

Step A:

[1R,2R]-1,2-Bis(methoxycarbonyl)-3-methylenecyclopropane

1. The quinine salt (W. von E. Doering and D. Roth, *Tetrahedron,* 26, 2825–2835 (1970)) of 3-methylenecyclopropane-trans-1,2-dicarboxylic acid (F. Feist, *Chemische Berichte,* 26, 750 (1893)) (28.383 g, 60.9 mmol) was dissolved in 1 L of 10% aqueous sulfuric acid solution. The resultant solution was extracted thoroughly with diethyl ether as follows: the aqueous solution was extracted three times with 3 portions of diethyl ether. Each group of three extracts was pooled, washed with pH 2 brine, dried over anhydrous magnesium sulfate and the solvent evaporated to give 6.871 g of [1R,2R]-3-methylenecyclobutane-trans-1,2-dicarboxylic acid (m.p.=210° C.) from the first extracts, 0.924 g of [1R,2R]-3-methylenecyclopropane-trans-1,2-dicarboxylic acid (m.p.=210° C.) from the second extracts and 0.493 g of [1R,2R]-3-methylenecyclopropane-trans-1,2-dicarboxylic acid (m.p.=210° C.) from the third extracts, for a total of 8.29 g of diacid;

[α]$_D^{23}$ +151.6° (c 0.76; EtOH), [α]$_{546}^{23}$ +179.3° (c 0.76; EtOH); lit. * [α]$_{546}^{23}$ +176° (c 0.7; EtOH).

2. Diazomethane was generated from 50 g of N-methyl-N-nitroso-p-toluene sulfonamide (Diazald®, commercially available from Aldrich Chemical Co.) in diethyl ether. The ether solution of diazomethane was added to an ether solution of [1R,2R]-3-methylenecyclopropane-trans-1,2-dicarboxylic acid (8.288 g, 55.4 mmol), from Step A1, until a yellow color developed and persisted. After 10 minutes the excess diazomethane was quenched with glacial acetic acid and the ether solution was washed with dilute aqueous sodium bicarbonate solution and brine, dried over anhydrous magnesium sulfate, filtered and concentrated to give 8.812 g (88.8% yield from the diacid) of the title compound; [α]$_D^{23}$= +122.9° (c 1.06; CCl$_4$), [α]$_{546}^{23}$= +144.9° (c 1.06; CCl$_4$); lit. (W. von E. Doering and D. Roth, *Tetrahedron*, 26, 2825–2835 (1970) [α]$_{546}^{23}$+145° (c 0.7; CCl$_4$).

Step B:
[1R,2R]-1,2-Bis(hydroxymethyl)-3-methylenecyclopropane

A solution of 8.748 g (51.5 mmol) of [1R,2R]-bis(methoxycarbonyl)-3-methylenecyclopropane from Step A2 in 25 mL of toluene was added to 206 mL of 1.5M diisobutyl aluminum hydride (309 mmol) in toluene which had been cooled to −70° C. in a dry ice-acetone bath. The reaction mixture was stirred at −70° C. overnight and then quenched with 22.2 mL of methanol followed by 37.1 mL of water. The aluminum salts were filtered and washed with ethyl acetate and methanol. The ethyl acetate washes were combined and the solution was dried over anhydrous magnesium sulfate, filtered and concentrated to give 6.53 g of the title compound. The washed salts were suspended in methanol and the suspension was filtered. The filtrate was concentrated to give an additional 1.166 g of the title compound for a total of 7.696 g (131% yield) of crude product which was taken on to the next step without purification; MS DCI-NH$_3$ M/Z: 132 (M+NH$_4$)$^+$.

Step C:
[1R,2R]-1,2-Bis(((1',1'-dimethylethyl)dimethylsilyl)oxymethyl)-3-methylenecyclopropane The product of Step B (5.633 g, 49.4 mmol) was dissolved in 75 mL of N,N-dimethylformamide (DMF) and 16.8 g (247. mmol) of imidazole was added. The reaction mixture was cooled in an ice bath and 22.33 g (148 mmol) of t-butyldimethylsilyl chloride was added in one portion. The reaction mixture was allowed to warm to ambient temperature by removing the ice bath and stirring the reaction mixture overnight. The reaction was quenched with 10 mL of methanol, stirred for 0.5 h and concentrated in vacuo. The residue was diluted with 200 mL of ethyl acetate and the ethyl acetate solution was washed with aqueous sodium bicarbonate solution and brine, dried over anhydrous magnesium sulfate, filtered and concentrated in vacuo. The residue was purified on a 5×30 cm silica gel column eluted with methylene chloride to give 12.084 g (71.5% yield) of the title compound; MS DCI-NH$_3$ M/Z: 360 (M+NH$_4$)$^+$.

Step D:
[4R,5R]-4,5-Bis(((1',1'-dimethylethyl)dimethylsilyl)oxymethyl)-1-oxaspiro[2,2]pentane A solution of 15.8 g (46.2 mmol) of [1R,2R]-1,2-bis(((1,1-dimethylethyl)-dimethylsilyl)oxymethyl)-3-methylenecyclopropane, from Step C, in 200 mL of methylene chloride was cooled in an ice bath and treated with 15.945 g (46.2 mmol) of 50% meta-chloroperoxybenzoic acid (mCPBA). The reaction mixture was allowed to warm to ambient temperature and stirred overnight. TLC analysis on silica gel plates eluted with 10% hexane in ethyl acetate showed unreacted starting material, so 8.0 g of mCPBA was added. After stirring at ambient temperature for 6 h, another 2.16 g of mCPBA was added and stirring continued for 1.25 h. The reaction mixture was then diluted with methylene chloride, washed with 5% aqueous sodium bisulfite solution, 5% aqueous sodium bicarbonate solution and brine and then dried over anhydrous magnesium sulfate, filtered and concentrated to give 12.752 g (77% yield) of the title compound; MS DCI-NH$_3$ M/Z: 376 (M+NH$_4$)$^+$.

Step E:
[2R,3R]-2,3-Bis(((1,1-dimethylethyl)dimethylsilyl)oxymethyl)-cyclobutanone A solution of 12.752 g (35.6 mmol) of [4R,5R]-4,5-bis(((1,1-dimethylethyl)-dimethylsilyl)oxymethyl)-1-oxaspiro[2,2]pentane, from Step D, in 50 mL of methylene chloride was added to a solution of 3.814 g (28.5 mmol) of lithium iodide in 200 mL of methylene chloride which had been cooled in an ice bath. After stirring the reaction mixture for 1 h at 0° C., the ice bath was removed and the reaction mixture was stirred for 20 minutes at ambient temperature. The reaction mixture was then washed with 5% aqueous sodium bicarbonate solution, 5% sodium bisulfite solution and brine, dried over anhydrous magnesium sulfate, filtered and concentrated under reduced pressure to give 12.317 g (96.6% crude yield) of the title compound which was taken on to the next step without purifiaction; MS DCI-NH$_3$ M/Z: 376 (M+NH$_4$)$^+$.

Step F:
[2R,3R]-2,3-Bis(((1,1-dimethylethyl)dimethylsilyl)oxymethyl)-cyclobutanone O-methyl oxime A solution of 12.317 g (34.9 mmol) of [2R,3R]-2,3-Bis(((1,1-dimethylethyl)dimethylsilyl)oxymethyl)cyclobutanone, from Step E, in 20 mL of pyridine was added to a solution of 3.160 g (37.8 mmol) of methoxylamine hydrochloride in 80 mL of pyridine. After stirring the reaction mixture for 70 min at ambient temperature, it was concentrated to approximately ¼ of the original volume then diluted with ethyl acetate, washed with saturated aqueous sodium bicarbonate solution, dried over anhydrous magnesium sulfate, filtered and concentrated in vacuo. The residue was purified by flash chromatography on a 5×38 cm silica gel column eluted with 1 L of hexane and 5% acetone in hexane to give 10.228 g (75.7% yield) of the title compound as a mixture of geometrical isomers. .MS DCI-NH$_3$ M/Z: 388 (M+H)$^+$.

Step G:
[1R,2R,3R]-2,3-Bis(((1,1-dimethylethyl)dimethylsilyl)oxymethyl)-cyclobutylamine To 4.74 g (125 mmol) of sodium borohydride in 125 mL of tetrahydrofuran (THF) was added (slowly) 14.25 g (9.63 mL, 125 mmol) of trifluoroacetic acid (TFA), followed by 10.228 g (26.4 mmol) of [2R,3R]-2,3-Bis(((1,1-dimethylethyl)di-methylsilyl)oxymethyl)cyclobutanone-O-methyl oxime, from Step F, in 25 mL of THF. After stirring the reaction mixture at ambient temperature for 1.5 h, it was concentrated, diluted with methylene chloride and washed with brine. An emulsion developed which cleared up after filtration. The methylene chloride solution was dried overnight over anhydrous magnesium sulfate, filtered and concentrated to give 10.98 g of crude title compound which was taken on to the next step without purification; MS DCI-NH$_3$ M/Z: 360 (M+NH$_4$)+.

Step H: [1R,2R,3R]-3-((2'-Amino-3',4'-dihydro-4'-nitro-4'-oxo-6'-pyrimidinyl)-amino-1,2-bis(((1,1-dimethylethyl)dimethylsilyl)oxymethyl)cyclobutane The crude product from Step G was combined with 5.032 g (20.4 mmol) of 2-amino-6-chloro-3,4-dihydroxy-5-nitro-4-oxopyrimidine (prepared as described by C. Temple et al. in *J. Org Chem*, 40, 3141–3142 (1975)) and 5.5 mL (39.6 mmol) of triethylamine in 40 mL of DMF and this mixture was heated at 50° C. for 3.5 h. The solvent was evaporated in vacuo and the residue was triturated with diethyl ether and filtered. The filtrate was washed with water and brine, dried over anhydrous magnesium sulfate, filtered and concentrated. The residue was purified on a 3×55 cm silica gel column eluted with 5% methanol in methylene chloride to give 10.8 g (79.7% yield from the O-methyl oxime) of the title compound; MS DCI-NH$_3$M/Z: 514 (M+H)+.

Step I:
9-([1'R,2'R,3'R]-2',3'-Bis(hydroxymethyl)cyclobutyl)-guanine

[1R,2R,3R]-3-((2'-Amino-3'-dihydro-5'-nitro-4'-oxo-6'-pyrimidinyl)-amino-1,2-bis(((1,1-dimethyl)dimethylsilyl)oxymethyl)cyclobutane (2.0 g, 3.9 mmol) from Step H was hydrogenated at 4 atmospheres of hydrogen, in 150 mL of formic acid, over 0.4 g of 10% palladium on carbon for 1.25 h. The catalyst was removed by filtration and the filtrate was heated at 130° C. for 8 h. The solvent was then evaporated in vacuo and the residue slurried in water. The water was removed in vacuo and water was added to the residue to form a slurry which was evaporated in vacuo. The residue was again slurried in water and the slurry was filtered. The precipitate was washed with water and treated with 100 mL of concentrated ammonium hydroxide solution at ambient temperature for approximately 1 h. The ammonium hydroxide solution was then filtered and the filtrate concentrated. The solid residue was crystallized from water to give 523 mg (50% yield) of the title compound as off-white needles, $[\alpha]_D^{23} = +22.4°$ (c 0.32; 0.01N NaOH); MS DCI-NH$_3$, M/Z: 266 (M+H)+; $^1$H NMR (D$_2$O) δ 2.17 (ddd, 1H, J+J' = 10 Hz, J''32 9 Hz, H-4'), 2.16–2.28, 2.58–2.66, 2.69–2.78 (3m, 3H, H-4', H-2', H-3'), 3.72, 3.74 (2d, 4H, J=6 Hz, 2 CH$_2$O), 4.51 (ddd, 1H, J=J'=J''=9 Hz, H-1'), 7.97 (s, 1H, H-8).

HPLC analysis of the title compound on a Nucleosil Chiral-1 column (Nucleosil is a registered trademark of Macherey Nagel. The Nucleosil Chiral-1 column is available commercially from Alltech Associates, Inc.) using a mobile phase consisting of 0.5 millimolar aqueous copper acetate adjusted to pH 5.75 with glacial acetic acid indicated an enantiomeric purity exceeding the limit of detection. The enantioselectivity factor of this system was 1.22.

EXAMPLE 26
[1'R,2'R,3'R]-9-(2',3'-Bis(hydroxymethyl)cyclobutyl)adenine

Following the procedures described in Example 4, replacing the product of Step E of Example 1 with the product of Step G of Example 25, the title compound is prepared with both hydroxyl groups protected with t-butyldimethylsilyl groups. The protecting groups are removed as described in Step E of Example 1.

EXAMPLE 27
[1'R,2'R,3'R]-1-(2',3'-Bis(hydroxymethyl)cyclobutyl)uracil

Following the procedures described in Example 2, replacing the product of Step D of Example 1 with the product of Step G of Example 25, the title compound is prepared.

EXAMPLE 28
[1'R,2'R,3'R]-1-(2',3'-Bis(hydroxymethyl)cyclobutyl)thymine

Following the procedures described in Example 2, replacing, in Step A, the product of Step D of Example 1 with the product of Step G of Example 25, and replacing, in Step B, (E)-3-ethoxyacryloyl chloride with 3-methoxymethacryloyl chloride, the title compound is prepared.

EXAMPLE 29
[1'R,2'R,3'R]-1-(2',3'Bis(hydroxymethyl)cyclobutyl)-cytosine

Following the procedures described in Example 3, replacing the product of Step B of Example 2 with the product of Example 27, the title compound is prepared.

EXAMPLE 30
[1'S,2'S,3'S]-9-(2',3'-Bis(hydroxymethyl)cyclobutyl)-guanine

Following the procedures described in Example 25, replacing the [1R,2R]-3-methylenecyclopropane-trans-1,2-dicarboxylic acid in Step H with [1R,2R]-3-methylenecyclopropane-trans-1,2-dicarboxylic acid, the desired compound is prepared. The [1S,2S]-diacid is obtained from the resolution of 3-methylenecyclopropane-trans-1,2-dicarboxylic acid with brucine according to the method reported by J. J. Gajewski in *J. Am. Chem. Soc.*, 93, 4450–8 (1971).

EXAMPLE 31
[1'S,2'S,3'S]-9-(2',3'-Bis(hydroxymethyl)cyclobutyl)adenine

Following the procedures described in Example 26, replacing the product of Step G of Example 25 with [1S,2D,3S]-2,3-Bis(((1,1-dimethylethyl)dimethylsilyl)oxymethyl)cyclobutylamine from Example 30, the desired product is obtained with both hydroxyl groups protected with t-butyldimethylsilyl groups. The protecting groups are removed as described in Step E of Example 1.

EXAMPLE 32

[1'S,2'S,3'S]-1-(2',3'-Bis(hydroxymethyl)cyclobutyl)uracil

Following the procedures described in Example 2, replacing the product of Step D of Example 1 with [1S,2D,3S]-2,3-Bis(((1,1-dimethylethyl)dimethylsilyl)oxymethyl)cyclobutylamine from Example 25, the title compound is prepared.

EXAMPLE 33

[1'S,2'S,3'S]-1-(2',3'-Bis(hydroxymethyl)cyclobutyl)thymine

Following the procedures in Example 2, replacing, in Step A, the product of Step D of Example 1 with [1S,2S,3S]-2,3-Bis(((1,1-dimethylethyl)dimethylsilyl)oxymethyl)cyclobutylamine from Example 25, and replacing, in Step B, (E)-3-ethoxyacryloyl chloride with 3-methoxymethacryloyl chloride, the title compound is prepared.

EXAMPLE 34

[1'S,2'S,3'S]-1-(2',3'-Bis(hydroxyemthyl)cyclobutyl)cytosine

Following the procedures described in Example 3, replacing the product of Step B of Example 2 with the product of Example 32, the title compound is prepared.

EXAMPLE 35

9-(2'-Hydroxymethyl-1'-cyclobutyl)guanine

Step A: Methyl 1-cyclobutenecarboxylate

A solution of 1-cyclobutenecarboxylic acid, prepared as described by W. G. Dauben and J. R. Wiseman, *J Am Chem Soc*, 89, 3545 (1967), in 75 mL of diethyl ether was treated with a freshly prepared and distilled solution of diazomethane in diethyl ether. The ether solution of diazomethane was added until a yellow color persisted in the reaction solution. The reaction solution was purged with nitrogen and concentrated in vacuo at 40° C. to give crude methyl 1-cyclobutenecarboxylate in quantitative yield. The product was taken on to the next step without purification; $^1$H NMR (CDCl$_3$) δ 2.49 (dt, 2H), 2.73 (t, 2H), 3.72 (s, 3H), 6.79 (t, 1H).

Step B: 2-Amino-6-chloro-9-(2'-methoxycarbonyl-1'-cyclobutyl)purine

Methyl 1-cyclobutenecarboxylate (0.28 g, 2.5 mmol) from Step A was combined under a nitrogen atmosphere with 606 mg (3.6 mmol) of 2-amino-6-chloropurine and 53 µL (0.36 mmol) of 1,8-diazabicyclo[5.4.-0]undec-7-ene (DBU) in 75 mL of acetonitrile. After stirring for 66 h at ambient temperature, a second 53 µL aliquot of DBU was added and stirring continued. After a total of 36 h, the reaction was quenched by the addition of 0.28 mL of glacial acetic acid and the reaction mixture was concentrated in vacuo. The residue (2.43 g) was dissolved in approximately 3 mL of methylene chloride and purified on a 1.8×47 cm silica gel column eluted @ 2-3 psi with the following step-wise solvent gradient: 1). 250 mL of methylene chloride, 2). 250 mL of 2% methanol in methylene chloride, 3). 250 mL of 4% methanol in methylene chloride and 4). 250 mL of 6% methanol in methylene chloride, to give 715 mg (71% yield) of the title compound as a mixture of cis and trans isomers. Equilibration to the desired trans isomer was achieved by treating the mixture of isomers 455 µL of DBU in 35 mL of acetonitrile at 45° C., under nitrogen, for 42 h. The reaction mixture was concentrated in vacuo and the residue was dissolved in approximately 2 mL of methylene chloride and purified on a 1.5×45 cm silica gel column eluted @ 5 psi with a step-wise solvent gradient of 200 mL of methylene chloride followed by 200 mL of 2% methanol in methylene chloride and 200 mL of 4% methanol in methylene chloride to give 608 mg (87% yield) of the desired trans iaomer of the title compound. MS DCI-NH$_3$ M/Z: 282 and 284 (M+H)$^+$.

Step C: 2-Amino-6-chloro-9-(2'-hydroxymethyl-1'-cyclobutyl)purine

2-Amino-6-chloro-9-(2'-methoxycarbonyl-1'-cyclobutyl)purine (605 mg, 2.15 mmol) from Step B was dissolved in 250 mL of freshly distilled dry THF and the solution was cooled to 0° C. under a nitrogen atmosphere. Lithium aluminum hydride (122 mg, 3.2 mmol) was added in one portion and the reaction mixture was stirred at 0° C. (under a nitrogen atmosphere) for 0.5 h. The reaction was then quenched by the addition of 122 µL of water, followed by 122 µL of 15% sodium hydroxide and 366 µL of water. The reaction mixture was filtered and the filter cake was washed with ethyl acetate. The filtrate was concentrated in vacuo to give 490 mg (90% yield) of the title compound; MS DCI-NH$_3$ M/Z: 254 and 256 (M+H)$^+$.

Step D: 9-(2'-Hydroxymethyl-1'-cyclobutyl)guanine

2-Amino-6-chloro-9-(2'-hydroxymethyl-1'-cyclobutyl)purine (490 mg, 22.5 mmol) from Step C and 100 mL of 1M hydrochloric acid solution were combined and heated at reflux under nitrogen for approximately 5 h. The reaction mixture was concentrated in vacuo at 45°-50° C. The residue was azeotropically distilled three times with 25 mL of absolute ethanol and the resultant residue (543 mg) was dissolved in 5 mL of water. The aqueous solution was neutralized with concentrated ammonium hydroxide solution and concentrated in vacuo. The residue (594 mg) was dissolved in 180 mL of 50% aqueous ethanol and the resultant solution was heated to 70° C., treated with 50 mg Darco G-60 charcoal, filtered and concentrated to approximately 35 mL @80° C. This solution was allowed to cool to 3° C. slowly overnight and the crystals were collected by suction filtration to give 336 mg (74% yield) of the title compound; MS DCI-NH$_3$ M/Z: 236 (M+H)$^+$; $^1$H NMR (d6-DMSO) δ 1.60 (m, 1H), 1.85 (m, 1H), 2.20-2.40 (m, 2H), 2.98 (m, 1H), 3.42 (t, 2H), 4.51 (q, 1H), 7.88 (s, 1H); Analysis calculated for C$_{10}$H$_{13}$N$_5$O$_2$: C, 51.05; H, 5.57; N, 29.77. Found: C, 51.07; H, 5.63; N, 29.65.

EXAMPLE 36

9-(2'-hydroxymethyl-1'-cyclobutyl)adenine

Step A: 9-(2-methoxycarbonyl-1-cyclobutyl)adenine

Adenine (486 mg, 3.6 mmol) was combined with an excess of methyl 1-cyclobutene carboxylate (~25 mmol) from Step B of Example 35 and 53 µL (0.36 mmol) of DBU in 75 mL of acetonitrile and the mixture was stirred at ambient temperature, under a nitrogen atmosphere. After 66 h, a second 53 µL aliquot of DBU was added and stirring continued. After a total of 136 h, the reaction was quenched by the addition of 0.28 mL of glacial acetic acid and concentrated in vacuo. The residue was dissolved in approximately 3 mL of methylene chloride and purified on a 1.5×45 cm silica gel column eluted @ 5-10 psi with a step-wise solvent gradient of methanol in methylene chloride, starting with 100% methylene chloride and increasing in 2% steps to 8% methanol, each step was 200 mL of solvent. The title compound was obtained in 61% yield (542mg) as a mixture of cis and trans isomers and equilibrated to the desired trans isomer by treating the mixture of isomers with 394 μL of DBU in 35 mL of acetonitrile at 45° C., under nitrogen, for 46 h. The reaction mixture was concentrated in vacuo and the residue was dissolved in approximately 2 mL of methylene chloride and purified on a 1.5×45 cm silica gel column eluted @5 psi with a step-wise solvent gradient of 200 mL of methylene chloride followed by 200 mL of 5% methanol in methylene chloride and 200 mL of 7% methanol in methylene chloride to give 502 mg (57% yield) of the desired trans isomer of the title compound; $^1$H NMR (CD$_3$OD) δ 2.11 (m, 1H), 2.30 (m, 1H), 2.45 (m, 1H), 2.77 (m, 1H), 3.68 (s, 3H), 4.01 (m, 1H), 5.18 (q, 1H), 8.20 (s, 1H), 8.25 (s, 1H); MS DCI-NH$_3$ M/Z: 248 (M+H)$^+$.

Step B: 9-(2-hydroxymethyl-1-cyclobutyl)adenine 9-(2-methoxycarbonyl-1-cyclobutyl)adenine (500 mg, 2.02 mmol) from Step A was dissolved in 250 mL of THF and the solution was cooled to 0° C. with stirring under a nitrogen atmosphere. Lithium aluminum hydride (115 mg, 3.03 mmol) was added and the reaction mixture was stirred for 30 minutes then quenched with 115 μL of water followed by 115 μL of 15% sodium hydroxide and 345 μL of water. The reaction mixture was filtered through Celite filter aid. The Celite was washed with ethyl acetate and the filtrater concentrated in vacuo to give 430 mg (97% yield) of the title compound; MS DCI-NH$_3$ M/Z: 220 (M+H)$^+$; $^1$H NMR (d6-DMSO) δ 1.65 (m, 1H), 1.90 (m, 1H), 2.32 (m, 1H), 2.50 (m, 1H), 3.10 (m, 1H), 3.47 (t, 2H), 4.67-4.77 (m, 2H, H-1'+OH), 7.20 (bs, 2H), 8.12 (s, 1H), 8.27 (s, 1H); Analysis calculated for C$_{10}$H$_{13}$N$_5$O: C, 54.78; H, 5.98; N, 31.95. Found: C, 54.79; H, 6.01; N, 31.66.

EXAMPLE 37

1-(2'-Hydroxymethyl-1'-cyclobutyl)uracil

Following the procedures in Example 36, replacing adenine with uracil, the title compound is prepared.

EXAMPLE 38

1-(2'-Hydroxymethyl-1'-cyclobutyl)thymine

Following the procedures in Example 36, replacing adenine with thymine, the title compound is prepared.

EXAMPLE 39

1-(2'-Hydroxymethyl-1'-cyclobutyl)cytosine

Following the procedures in Example 36, replacing adenine with cytosine, the title compound is prepared.

EXAMPLE 40

9-(2'-(Hydroxymethyl)-3'-methylcyclobutyl)guanine

Step A: 9-(2'-(Hydroxymethyl)-3'-((2''-pyridyl)mercaptomethyl)-cyclopropyl)guanine 9-(2',3'-Bis(hydroxymethyl)cyclobutyl)guanine (1.5 g, 5.6 mmol), prepared as described in Example 1, 1.25 g (5.6 mmol) of 2,2'-dipyridyl disulfide (Aldrithiol-2 ® commercially available from Aldrich Chemical Company) and 5.7 g (28.3 mmol) of tri-n-butylphosphine were combined in 50 mL of pyridine and the reaction mixture was stirred at ambient temperature, under a nitrogen atmosphere, for 16 h. At this time some starting materials were still unreacted according to TLC analysis on silica gel plates eluted with 20% methanol in methylene chloride, and an additional 400 mg of Aldrithiol-2 ® was added and stirring continued. After a total of 41 h, the reaction was quenched with methanol and evaporated in vacuo. The residue was dissolved in 5 mL of methylene chloride and purified on a 3×50 cm silica gel column eluted at 2-3 psi with a solvent gradient of methanol in methylene chloride as follows: 750 mL of 5% methanol in methylene chloride followed by 1 L of 10% methanol in methylene chloride, followed by 1 L of 15% methanol in methylene chloride and finally 2 L of 20% methanol in methylene chloride, to give 63 mg (3% yield) of the title compound; $^1$H NMR (CD30D) δ (2.3-3.4, m, 2H), 2.62 (m, 1H), 2.83 (m, 1H), 3.4-3.5 (m, 2H), 3.6-3.75 (m, 2H), 7.1 (m, 1H), 7.3 (m, 1H), 7.6 (m, 1H), 7.84 (s, 1H), 8.4 (m, 1H); MS DCI-NH$_3$ M/Z: 359 (M+H)$^+$.

Step B: 9-(2'-(Hydroxymethyl)-3'-methylcyclopropyl)guanine 9-(2'-(Hydroxymethyl)-3'-((2''-pyridyl)mercaptomethyl)cyclobutyl)guanine (60 mg, 0.17 mmol) from Step A was dissolved in 5 mL of ammonia at −78° C. and sodium metal was added until a persistent blue color was observed (~100 mg of sodium). The reaction mixture was stirred at −78° C. under a nitrogen atmosphere for 0.5 h and then quenched with approximately 50 mg of solid ammonium chloride. The ice bath was removed and ammonia gas was swept out of the reaction mixture with nitrogen. The residue was suspended in approximately 2 mL of water and purified on a 1.0×45 cm reverse phase column of Bondesil ® C18 (40 μm particles) packed with methanol, equilibrated with 100 mL of water @ 10 psi and eluted @ 10 psi with 50 mL of water, followed by 50 mL of 10% aqueous methanol, followed by 20% aqueous methanol and finally 30% aqueous methanol to give 22 mg (52% yield) of the title compound; DCI-NH$_3$ MS M/Z: 250 (M+H)$^+$; $^1$H NMR (d6-DMSO) δ 1.14 (d, 3H), 1.87-1.97 (m, 2H), 2.45 (m, 2H), 3.45 (t, 2H), 4.32 (q, 1H), 7.79 (s, 1H).

EXAMPLE 41

9-(2'-(Hydroxymethyl)-3'-methylcyclobutyl)adenine

Following the procedures described in Example 40, replacing 9-(2',3'-bis(hydroxymethyl)-cyclobutyl)guanine, the product of Example 1, with 9-(2',3'-bis(hydroxymethyl)cyclobutyl)adenine, Example 4, the title compound is prepared.

EXAMPLE 42

9-(2'-Hydroxy-3'-hydroxymethyl-1'-cyclobutyl)guanine

Step A:
2,3-Bis(((1.1-dimethylethyl)dimethyl)oxymethyl)-1-methylenecyclobutane 1,2-Bis(hydroxymethyl)-3-methylenecyclobutane (29.9 g, 233 mmol), obtained from Step A of Example 1, and t-butyldimethylsilyl chloride (140 g, 900 mmol) were combined in 800 mL of anhydrous pyridine and the reaction mixture was stirred at ambient temperature overnight under a nitrogen atmosphere. The reaction was quenched with 20 mL of methanol and the reaction mixture concentrated under reduced pressure to a syrup. The syrup was dissolved in 1 L of methylene chloride and the solution washed with 5% aqueous sodium bicarbonate solution (3×300 mL), dried over anhydrous magnesium sulfate, filtered and concentrated under reduced pressure. The syrup-like residue (105 g) was purified on a 4.8×20 cm silica gel column packed with hexane and eluted @ 1-2 psi with 1 L of hexane to give 78.6 g (95% yield) of the title compound; MS DCI-NH$_3$ M/Z: 357 (M+H)+, 374 (M+NH$_4$)+; $^1$H NMR (CDCl$_3$) δ 0.05 (s, 12H), 0.90 (s, 18H), 2.20 (m, 1H), 2.40 (m, 1H), 2.60 (m, 1H), 2.82 (m, 1H), 3.60-3.70 (m, 4H), 4.76 (q, 1H), 4.84 (q, 1H).

Step B:
2,3-Bis(((1,1-dimethyl)dimethylsilyl)oxymethyl)cyclobutanone 2,3-Bis(((1,1-dimethylethyl)dimethylsilyl)oxymethyl)-1-methylene-cyclobutane (30 g, 82 mmol) from Step A was dissolved in a mixture of 600 mL of methylene chloride and 150 mL of methanol and this mixture was cooled to −78° C. Ozone was bubbled through the reaction mixture at −78° C. until a persistent blue color was observed (approximately 4.5 h). Nitrogen was then bubbled through the reaction mixture until it became colorless. To this colorless solution was added 50 mL of dimethyl sulfide and stirring was continued at −78° C. for 15 minutes. The reaction mixture was allowed to stand overnight at 0° C. and then carefully concentrated under reduced pressure. The syruplike residue (72.7 g) was purified on a 2.5×40 cm silica gel column eluted @5 psi with 1.1 L of hexane to give 10.2 g (35% yield) of the title compound as a syrup; IR (CDCl$_3$ solution) 1778 (C=O), 1055 (C—O) cm$^{-1}$; $^1$H NMR (CDCl$_3$) δ 0.05 (d, 12H), 0.85 (d, 18H), 2.64 (m, 1H), 2.88 (m, 1H), 3.18 (m, 1H), 3.65 (dd, 1H), 3.75 (t, 2H), 3.86 (dd, 1H); MS DCI-NH$_3$ M/Z: 359 (M+H)+, 376 (M+NH$_4$)+.

Step C:
2.3-Bis(((1,1-dimethylethyl)dimethylsilyl)oxymethyl)-cyclobutanol 2,3-Bis(((1,1-dimethylethyl)dimethylsilyl)oxymethyl)cyclobutanone (10.2 g, 28.4 mmol) from Step B was dissolved in tetrahydrofuran (THF) and the solution was cooled to −78° C. under a nitrogen atmosphere. To the THF solution at −78° C. was slowly added, with stirring, 31 mL (31 mmol) of potassium tri-sec-butylborohydride (sold by Aldrich Chemical Company as a 1M solution in THF under the registered trademark K-Selectride®). After stirring for 0.5 h at −78° C., the reaction mixture was allowed to warm to 0° C. and it was stirred for 40 minutes at 0° C. One equivalent (1.9 mL) of glacial acetic acid was added and the reaction mixture was concentrated in vacuo to approximately 50 mL. The concentrate was diluted with 1 L of methylene chloride and the resultant solution was washed with 400 mL of 5% aqueous sodium bicarbonate solution, dried over anhydrous magnesium sulfate, filtered and concentrated to a syrup. The syrup (15.5 g) was chromatographed on a 4.5×45 cm silica gel column eluted @ 2-5 psi with 2 L of methylene chloride. All fraction containing the desired product were combined and concentrated. The residue (10 g) was rechromatographed as described above to give 6.3 g (62% yield) of the title compound as a syrup; $^1$H NMR (CDCl$_3$) δ 0.07 (d, 12H), 0.92 (d, 18H), 2.01 (m, 1H), 2.13 (m, 2H), 2.25 (m, 1H), 2.40 (m, 1H), 3.35 (d, 1H), 3.55 (m, 2H), 3.86 (dd, 1H), 3.98 (dd, 1H); MS DCI-NH$_3$ M/Z: 361 (M+H)+.

Step D: 2,3-Bis(hydroxymethyl)cyclobutanol 2,3-Bis(((1,1-dimethylethyl)dimethylsilyl)oxymethyl)cyclobutanol (6.3 g, 17.5 mmol) from Step C was combined with 5.3 mL (43 mmol) of chlorotrimethylsilane in 103 mL of methanol. The reaction mixture was stirred at ambient temperature under a nitrogen atmosphere for 0.5 h then concentrated under reduced pressure to an oil. Residual chlorotrimethylsilane was removed by co-evaporation with methanol (3×30 mL) to give title compound in quantitative yield and this crude product was carried on to the next step without purification; $^1$H NMR (CD$_3$OD) δ 1.94-2.14 (m, 2H), 2.17-2.37 (m, 2H), 3.53 (d, 2H), 3.68 (dd, 1H), 3.85 (dd, 1H), 4.39 (m, 1H); MS DCI-NH$_3$ M/Z: 133 (M+H)+, 150 (M+NH$_4$)+.

Step E: 7-Hydroxymethyl-3-phenyl-2,4 dioxabicyclo[2.4.0]octane 2,3-Bis(hydroxymethyl)-cyclobutanol (17.5 mmol) from Step D and 2.7 g (17.5 mmol) of benzaldehyde dimethyl acetal were combined in a mixture of 30 mL of freshly distilled methylene chloride and 30 mL of freshly distilled THF. The reaction mixture was stirred at ambient temperature for 1.5 h under a nitrogen atmosphere and then an additional 1 mL of benzaldehyde dimethyl acetal was added. After stirring the reaction mixture for 2 h, 100 mL of 5% aqueous sodium bicarbonate solution was added. The resultant aqueous solution was extracted with 250 mL of methylene chloride. The organic phase was dried over anhydrous magnesium sulfate, filtered and concentrated in vacuo. The residue (4.5 g) was dissolved in 5-10 mL of methylene chloride and purified on a 2.5×40 cm silica gel column eluted @ 5 psi with 500 mL of methylene chloride followed by 500 mL of 4% methanol in methylene chloride to give 2.85 g (74% yield) of the title compound as a syrup; MS DCI-NH$_3$ M/Z: 221 (M+H)+; $^1$H NMR (CDCl$_3$) δ 1.91-2.09 (m, 2H), 2.18 (m, 1H), 3.17 (m, 1H), 3.71 (m, 1H), 4.03 (d, 2H), 4.59 (t, 1H), 5.36 (s, 1H), 7.35 (m, 3H), 7.52 (dd, 2H).

Step F:
1-Benzoyloxy-2-bromomethyl-3-hydromethylcyclobutane

7-Hydroxymethyl-3-phenyl-2,4-dioxabicyclo[2.4.0]octane (2.85 g, 12.9 mmol) from Step E was combined with 2.6 g (14.6 mmol) of N-bromosuccinimide and 3.5 g (17.7 mmol) of barium carbonate in 1,2-dichloroethane which had been dried over molecular sieves. The reaction mixture was heated to reflux under a nitrogen atmosphere for 1 h. The reaction mixture was filtered and the filtrate diluted with 100 mL of methylene chloride, washed with 100 mL of 5% aqueous sodium carbonate and 100 mL of water, dried over anhydrous magnesium sulfate and concentrated. The residue was dissolved in approximately 2 mL of methylene chloride and purified on a 1.5×40 cm silica gel column eluted @ 5 psi with 100 mL of methylene chloride, followed by 200 mL of 1% methanol in methylene chloride and 200 mL of 2% methanol in methylene chloride to give 2.5 g (65% yield) of the title compound as a syrup; $^1$H NMR (CDCl$_3$) δ 2.33 (m, 2H), 2.50 (m, 1H), 3.60 (t, 2H), 3.18–3.31 (m, 3H), 5.41 (m, 1H), 7. 47 (m, 2H), 7.59 (m, 1H), 8.05 (m, 2H); MS DCI-NH$_3$ M/Z: 299 and 301 (M+H)+, 316 and 318 (M+NH$_4$)+.

Step G:
1-Benzoyloxy-3-hydroxymethyl-2-methylenecyclobutane

1-Benzoyloxy-2-bromomethyl-3-hydroxymethylcyclobutane (2.5 g, 8.36 mmol) from Step F and tetra-n-butylammonium fluoride ((8.1 g, 25 mmol) were combined in 200 mL of freshly distilled THF and the reaction mixture was stirred at ambient temperature, under a nitrogen atmosphere, overnight. The volume of the reaction mixture was then reduced to 25 mL and this was dissolved in 250 mL of methylene chloride. The methylene chloride solution was washed with 150 mL of water, dried over anhydrous magnesium sulfate, filtered and concentrated under reduced pressure. The residue (4.9 g) was dissolved in ~5 mL of methylene chloride and purified on a 2.5×35 cm silica gel column eluted @ 5 psi with a step-wise (4×200 mL steps) of methanol in methylene chloride from 0% to 3% methanol to give 1.54 g (85% yield) of the title compound as a syrup; $^1$H NMR (CDCl$_3$) δ 2.38 (m, 2H), 3.22 (m, 1H), 3.69–3.85 (m, 2H), 5.13 (t, 1H), 5.32 (t, 1H), 5.79 (M, 1H), 7.45 (m, 2H), 7.58 (m, 1H), 8.08 (m, 2H); MS DCI-NH$_3$ M/Z: 219 (M+H)+, 236 (M+NH$_4$)+.

Step H: 2-Benzoyloxy-4-hydroxymethylcyclobutanone

A mixture of 2.09 g (9.5 mmol) of 1-benzoyloxy-3-hydroxymethyl-2-methylenecyclobutane from Step G, 112 mL of methylene chloride and 28 mL of methanol was cooled to −78° C. under a nitrogen atmosphere. Ozone was bubbled through the mixture for 10 minutes, until a persistent blue color was observed. Excess ozone was flushed out with nitrogen, 9 mL of dimethyl sulfide was added and the reaction mixture stirred for 0.5 h at −78° C. The reaction mixture was allowed to warm to ambient temperature, stirred for 0.5 h at ambient temperature and evaporated under reduced pressure to a syrup. The syrup (2.5 g) was dissolved to ~2 mL of methylene chloride and purified on a 1.5×45 cm silica gel column eluted @ 5 psi with 100 mL of methylene chloride, followed by 250 mL of 1% methanol in methylene chloride and 250 mL of 2% methanol in methylene chloride to give 1.79 g (86% yield) of the title compound; MS DCI-NH$_3$ M/Z: 221 (M+H)+, 238 (M+NH$_4$)+.

Step I: 2-Benzoyloxy-4-hydroxymethylcyclobutanol

Glacial acetic acid in (25 mL) a 250 mL 3-neck flask was cooled in an ice bath under a stream of nitrogen. Sodium borohydride was added cautiously in portions over a 5 minute period. The ice bath removed and the reagent was used after stirring for 15 minutes at ambient temperature. 2-Benzoyloxy-4-hydroxymethylcyclobutanone (1.43 g, 6.5 mmol) from Step H was dissolved in 45 mL of glacial actetic acid and immediately treated with the above borohydride reagent. After stirring the reaction mixture for 35 minutes, the reaction was quenched with ~2 mL of methanol and the reaction mixture was concentrated in vacuo to a syrup. The syrup was dissolved in 250 mL of ethyl acetate and the ethyl acetate solution was washed with water and 5% aqueous sodium bicarbonate, dried over magnesium sulfate, filtered and concentrated to give 1.47 g of the title compound which was taken on to the next step without purification; MS DCI-NH$_3$ M/Z: 221 (M+H)+, 238 (M+NH$_4$)+.

Step J:
2-Benzoyloxy-1-(((1,1-dimethylethyl)diphenylsilyl)oxy)-4-(((1,1-dimethylethyl)diphenylsilyl)oxymethyl)cyclobutane 2-Benzoyloxy-4-hydroxymethylcyclobutanol (1.9 g, 8.5 mmol) from Step I, t-butyldiphenylsilyl chloride (5.2 g, 18.6 mmol) and imidazole (2.6 g, 37.6 mmol) were combined in 140 mL of N,N-dimethylformamide (DMF) and the reaction mixture was stirred at ambient temperature for 64 h under a nitrogen atmosphere. The reaction mixture was concentrated in vacuo and the residue dissolved in 250 mL of diethyl ether. The ether solution was washed with 3×100 mL of water, dried over anhydrous magnesium sulfate, filtered and concentrated under reduced pressure. The residue (6.8 g) was dissolved in 10 mL of hexane and purified on a 2.8×54 cm silica gel column eluted at 5 psi with a step-wise solvent gradient of acetone in hexane of 4×1% steps @ 500 mL each, from 1% to 4% acetone. The title compound was obtained (4.22 g) in 72% yield; MS DCI-NH$_3$ M/Z: 716 (M+NH$_4$)+; $^1$H NMR (CDCl$_3$) δ 1.89–2.10 (m, 2H), 2.75 (m, 1H), 3.30 (ddd, 2H), 4.40 (t, 1H), 5.24 (m, 1H), 7.20–7.70 (m, 23H +CHCl$_3$), 8.23 (m, 2H).

Step K:
2-O-((1,1-dimethylethyl)diphenylsilyl)-3-(((1,1dimethylethyl)-diphenylsilyl)oxymethyl-1,2-cyclobutanediol 2-Benzoyloxy-1-(((1,1-dimethylethyl)diphenylsilyl)oxy)-4-(((1,1-dimethyl-ethyl)diphenylsilyl)oxymethyl)-cyclobutane (4.2 g, 6.0 mmol) from Step J was dissolved in freshly distilled THF and the resultant solution was cooled to −78° C., with stirring, under a nitrogen atmosphere. Lithium triethylborohydride (20 mL of a 1M solution in THF, 20 mmol) was added and the reaction mixture was allowed to warm to 0° C. After stirring at 0° C. for 0.5 h, the reaction mixture was cooled to −78° C. and quenched with 1.2 mL of glacial acetic acid and concentrated in vacuo. The residue was triturated with ~50 mL of hexane, filtered and suspended in hexane. The suspension was applied to a 2.8×55 cm silica gel column which was eluted @ 2 psi with 1 L of 2% acetone in hexane to give 2.3 g (64% yield) of the title compound; $^1$H NMR (CDCl$_3$) δ 1.88 (m, 2H), 2.54 (m, 1H), 2.97 (d, 1H), 3.24–3.39 (ddd, 2H), 4.15 (m, 1H), 4. 24 (t, 1H); MS DCI-NH$_3$ M/Z: 595 (M+H)+, 612 (M+NH$_4$)+.

Step L:
1-O-methanesulfonyl-2-(((1,1-dimethylethyl)diphenylsilyl)oxy)-3-(((1,1-dimethylethyl)di-phenylsilyl)oxymethyl)-1-cyclobutanol Freshly distilled triethylamine (1.28 g, 8.2 mmol) was dissolved in 75 mL of freshly distilled methylene chloride. To this solution was added 2.3 g (3.9 mmol) of 2-O-(((1,1-dimethylethyl)diphenylsilyl)-3-(((1,1-dimethylethyl)diphenyl-silyl)oxymethyl)-1,2-cyclobutanediol from Step K and the resultant solution was cooled to −78° C. with stirring, under a nitrogen atmosphere. Methanesulfonyl chloride (0.99 g, 8.2 mmol) was added and the reaction mixture was allowed to warm to ambient temperature. After 3.5 h, the reaction mixture was diluted with 125 mL of methylene chloride and this solution was washed with 100 mL of water, dried over anhydrous magnesium sulfate, filtered and concentrated in vacuo. The residue (2.9 g) was dissolved in 25 mL of 10% acetone in hexane and purified on a 2.5×45 cm silica gel column eluted at 2 psi with 500 mL of 10% acetone in hexane, followed by 250 mL of 10% acetone in hexane, to give 1.57 g (60% yield) of the title compound; MS DCI-NH$_3$ M/Z: 690 (M+NH$_4$)$^+$; $^1$H NMR (CDCl$_3$) δ 1.95, m, 1H), 2.20 (m, 1H), 2.77 (m, 1H), 2.90 (s, 3H), 3.39 (d, 2H), 4.39 (m, 1H), 4.88 (m, 1H), 7.30–7.54 (m, 15H), 7.60–7.70 (m, 5H).

Step M:
2-(((1,1-dimethylethyl)diphenylsilyl)oxy)-3-(((1',1'-dimethylethyl)-diphenylsilyl)oxymethyl)-1-azidocyclobutane 1-O-methanesulfonyl-2-(((1,1-dimethylethyl)diphenylsilyl)oxy)-3-(((1,1-dimethylethyl)diphenylsilyl)oxymethyl)-1-cyclobutanol (1.57 g, 2.3 mmol) from Step L and lithium azide (0.69 g, 14.1 mmol) were combined in 40 mL of anhydrous DMF. The reaction mixture was heated, with stirring, in an oil bath at 90° C. After stirring for 22.5 h at 90° C. the temperature was reduced to 80° C. and the reaction mixture was stirred at 80° C. for 16.5 h. The DMF was removed in vacuo @ 50° C. The residue was dissolved in 200 mL of diethyl ether and the ether solution was washed with 100 mL of 5% aqueous sodium bicarbonate solution and 100 mL of water, dried over anhydrous magnesium sulfate, filtered and concentrated under reduced pressure. The residue (1.34 g) was dissolved in 25 mL of 10% acetone in hexane solution and purified on a 1.5×45 cm silica gel column eluted at 2 psi with 150 mL of hexane, followed by 300 mL of 3% acetone in hexane, to give 812 mg (56% yield) of the title compound; MS DCI-NH$_3$ M/Z: 637 (M+NH$_4$)$^+$; $^1$H NMR (CDCl$_3$) δ 1.47 (m, 1H), 1.97–2.12 (m, 2H), 3.39 (d, 2H), 3.49 (m, 1H), 4.11 (t, 1H), 7.30–7.55 (m, 15H), 7.60–7.70 (m, 5H).

Step N:
2-(((1,1-dimethylethyl)diphenylsilyl)oxy)-3-(((1,1-dimethylethyl)-diphenylsilyl)oxymethyl)-1-aminocyclobutane 2-(((1,1-dimethylethyl)diphenylsilyloxy)-3-(((1,1-dimethylethyl)diphenyl-silyl)oxymethyl)-1-azidocyclobutane (800 mg, 1.29 mmol), the product of Step M, was dissolved in 20 mL of methanol. To this solution was added 200 mg of 5% palladium on carbon, followed by 420 mg of ammonium formate. The flask was stoppered and the reaction mixture was stirred at ambient temperature for 23 h. The reaction mixture was filtered and the filtrate concentrated under reduced pressure. The residue was dissolved in 200 mL of diethyl ether and the ether solution was washed with 100 mL of 5% aqueous sodium bicarbonate solution, dried over anhydrous magnesium sulfate, filtered and concentrated under reduced pressure to give 707 mg (92% yield) of the title compound; MS DCI-NH$_3$ M/Z: 594 (M+H)$^+$; $^1$H NMR (CDCl$_3$) δ 0.88–1.08 (m, 18H), 1.95–2.15 (m, 3H), 3.01 (q, 1H), 3.5 (m, 2H), 3.68 (t, 1H).

Step O:
2-Amino-4-hydroxy-5-nitro-6-(2'-(((1,1-dimethylethyl)-diphenylsilyl)oxy)-3'-(((1,1-dimethylethyl)diphenyl-silyl)oxymethyl)cyclobutylamino)pyrimidine 2-(((1,1-dimethylethyl)diphenylsilyl)oxy)-3-(((1,1-dimethylethyl)diphenyl-silyl)oxymethyl)-1-aminocyclobutane (588 mg, 0.99 mmol), the product of Step N, 189 mg (0.99 mmol) of 2-amino-6-chloro-4-hydroxy-5-nitropyrimidine (prepared as described by J. F. Constant, et al. in J. Heterocyclic Chem, 1035 (1985)) and triethylamine (220 μL, 1.50 mmol) were combined in 5 mL of anhydrous DMF. The reaction mixture was stirred in an oil bath at 50° C. under a nitrogen atmosphere for 2.5 h. Diethyl ether (200 mL) was added and the ether solution was washed with 2×50 mL of water, dried over anhydrous magnesium sulfate, filtered and concentrated in vacuo. The residue (800 mg) was dissolved in methylene chloride and purified on a 1.0×45 cm silica gel column eluted @ 10 psi with 100 mL of methylene chloride, followed by 100 mL of 2% methanol in methylene chloride and finally 100 mL of 4% methanol in methylene chloride, to give 473 mg (64% yield) of the title compound; MS DCI-NH$_3$ M/Z: 748 (M+H)$^+$; $^1$H NMR (CDCl$_3$) δ 2.13–2.33 (m, 3H), 2.89 (s, 1H), 2.97 (s, 1H), 3.59–3.70 (m, 2H), 4.26 (t, 1H), 4.65 (m, 1H), 7.30–7.47 (m, 10H), 7.56–7.60 (m, 10H).

Step P:
9-(2'-hydroxy-3'-hydroxymethyl-1'-cyclobutyl)guanine

2-Amino-4-hydroxy-5-nitro-6-(2'-(((1,1-dimethylethyl)diphenylsilyl)oxy)-3'-(((1,1-dimethylethyl)diphenylsilyl)oxymethyl)cyclobutylamino)pyrimidine (470 mg, 0.63 mmol), the product of Step O, was dissolved in warm, degassed formic acid, under an argon atmosphere and the resultant solution was stirred at ambient temperature. Zinc dust (1.57g, 24 mmol) was added in one portion and stirring was continued. After approximately 3 h, the reaction mixture was filtered through a millipore 0.45 μ filter. The solid was washed with formic acid. The formic acid solution (40 mL) was heated in a bomb under argon for 3 h at 130° C. and then evaporated in vacuo. The residue was suspended in 15 mL of water and concentrated in vacuo three times. The residue was then resuspended in 20 mL of water (pH of aqueous solution ∼6) and the suspension was filtered by suction. The filter cake was dissolved in 10 mL of concentrated ammonium hydroxide solution and this solution was concentrated in vacuo. The residue from the ammonia solution was then suspended in water and reconcentrated. The residue (238 mg) was dissolved in 45 mL of water and treated with ∼50 mg of Darco G-60 ® activated charcoal at 50°–60° C. The charcoal was filtered while the suspension was still hot and washed with water. The filtrate was concentrated in vacuo @85° C. and the residue was redissolved in 25 mL of water. The aqueous solution was allowed to cool slowly overnight, then it was cooled to 3° C. for 1–2 h. The first crop of crystals were collected by suction filtration and dried in vacuo at 45° C. to give mg (53% yield) of the title compound; MS DCI-NH$_3$ M/Z: 252(M+H)$^+$, 269 (M+NH$_4$)$^+$; $^1$H NMR (d6-DMSO) δ 1.65 (q, 1H), 2.00 (m, 1H), 2.19 (q, 1H), 3.55 (m, 2H), 4.17 (q, 1H), 4.29 (q, 1H), 4.56 (t, 1H-OH), 5.55 (d, 1H-OH), 6.40 (bs, H, NH2), 7.70 (s, 1H).

EXAMPLE 43

9-(2'-Hydroxy-3'-hydroxymethyl-1'-cyclobutyl)adenine

Following the procedures in Example 4, replacing the product of Step E of Example 1 with 2-(((1,1-dimethylethyl)diphenylsilyl)oxy)-3-(((1,1-dimethylethyl)diphenylsilyl)oxymethyl)-1-aminocyclobutane, the product of Step N of Example 42, the title compound is prepared with the hydroxyl groups protected with the t-butyldiphenylsilyl group. The protecting groups are removed as described by S. Hanessian and P. Lavallee in *Canadian J. Chem*, 53, 2975–7 (1975).

EXAMPLE 44

1-(2'-Hydroxy-3'-hydroxymethyl-1'-cyclobutyl)uracil

Following the procedures described in Example 2, replacing the product of Step D of Example 1 with 2-(((1,1-dimethylethyl)diphenylsilyl)oxy)-3-(((1,1-dimethylethyl)diphenyl-silyl)oxymethyl)-1aminocyclobutane, the product of Step N of Example 42, the title compound is prepared.

EXAMPLE 45

1-(2'-Hydroxy-3'-hydroxymethyl-1'-cyclobutyl)thymine

Following the procedures described in Example 2, replacing, in Step A, the product of Step D of Example 1 with 2-(((1,1-dimethylethyl)diphenylsilyl)oxy)-3-(((1,1-dimethylethyl)diphenylsilyl)oxymethyl)-1-aminocyclobutane, the product of Step N of Example 42, and replacing, in Step B, (E)-3-ethoxyacryloyl chloride with 3-methoxymethacrylic acid chloride, the title compound is prepared.

EXAMPLE 46

1-(2'-Hydroxy-3'-hydroxymethyl-1'-cyclobutyl)cytosine

Following the procedures described in Example 3, replacing the product of Step B of Example 2 with the product of Example 44, the title compound is prepared.

EXAMPLE 47

9-(3,3-Bis(hydroxymethyl)-cyclobutyl)guanine

Step A:
3.3-Bis(hydroxymethyl)-1,1-dimethoxycyclobutane

Diisopropyl 3,3-dimethoxy-cyclobutane-1,1-dicarboxylate (6.0 g, 20.8 mmol), prepared as described by P. E. Pigou and C. H. Schiesser, *J Org Chem*, 53, 3841–3 (1988), was dissolved in 200 mL of anhydrous diethyl ether and the ether solution was cooled to 0° C. with stirring under a nitrogen atmosphere. Lithium aluminum hydride (1.6 g, 42 mmol) was added to the ether solution in portions and the reaction mixture was stirred at 0° C. for 0.5 h. The reaction was then quenched by the addition of 1.6 mL of water, followed by 1.6 mL of 15% aqueous sodium hydroxide solution and 4.8 mL of water. The reaction mixture was filtered, the filter cake washed with diethyl ether and the combine ether filtrates were concentrated under reduced pressure. The residue (3.0 g) was dissolved in 2 mL of methylene chloride and purified on a 1.5×45 cm silica gel column eluted @ 2–3 psi with 200 mL of acetone:hexane (1:2 v/v), followed by 200 mL of acetone:hexane (1:1 v/v) to give 1.51 g (41% yield) of the title compound; MS DCI/NH$_3$ M-Z: 194 (M+NH$_4$)+; $^1$H NMR (CDCl$_3$) δ 1.99 (s, 4H), 2.35 (t, 2H-OH), 3.16 (s, 6H), 3.77 (d, 4H).

Step B:
3,3-Bis(((1,1-dimethylethyl)dimethylsilyl)oxymethyl)-cyclobutanone-O-methyl oxime 3,3-Bis(hydroxymethyl)-1,1-dimethoxycyclobutane (1.35 g, 7.65 mmol) from Step A and 3.8 mL of 2M aqueous hydrochloric acid solution were added to 60 mL of THF and the reaction mixture was stirred at ambient temperature for 0.5 h, under a nitrogen atmosphere. The reaction mixture was neutralized by the addition of a strongly basic hydroxide resin then filtered and concentrated in vacuo. The residue was washed with THF and dissolved in 30 mL of anhydrous pyridine. To this solution was added 767 mg (9.2 mmol) of methoxylamine hydrochloride and the resultant solution was stirred for ~20 h at ambient temperature, under a nitrogen atmosphere. t-Butyldimethylsilyl chloride (3.5 g, 23 mmol) and 60 mL of anhydrous pyridine were then added and stirring continued overnight. The bulk of the solvent was evaporated in vacuo at 35°–40° C. and the concentrate dissolved in 200 mL of methylene chloride. The methylene chloride solution was washed with 100 mL of water, dried over anhydrous magnesium sulfate, filtered and concentrated in vacuo. The residue was purified on a 1.5×50 cm silica gel column eluted @ 5 psi with 200 mL of hexane, followed by 200 mL of 2% acetone in hexane, followed by 200 mL of 3% acetone in hexane, followed by 200 mL of 4% acetone in hexane and finally 200 mL of 10% acetone in hexane, to give 583 mg (20% yield) of the title compound; MS DCI-NH$_3$ M/Z: 388 (M+H)+; $^1$H NMR (CDCl$_3$) δ 0.04 (s, 12H), 0.87 (s, 18H), 2.61 (d, 4H), 3.58 (s, 4H), 3.82 (s, 3H).

Step C:
3.3-Bis(((1,1-dimethylethyl)diphenylsilyl)oxymethyl)-cyclobutylamine Following the procedures described in detail in Step G of Example 25, replacing the product of Step F of Example 25 with the product of Step B above, the O-methyl oxime is reduced to the title compound.

Step D:
2-Amino-4-hydroxy-5-nitro-6-(3',3'-bis(((1,1-dimethylethyl)dimethyl-silyl)oxymethyl)-cyclobutylamino)-pyrimidine Following the procedures described in Step H of Example 25, replacing the product of Step G of Example 25 with the product of Step C above, the title compound is prepared.

Step E: 9-(3,3-Bis(hydroxymethyl)cyclobutyl)guanine

Following the procedures described in Step I of Example 25, replacing the product of Step H of Example 25 with the product of Step D above, the title compound is prepared.

EXAMPLE 48

9-(3,3-Bis(hydroxymethyl)-cyclobutyl)adenine

Following the procedures in Example 4, replacing the product of Step E of Example 1 with 3,3-bis(((1,1-dimethylethyl)dimethylsilyl)oxymethyl)-cyclobutylamine, the product of Step C of Example 47, the title compound is prepared.

EXAMPLE 49

9-(3.3-Bis(hydroxymethyl)cyclobutyl)uracil

Following the procedures described in Example 2, replacing the product of Step D of Example 1 with 3,3-bis(((1,1-dimethylethyl)diphenylsilyl)oxymethyl)-cyclobutylamine, the product of Step C of Example 47, the title compound is prepared.

EXAMPLE 50

9-(3,3-Bis(hydroxymethyl)-cyclobutyl)thymine

Following the procedures described in Example 2, replacing, in Step A, the product of Step D of Example 1 with 3,3-bis(((1,1-dimethylethyl)dimethylsilyl)oxymethyl)cyclobutylamine, the product of Step C of Example 47, and replacing, in Step B, (E)-3-ethoxyacryloyl chloride with 3-methoxymethacrylic acid chloride, the title compound is prepared.

EXAMPLE 51

9-(3,3-Bis(hydroxymethyl)-cyclobutyl)cytosine

Following the procedures described in Example 3, replacing the product of Step B of Example 2 with the product of Example 49, the title compound is prepared.

EXAMPLE 52

9-(3'-Hydroxycyclobutyl)adenine

Step A: N-(Benzyloxycarbonyl)-3-amino-1-cyclobutanone

N-(Benzyloxycarbonyl)-3-methylenecyclobutanamine (4 g, 18.4 mmol) from Step A of Example 5, 34 mL of methanol and 136 mL of methylene chloride were mixed together and cooled to $-78°$ C. under a nitrogen atmosphere. Ozone was bubbled through the mixture for approximately 20 minutes and then the reaction mixture was flushed with nitrogen for approximately 10 minutes. Dimethyl sulfide (17 mL) was added to the reaction mixture and the reaction mixture was then stirred for 0.5 h at $-78°$ C. and 0.5 h at ambient temperature. The reaction mixture was concentrated under reduced pressure to a syrup. The syrup (6.2 g) was purified on a $1.5 \times 40$ cm silica gel column, rinsed with hexane and eluted @ 5 psi with 400 mL of 25% acetone in hexane to give 3.74 g (93% yield) of the title compound; MS DCI-NH$_3$ M/Z: 237 (M+NH$_4$)+; $^1$H NMR (CDCl$_3$) δ 3.10 (m, 2H), 3.43 (m, 2H), 4.31 (m, 1H), 5.13 (s, 2H), 7.45 (s, 5H).

Step B: N-(Benzyloxycarbonyl)-3-amino-1-cyclobutanol

N-(Benzyloxycarbonyl)-3-amino-1-cyclobutanone (3.51 g, 16.0 mmol) from Step A was dissolved in 100 mL of THF and the THF solution was cooled to $-78°$ C. with stirring under a nitrogen atmosphere. To the solution was added 17.6 mL (17.6 mmol) of potassium tri-sec-butylborohydride (sold by Aldrich Chemical Company as a 1M solution in THF under the registered trademark K-Selectride ®) and stirring was continued for 10 minutes. The reaction mixture was allowed to warm to 0° C. and then quenched with 1.16 mL (1 equivalent) of glacial acetic acid. The reaction mixture was then filtered through Celite filter aid and concentrated in vacuo. The residue (3.1 g) was dissolved in ~10 mL of methylene chloride and purified on a $1.5 \times 45$ cm silica gel column eluted @ 5 psi with 250 mL of acetone:hexane (1:2 v/v), followed by 200 mL of acetone:hexane (1:1 v/v) to give 2.22 g (63% yield) of the title compound; MS DCI-NH$_3$ M/Z: 222 (M+H)+, 239 (M+NH$_4$)+; $^1$H NMR (CD$_3$OD) δ 1.81 (m, 2H), 2.62 (m, 2H), 3.60 (m, 1H), 3.90 (m, 1H), 5.09 (s, 2H), 7.25-7.40 (m, 5H).

Step C: 3-(Benzyloxycarbonylamino)-1-(((1,1-dimethylethyl)-dimethylsilyl)oxy)-cyclobutane N-(Benzyloxycarbonyl)-3-amino-1-cyclobutanol (2.22 g, 10 mmol) from Step B and t-butyldimethylsilyl chloride (4.8 g, 32 mmol) were combined in 25 mL of anhydrous pyridine and the cloudy suspension was stirred over the weekend at ambient temperature, under a nitrogen atmosphere. After 65 h, the solution was concentrated in vacuo at 35°-40° C. The concentrate was diluted with 250 mL of methylene chloride and the methylene chloride solution was washed with $3 \times 100$ mL of water, dried over anhydrous magnesium sulfate and concentrated in vacuo. The residue (3.9 g) was purified on a $1.0 \times 45$ cm silica gel column eluted @ 5 psi with 100 mL of hexane, followed by 200 mL of 10% acetone in hexane to give 3.16 g (88% yield) of the title compound; MS DCI-NH$_3$ M/Z: 336 (M+H)+, 353 (M+NH$_4$)+; $^1$H NMR (CDCl$_3$) δ −0.03 (s, 6H), 0.83 (s, 9H), 1.75 (m, 2H), 2.68 (m, 2H), 3.69 (m, 1H), 3.93 (m, 1H), 5.06 (s, 2H), 7.30 (m, 5H).

Step D: 3-Amino-1-(1,1-dimethylethyl)dimethylsilyl)oxy)cyclobutane 3-(Benzyloxycarbonylamino)-1-(1,1-dimethylethyl)-dimethylsilyl)oxy)-cyclobutane (3.16 g, 9.4 mmol) from Step C was dissolved in 75 mL of methanol and 0.1 g of 10% palladium on carbon was added. The reaction mixture was stirred under hydrogen at ambient temperature and atmospheric pressure for 3 h. The catalyst was removed by filtration through a Millepore 0.45 μm filter and the filtrate was concentrated under reduced pressure to give a quantitative yield of the title compound; MS DCI-NH$_3$ M/Z: 202 (M+H)+, 219 (M+NH$_4$)+; $^1$H NMR (CDCl$_3$) δ −0.03 (s, 6H), 0.83 (s, 9H), 1.60 (m, 2H), 2.60 (m, 2H), 2.85 (m, 1H), 3 33 (m, 1H).

Step E: 5-Amino-4-chloro-6-(3'-(((1,1-dimethylethyl)dimethylsilyl)oxy)-1'-cyclobutylamino)pyrimidine 3-Amino-1-((1,1-dimethylethyl)dimethylsilyl)oxy)cyclobutane (1.9 g, 9.4 mmol) from Step D, 5-amino-4,6-dichloropyrimidine (2.3 g, 14.1 mmol) and triethylamine (6.57 mL (47 mmol) were combined in 100 mL of n-butanol and the reaction mixture was heated at reflux temperature under a nitrogen atmosphere for 24 h. An additional 4 mL of triethylamine was added and reflux was continued for 5 h. The reaction mixture was concentrated in vacuo and the residue was eluted with 20% water in methanol through a $1.5 \times 33$ cm column of strongly basic resin (60 mL) which had been packed with the same solvent. The eluate from the column was concentrated in vacuo. The residue (3.9 g) was dissolved in ~25 mL of methylene chloride and purified on a $1.8 \times 50$ cm silica gel column eluted with 250 mL of methylene chloride, followed by 250 mL of 1% methanol in methylene chloride, followed by 250 mL of 2% methanol in methylene chloride and finally 250 mL of 3% methanol in methylene chloride, to give 2.8 g (91% yield) of the title compound; MS DCI-NH$_3$ M/Z: 329

(M+H)+; 1H NMR (CDCl3) δ −0.03 (m, 6H), 0.83 (m, 9H), 1.80 (m, 2H), 2.80 (m, 2H), 3.30 (bs, 2H-NH2), 4.02 (m, 1H), 8.0 (s, 1H).

Step F: 9-(3'-Hydroxy-1'-cyclobutyl)-6-chloropurine

5-Amino-4-chloro-6-(3'-(((1,1-dimethylethyl)dimethylsilyl)oxy)-1'-cyclobutyl-amino)pyrimidine (2.8 g, 8.5 mmol) from Step E and 75 mL of diethoxymethyl acetate were combined under a nitrogen atmosphere and the mixture was heated at reflux temperature for approximately 22 h then concentrated to an oil. The oil was dissolved in 50 mL of toluene and 100 mg of p-toluenesulfonic acid was added. The resultant solution was stirred at ambient temperature for 1 h then concentrated in vacuo. The residue was dissolved in 75 mL of methanol which had been saturated with ammonia at 0° C. The solvents were evaporated and three 10 mL portions of methanol were added to the residue and evaporated. The residue was then dissolved in 75 mL of methanol and the pH of the solution was adjusted to ∼3 with p-toluenesulfonic acid. The solution was stirred at ambient temperature for approximately 1 h and then neutralized with methanol saturated with ammonia and concentrated. The residue was dissolved in ∼1 mL of methylene chloride and purified on a 1.5×45 cm silica gel column eluted @ 5 psi with 200 mL of methylene chloride, followed by 200 mL of 5% methanol in methylene chloride and finally 10% methanol in methylene chloride to give 1.50 g (79% yield) of the title 7( compound; MS DCI-NH3 M/Z: 225 (M+H)+, 242 (M+NH4)+; 1H NMR (CD3OD) δ 2.66 (m, 2H), 3.10 (m, 2H), 4.22 (m, 1H), 4.72 (m, 1H), 6.68 (s, 1H), 8.73 (s, 1H).

Step G: 9-(3'-Hydroxycyclobutyl)adenine 9-(3'-Hydroxy-1'-cyclobutyl)-6-chloropurine (0.8 g, 3.56 mmol) from Step F and 20 mL of condensed ammonia were combined with 10 mL of methanol in a tube. The tube was sealed and heated at 60° C. for 41 h then cooled to −78° C. and opened. The solution was evaporated to a solid residue which was triturated with 10 mL of methanol at 65° C. The mixture was cooled to 4° C. and the solvent removed by decantation. The solid was dried in vacuo to give 654 mg (89% yield) of the title compound; MS DCI-NH3 M/Z: 206 (M+H)+; 1H NMR (CD3OD) δ 2.54 (m, 2H), 3.00 (m, 2H), 4.19 (m, 1H), 4.60 (m, 1H), 8.20 (s, 1H), 8.24 (s, H).

EXAMPLE 53

9-(3'-((Phosphonyl)methoxy)cyclobutyl)adenine ammonium salt

Step A:
9-(3'((Diethylphosphonyl)methoxy)cyclobutyl)adenine

A mixture of 378 mg (1.84 mmol) of 9-(3'-hydroxycyclobutyl)adenine, the product of Example 52, in 100 mL of freshly distilled THF was cooled to 0° C. and treated with 62 mg (2.6 mmol) of sodium hydride. After 10 minutes, 718 mg (2.4 mmol) of diethyl phosphonomethyl triflate was added and stirring was continued at 0° C. for 4.5 h under a nitrogen atmosphere. At this time an additional 200 μL of diethyl phosphonomethyl triflate was added and the stirring was continued again. After 6 h, the reaction was quenched with methanol and concentrated in vacuo. The residue was dissolved in 2 mL of methylene chloride and applied to a 1.0×45 cm silica gel column eluted @ 5 psi with 100 mL of methylene chloride, followed by 100 mL of 3% methanol in methylene chloride, followed by 100 mL of 5% methanol in methylene chloride and finally 100 mL of 10% methanol in methylene chloride, to give, after all of the fractions containing the desired product were combined and concentrated,222 mg (34% yield) of the title compound; MS DCI-NH3 M/Z: 356 (M+H)+; 1H NMR (CDCl3) δ 1.38 (t, 6H), 2.60 (m, 2H), 3.07 (m, 2H), 3.79 (m, 2H), 4.11 (m, 1H), 4.21 (m, 4H), 4.68 (m, 1H), 7.97 (s, 1H), 8.35 (s, 1H).

Step B:
9-(3'-((Phosphonyl)methoxy)cyclobutyl)adenine ammonium salt

A mixture of 286 mg (0.806 mmol) of the diethyl ester from the previous step was dissolved in 5 mL of acetonitrile and treated with 1.01 mL (8.1 mmol) of bromotrimethylsilane at ambient temperature under a nitrogen atmosphere for 21 h. The reaction mixture was concentrated in vacuo, taken up in 5 mL of water and again concentrated. The residue was dissolved in 1 mL of concentrated aqueous ammonium hydroxide solution and the resultant solution was concentrated in vacuo. The residue was dissolved in 2 mL of water and purified on a 1.5×45 cm reverse phase column of Bondesil® C18 (40 μm particles) packed with methanol, equilibrated with water @ 10 psi and eluted with water @ 10 psi to give 122 mg (45% yield) of the title compound as the ammonium salt; MS DCI-NH3 M/Z: 300 (M+H)+ free acid; 1H NMR (D2O) δ 2.52 (m, 2H), 3.06 (m, 2H), 3.64 (d, 2H), 4.17 (m, 1H), 4.55 (m, 1H), 8.13 (s, 1H), 8.27 (s, 1H).

EXAMPLE 54

9-(3'-Hydroxycyclobutyl)guanine

Following the procedures described in Steps O and P of Example 42, replacing the product of Step N of Example 42 with 3-amino-1-(1,1-dimethylethyl)dimethylsilyl)oxy)cyclobutane, the product of Step D of Example 52, the title compound is prepared.

EXAMPLE 55

9-(3'-Hydroxycyclobutyl)uracil

Following the procedures described in Example 2, replacing the product of Step D of Example 1 with 3-amino-1-(1,1-dimethylethyl)dimethylsilyl)oxycyclobutane, the product of Step D of Example 52, the title compound is prepared.

EXAMPLE 56

9-(3'-Hydroxycyclobutyl)thymine

Following the procedures described in Example 2, replacing, in Step A, the product of Step D of Example 1 with 3-amino-1-(1,1-dimethylethyl)dimethylsilyl)oxycyclobutane, the product of Step F of Example 55, and replacing, in Step B, (E)-3-ethoxyacryloyl chloride with 3-methoxymethacryloyl chloride, the title compound is prepared.

EXAMPLE 57

9-(3'-Hydroxycyclobutyl)cytosine

Following the procedures described in Example 3, replacing the product of Step B of Example 2 with the product of Example 55, the title compound is prepared.

EXAMPLE 58

9-(3'-Hydroxy-2'-hydroxymethyl-1'-cyclobutyl)cyanine

Step A: 2-Amino-6-chloro-9-(3', 3'-diethoxy-2'-methoxycarbonyl-1'-cyclobutyl)purine Methyl 4,4-diethoxy-1-cyclobutenecarboxylate (2.3 g, 11.5 mmol), prepared as described by M. F. Semmelhack, et al. in *J Am Chem Soc.* 104, 747–759 (1982), was dissolved in 50 mL of DMF and 1.95 g (11.5 mmol) of 2-amino-6-chloropurine was added, followed by 50 μL of 1,8-diazabicyclo[5.4.0]undec-7-ene (DBU). The solution was stirred at ambient temperature for 1 h and 0.5 mL of DBU was added and stirring continued for 0.5 h. The reaction mixture was stirred for an additional 2 h and then stored in the refrigerator overnight. The reaction mixture was then concentrated and the residue purified on a silica gel column eluted with 2% methanol in methylene chloride to give 2.9 g (70% yield) of the title compound; MS DCI-NH$_3$ M/Z: 371 (M+H)$^+$, 388 (M+NH$_4$)$^+$.

Step B: 2-Amino-6-chloro-9-(3', 3'-diethoxy-2'-hydroxymethyl-1'-cyclobutyl)-purine 2-Amino-6-chloro-9-(3',3'-diethoxy-2'-methoxycarbonyl-1'-cyclobutyl)purine (1.9 g, 5.1 mmol) from Step A was dissolved in 70 mL of THF and cooled to 0° C. in an ice water bath. Lithium aluminum hydride (280 mg, 1.5 equivalents) was added to the solution in small batches over a 30 min period. The reaction mixture was stirred at 0° C. for 1.5 h and then the reaction was quenched by the addition of 0.4 mL of water, followed by 0.4 mL of 15% aqueous sodium hydroxide solution and 1.2 mL of water. The reaction mixture was then stirred vigorously for 20 min at ambient temperature. The aluminum salts were filtered through Celite filter aid and the filtrate was concentrated under reduced pressure to give 1.67 g of the title compound as a white solid; MS DCI-NH$_3$ M/Z: 343 (M+H)$^+$, 360 (M+NH$_4$)$^+$.

Step C: 2-Amino-6-chloro-9-((3'-oxo-2'-hydroxymethyl)-1'-cyclobutyl)purine

2-Amino-6chloro-9-(3',3'-diethoxy-2'-hydroxymethyl-1'-cyclobutyl)purine (1.3 g) from Step B and acetone (70 mL) and 10 mL of 1N hydrochloric acid solution were combined and stirred at ambient temperature for 4 h. At this time 5 mL of 1M hydrochloric acid was added and stirring continued overnight. After 18 h another 5 mL portion of 1N hydrochloric acid solution was added. The reaction mixture was then neutralized with 1N sodium hydroxide solution and extracted with 3×200 mL of ethyl acetate. The ethyl acetate solution was concentrated and the residue was purified on a silica gel column eluted with 10% methanol in methylene chloride to give 470 mg of the title compound; MS DCI-NH$_3$ M/Z: 269 (M+H)$^+$, 286 (M+NH$_4$)$^+$.

Step D: 2-Amino-6-chloro-9-(3'-hydroxy-2'-hydroxymethyl-1'-cyclobutyl)-purine 2-Amino-6-chloro-9-(3'-oxo-2'-hydroxymethyl-1'-cyclobutyl)purine (430 mg) from Step C was dissolved in 45 mL of methanol and the resultant solution was cooled to 0° C. Sodium borohydride was added to the solution portionwise and the reaction mixture was stirred for 15 min at 0° C. The reaction was then quenched by the addition of acetone. The reaction mixture was concentrated and the residue was purified on a silica gel column eluted with 10% methanol in methylene chloride to give 370 mg of the title compound; MS DCI-NH$_3$ M/Z: 270 (M+H)$^+$, 287 (M+NH$_4$)$^+$.

Step E: 9-((3'-Hydroxy-2'-hydroxymethyl)-1'-cyclobutyl)guanine

2-Amino-4-chloro-9-((3'-hydroxy-2'-hydroxymethyl-1'-cyclobutyl)purine (78 mg) from Step D and 5 mL of 1N hydrochloric acid were combined and heated at 105° C. for 2.5 h. The reaction mixture was concentrated in vacuo to give 62 mg of the title compound; MS DCI-NH$_3$ M/Z: 252 (M+H)$^+$, 269 (M+NH$_4$)$^+$; $^1$H NMR (d6-DMSO) δ 2.40 (m, 1H), 2.62–2.80 (m, 2H), 3.55 (m, 2H), 3.78 (m, 1H), 4.12 (m, 1H), 4.66 (t, 1H, J=5.5 Hz), 5.22 (d, 1H, J=7.0 Hz), 6.40 (bs, 2H), 7.82 (s, 1H), 10.50 (bs, 1H).

EXAMPLE 59

9-(2'-(Hydroxymethyl)-3'-((phosphonyl)methoxy)-1'-cyclobutyl)guanine

Step A: 2-Amino-6-chloro-9-(3'-hydroxy-2'-(((1,1-dimethylethyl)dimethyl)dimethylsilyloxy)methyl)-1'-cyclobutyl)-purine 2-Amino-6-chloro-9-(3'-hydroxy-2'-hydroxymethyl-1'-cyclobutyl)purine (390 mg, 1.45 mmol), the product of Step D of Example 58 was dissolved in 10 mL of DMF and the solution was cooled to 0° C. t-Butyldimethylsilyl chloride (240 mg, 1.1 equivalents) and imidazole (200 mg, 1.1 equivalents) were added sequentially and the reaction mixture was stirred at 0° C. for 1.25 h. The reaction mixture was concentrated and the residue was chromatographed on a silica gel column eluted with 5% methanol in methylene chloride to give 140 mg of the title compound; $^1$H NMR (d6-DMSO) δ ~0.04 (s, 6H), 0.73 (s, 9H), 2.19 (m, 1H), 70 (m, 1H), 2.90 (m, 1H), 3.70 (m, 1H), 3.78 (m, 2H), 4.20 (m, 1H), 32 (d, 1H-OH), 6.81 (bs, 2H-NH$_2$), 8.29 (s, 1H); MS DCI-NH$_3$ M/Z: 384 (M+H)$^+$, 401 (M+NH$_4$)$^+$.

Step B: 2-Amino-6-chloro-9-(3'-((diethylphosphonyl)methoxy)-2'-(((1,1-dimethylethyl)dimethylsilyloxy)methyl)-1'-cyclobutyl)-purine A suspension of sodium hydride (18.5 mg) in 10 mL THF was cooled to 0° C. and 155 mg (0.42 mmol) of 2-amino-6-chloro-9-(3'-hydroxy-2'-(((1,1-dimethylethyl)dimethylsilyloxymethyl)-1'-cyclobutyl)purine from Step A was added, followed after 10 minutes by 108 μL of diethyl phosphonomethyl triflate. After stirring the reaction mixture for 1 h, the reaction was quenched by the addition of methanol and the reaction mixture was concentrated under reduced pressure. The residue was purified on a silica gel column eluted with 2% methanol in methylene chloride to give 170 mg (80% yield) of the title compound; $^1$H NMR (d6-DMSO) δ ~0.02 (2s, 6H), 0.77 (s, 9H), 2.38 (m, 1H), 2.75 (m, 1H), 3.07 (m, 1H), 3.76 (d, 2H), 3.78–3.92 (m, 3H), 4.35 (m, 1H), 6.88 (bs, 2H-NH2), 8.31 (s, 1H); MS DCI-NH$_3$ M/Z: 534 (M+H)$^+$, 551 (M+NH$_4$)$^+$.

Step C: 2-Amino-6-bromo-9-(3'-((diethylphosphonyl)methoxy)-2'-hydroxymethyl)-1'-cyclobutyl)purine 2-Amino-6-chloro-9-(3'-((diethylphosphonyl)methoxy-2'-((1,1-dimethylethyl)-dimethylsilyloxy)methyl)-1'cyclobutyl)purine (169 mg, 0.32 mmol) from Step B was dissolved in 2 mL of acetonitrile and 420 mL of trimethylsilyl bromide was added. The faintly yellow solution was stirred at ambient temperature under an argon atmosphere for 16 h and then concentrated. The residue was dried and suspended in 2 mL of water. The water was removed in vacuo and this step was repeated. The residue was dissolved in methanol and reconcentrated then dissolved in THF and reconcentrated to give 170 mg of the title compound as a glassy pale yellow solid which was taken on to the next step without purification; FAB$^-$ MS: 408; FAB$^+$ MS: 410.

Step D:
9-((2'-Hydroxymethyl)-3'-((phosphonyl)methoxy)-1'-cyclobutyl)guanine 2-Amino-6-bromo-9-((3'-(phosphonyl)methoxy)-2'-hydroxymethyl)-1'-cyclobutyl)purine (170 mg) from Step C and 7 mL of 1 N hydrochloric acid were combined and heated at 90° C. for 2 h and 10 min. The reaction mixture was then allowed to cool to ambient temperature and was concentrated to dryness on the rotovap. The residue was reconstituted with water and evaporated to dryness twice then dissolved in 0.5 mL of concentrated aqueous ammonium hydroxide solution and again concentrated to dryness. The residue was purified on a reverse phase C-18 column eluted with water to give 101 mg of the title compound; MS FAB M/Z 346 (M+H)$^+$; $^1$H NMR (D$_2$O) δ 2.44 (m, 1H), 2.96 (m, 1H), 3.04 (m, 1H), 3.67 (d, 1H), 3.82 (d, 1H), 3.98 (m, 1H), 4.31 (m, 1H), 8.01 (s, 1H).

EXAMPLE 60

9-(3'-Hydroxy-2'-(hydroxymethyl)-1'-cyclobutyl)adenine

Following the procedures described in Steps A–D of Example 58, replacing 2-amino-6-chloropurine in Step A with adenine, the title compound was prepared; FAB MS M/Z: 236 (M+H)$^+$; $^1$H NMR (d6-DMSO) δ 2.32 (m, 1H), 2.72 (m, 1H), 2.84 (m, 1H), 3.56 (m, 2H), 3.82 (m, 1H), 4.30 (q, 1H), 4.79 (t, 1H), 5.31 (d, 1H), 8.12 (s, 1H), 8.24 (s, 1H).

EXAMPLE 61

9-(2'-(Hydroxymethyl)-3'-((phosphonyl)methoxy)-1'-cyclobutyl)adenine

Following the procedures described in Steps A–C of Example 59, replacing 2-amino-6-chloro-9-(3'-hydroxy-2'-hydroxymethyl-1'-cyclobutyl)purine in Step A with the product of Example 60, the title compound is prepared.

EXAMPLE 62

9-(2'-(2''-(Hydroxy)ethyl)-3'-(hydroxymethyl)-1'-cyclobutyl)guanine

Step A:
2-(2-(Hydroxy)ethyl)-3-(hydroxymethyl)cyclobutanol

2-Oxa-3-oxo-6-formyl-bicyclo[3.2.0]heptane (950 mg, 6.78 mmol), prepared as described by A. E. Greene, et al. in *Tetrahedron Letters*, 3755–8 (1976), was dissolved in 8 mL of anhydrous THF and the resultant solution was cooled to 0° C. After stirring the solution at 0° C. for 0.5 h, 27.2 mL (27.1 mmol) of diborane (1M solution in THF) was added and stirring was continued for another 0.5 h. The reaction was carefully quenched with methanol, concentrated in vacuo and dried in vacuo to give 800 mg (81% yield) of the title compound which was taken on to the next step without purification; MS DCI-NH$_3$ M/Z: 147 (M+H)$^+$, 164 (M+NH$_4$)$^+$.

Step B:
2-(2-(((1,1-Dimethylethyl)dimethylsilyl)oxy)ethyl)-3-(((1,1-dimethylethyl)dimethylsilyl)oxymethyl)cyclobutanol 2-(2-(Hydroxy)ethyl)-3-(hydroxymethyl)cyclobutanol (800 mg, 5.48 mmol) from Step A was mixed with 1.726 g (11.4 mmol) of t-butyldimethylsilyl chloride and 1.57 g (23 mmol) of imidazole in 18 mL of DMF:methylene chloride (1:8 v/V) and the reaction mixture was stirred at ambient temperature for 2 h under a nitrogen atmosphere. The reaction mixture was concentrated in vacuo and the residue dissolved in ethyl acetate. The ethyl acetate solution was washed with brine, dried over anhydrous sodium sulfate, filtered and concentrated. The residue was purified on a silica gel column eluted with 10% ethyl acetate in hexane to give 900 mg (44% yield) of the title compound; MS DCI-NH$_3$ M/Z: 375 (M+H)$^+$, 392 (M+NH$_4$)$^+$.

Step C:
2-(2-(((1,1-Dimethylethyl)dimethylsilyl)oxy)ethyl)-3-(((1 1-dimethylethyl)dimethylsilyl)oxymethyl)-1-O-methanesulfonylcyclobutanol 2-(2-(((1,1-Dimethylethyl)dimethylsilyl)oxy)ethyl)-3-(((1,1-dimethylethyl)dimethyl-silyl)oxymethyl)cyclobutanol (160 mg, 0.43 mmol) from Step B was dissolved in 2 mL of methylene chloride and the resultant solution was cooled to 0° C. Triethylamine (120μL) was added, followed by 36 μL of methanesulfonyl chloride. After stirring the reaction mixture for 30 min at 0° C., it was concentrated in vacuo and the residue was purified on a silica gel column eluted with 10% ethyl acetate in hexane to give 180 mg (89% yield) of the title compound.; MS DCI-NH$_3$ M/Z: 447 (M+H)$^+$, 464 (M+NH$_4$)$^+$.

Step D:
2-(2-(((1,1-Dimethylethyl)dimethylsilyl)oxy)ethyl)-3-(((1,1-dimethylethyl)dimethylsilyl)oxymethyl)-1-azidocyclobutane 2-(2-(((1,1-Dimethylethyl)dimethylsilyl)oxy-ethyl-3-(((1,1-dimethylethyl)dimethyl-silyl)oxymethyl)-1-O-methanesulfonylcyclobutanol (180 mg, 0.41 mmol) was mixed with 200 mg (4.1 mmol) of lithium azide in 4 mL of DMF. The reaction mixture was heated at 80° C. for 2 h then concentrated in vacuo. The residue was purified on a silica gel column eluted with 5% ethyl acetate in hexane to give 120 mg (73% yield) of the title compound; MS DCI-NH$_3$ M/Z: 400 (M+H)$^+$, 417 (M+NH$_4$)$^+$.

Step E:
2-(2-(((1,1-Dimethylethyl)dimethylsilyl)oxy)ethyl)-3-(((1,1-dimethylethyl)dimethylsilyl)oxymethyl)-1-aminocyclobutane 2-(2-(((1,1-Dimethylethyl)dimethylsilyl)oxy)ethyl)-3-(((1,1-dimethylethyl)dimethyl-silyl)oxymethyl)-1-azidocyclobutane (980 mg, 2.45 mmol), prepared as described in Step D above, was dissolved in 20 mL of methanol and an excess of palladium on carbon was added to the solution under a nitrogen atmosphere. The reaction mixture was stirred at ambient temperature and atmospheric pressure under hydrogen for 0.5 h. The catalyst was removed by filtration and washed with 10 mL of methanol. The filtrate was concentrated in vacuo to give 850 mg (93%) yield of the title compound; MS DCI-NH$_3$ M/Z: 374 (M+H)+, 391 (M+NH4)+.

Step F:
2-Amino-6-(2'-(2-(((1,1-dimethylethyl)dimethylsilyl)oxy)ethyl)-3'-((1,1-dimethylethyl)dimethylsilyl)oxymethyl)-1'-cyclobutylamino)-4-hydroxy-5-nitropyrimidine 2-(2-(((1,1-Dimethylethyl)dimethylsilyl)oxy)ethyl)-3-(((1,1-dimethylethyl)-dimethylsilyl)oxymethyl)-1-aminocyclobutane (820 mg, 2.2 mmol), from Step E, 6-chloro-2-amino-4-hydroxy-5-nitropyrimidine (450 mg, 2.35 mmol) and triethylamine (460 μL, 3.3 mmol) were mixed together in 25 mL of DMF and the reaction mixture was heated at 60° C. for 1 h. The reaction mixture was concentrated in vacuo and the residue was extracted with 3×100 mL of ethyl acetate. The ethyl acetate solution was washed with brine, dried over anhydrous sodium sulfate, filtered and concentrated. The residue was purified on a silica gel column eluted with 5% methanol in methylene chloride to give 860 mg (74% yield) of the title compound; MS DCI-NH$_3$ M/Z: 528 (M+H)+, 445 (M+NH$_4$)+.

Step G:
9-(2'-(2-(Hydroxy)ethyl)-3'-(hydroxymethyl)-1'-cyclobutyl)guanine

Following the procedures described in Step P of Example 42, replacing 470 mg (0.63 mmol) of 2-amino-4-hydroxy-5-nitro-6-(2'-(((1,1-dimethylethyl)diphenylsilyl)oxy)-3'-(((1,1-dimethylethyl)diphenylsilyl)oxymethyl)cyclobutylamino-pyrimidine with 460 mg (0.872 mmol) of 2-amino-6-(2'-(2-(((1,1-dimethylethyl)dimethylsilyl)oxy)ethyl)-3'-(((1,1-dimethylethyl)dimethylsilyl)oxymethyl)-1'- cyclobutylamino)-4-hydroxy-5-nitropyrimidine, from Step F, and heating the formic acid solution at 160° C. for 2.5 h, instead of at 130° C. for 3 h, the title compound was prepared (60 mg) in a 22% yield; MS DCI-NH$_3$ M/Z: 280 (M+H)+; $^1$H NMR (d6-DMSO) δ 1.65 (m, 1H), 1.89 (m, 1H), 2.04 (q, 1H), 2.37 (m, 1H), 2.55 (m, 1H), 3.28 (m, 2H), 3.52 (m, 2H), 4.26 (q, 1H), 4.37 (t, 1H-OH), 4.63 (t, 1H-OH), 6.39 (bs, 2H-NH2), 7.87 (s, 1H).

EXAMPLE 63

9-(2'-(2-Hydroxy)ethyl)-3'-hydroxymethyl-1'-cyclobutyl)adenine

Following the procedures in Example 4, replacing the product of Step E of Example 1 with 2-(2-(((1,1-dimethylethyl)dimethylsilyl)oxy)ethyl)-3-(((1,1-dimethylethyl)dimethylsilyl)oxymethyl)-1-aminocyclobutane, the product of Step E of Example 62, the title compound is prepared with the hydroxyl groups protected with the t-butyldimethylsilyl group. The protecting groups are removed as described in Step E of Example 1.

EXAMPLE 64

9-(2'-(2-(Hydroxy)ethyl)-3'-hydroxymethyl-1'-cyclobutyl)uracil

Following the procedures described in Example 2, replacing the product of Step D of Example 1 with 2-(2-(((1,1-dimethylethyl)dimethylsilyl)oxy)ethyl)-3-(((1,1-dimethylethyl)dimethylsilyl)oxymethyl)-1-aminocyclobutane, the product of Step E of Example 62, the title compound is prepared.

EXAMPLE 65

9-(2'(2-(Hydroxyl)ethyl)-3'-hydroxymethyl-1'-cyclobutyl)thymine

Following the procedures described in Example 2, replacing, in Step A, the product of Step D of Example 1 with 2-(2-(((1,1-dimethylethyl)dimethylsilyl)oxy)ethyl)-3-(((1,1-dimethylethyl)dimethylsilyl)oxymethyl)-1-aminocyclobutane, the product of Step E of Example 62, and replacing, in Step B, (E)-3-ethoxyacryloyl chloride with 3-methoxymethacryloyl chloride, the title compound is prepared.

EXAMPLE 66

9-(2'-(2-(Hydroxy)ethyl)-3'-hydroxymethyl-1'-cyclobutyl)cytosine

Following the procedures described in Example 3, replacing the product of Step B of Example 2 with the product of Example 64, the title compound is prepared.

EXAMPLE 67

4-Amino-9-bromo-7-(2',3'-bis(hydroxymethyl)cyclobutyl)-7H-pyrrolo[2.3-d]pyrimidine Step A:
3-((4'-Chloro-5'-(2.2-diethoxyethyl)-6'-pyrimidiyl)amino)-1,2-bis(hydroxymethyl)cyclobutane 2,3-Bis(hydroxymethyl)cyclobutylamine hydrochloride was generated by the procedures described in Step E of Example 1 from 4.32 g (12 mmol) of 2,3-bis(((1,1-dimethylethyl)dimethylsilyl)oxymethyl)cyclobutylamine, the product of Step D of Example 1 and added to a solution of 6.336 g (24 mmol) of 4,6-dichloro-5-(2,2-diethoxyethyl)pyrimidine, prepared as described by J. A. Montgomery and K. Hewson in *J Medicinal Chemistry*, 10, 665–7 (1967), in 30 mL of ethanol. Triethylamine (3.3 mL, 24 mmol) was added and the reaction mixture was heated at reflux for 7 h. An additional 1.5 mL of triethylamine was added and reflux continued for 0.5 h. The temperature was allowed to fall below reflux temperature and the solution was concentrated in vacuo to a solid residue. The residue was dissolved in methylene chloride and the methylene chloride solution was washed with aqueous sodium bicarbonate solution and brine, dried over anhydrous magnesium sulfate, filtered and concentrated. The residue was purified on a 2.8×73 cm silica gel column eluted with 5% methanol in methylene chloride followed by 10% methanol in methylene chloride to give 2.88 g (67% yield) of the title compound; MS DCI-NH$_3$ M/Z: 360 (M+H)+.

Step B:
4-Chloro-7-(2',3'-bis(hydroxymethyl)cyclobutyl)-7H-pyrrolo[2,3-d]pyrimidine 3-((4'-Chloro-5'-(2,2-diethoxyethyl)-6'-pyrimidinyl)amino)-1,2-bis(hydroxymethyl)cyclobutane (2.88 g, 8 mmol) from Step A was dissolved in 43 mL of dioxane and 10.8 mL of 1 N hydrochloric acid solution was added. The resultant solution was stirred at ambient temperature for 2 days and then 1.5 mL of concentrated aqueous ammonium hydroxide solution was added. The solution was concentrated in vacuo and ethanol added to the residue. The ethanol was evaporated and the residue was treated with 300 mL of warm chloroform.

The chloroform solution was filtered and the filtrate was washed with water (pH of water wash was ~4), sodium bicarbonate and brine, dried over anhydrous magnesium sulfate, filtered and concentrated in vacuo to give 1.75 g (82% yield) of the title compound; MS DCI-NH$_3$ M/Z: 268 (M+H)+; $^1$H NMR (CDCl$_3$) δ2.24 (m, 2H), 2.35 (m, 2H), 2.59–2.80 (m, 4H), 3.60–3.90 (m, 4H), 4.81 (q, 1H), 6.64 (d, 1H), 7.40 (d, 1H), 8.62 (s, 1H).

This product was carried on to the next step without purification.

Step C:
9-Bromo-4-chloro-7-(2',3'-bis(hydroxymethyl)cyclobutyl)-7H-pyrrolo[2,3-d]pyrimidine 4-Chloro-7-(2',3'-bis(hydroxymethyl)cyclobutyl)-7H-pyrrolo[2,3-d]pyrimidine (26 mg, 0.1 mmol) from Step B was treated with 26.7 mg (0.15 mmol) of N-bromosuccinimide (NBS) in 2.5 mL of chloroform, overnight at ambient temperature. An additional 28 mg of NBS and 2 mL of chloroform were then added and stirring was continued overnight. The mixture was partitioned between water and chloroform and the chloroform solution was washed with aqueous thiosulfate solution, dried over anhydrous magnesium sulfate, filtered and concentrated. The residue was purified on a 2.0×12 cm silica gel column eluted with 5% methanol in methylene chloride to give 8.4 mg (24% yield) of the title compound; MS DCI-NH$_3$ M/Z: 346 (M+H)+, 348 (MH+2)+; $^1$H NMR CD$_3$OD) δ2.20–2.33 (m, 2H), 2.50–2.60 (m, 1H), 2.75–2.85 (m, 1H), 3.65–3.71 (m, 4H), 5.03 (q, 1H), 7.93 (s, 1H), 8.57 (s, 1H).

Step D:
4-Chloro-7-(2',3'-bis(acetoxymethyl)cyclobutyl)-7H-pyrrolo[2.3-d]pyrimidine 4-Chloro-7-(2',3'-bis(hydroxymethyl)cyclobutyl)-7H-pyrrolo[2,3-d]pyrimidine (0.661 g (2.48 mmol) from Step B was treated with 0.612 g (567 μL, 6 mmol) of acetic anhydride in 5 mL of methylene chloride and 2 mL of pyridine at ambient temperature overnight. An additional 225 μL of acetic anhydride and 2 m L of pyridine were then added and stirring continued at ambient temperature. After 4 h, the solution was concentrated in vacuo and complete removal of solvents was achieved by azeotropic distillation in vacuo with toluene. The residue was purified on a 2×30 cm silica gel column eluted with 50% ethyl acetate in hexane to give 0.772 g (89% yield) of the title compound; MS DCI-NH$_3$ M/Z: 352 (M+H)+; $^1$H NMR (CDCl$_3$) δ1.98 (s, 3H), 2.13 (s, 3H), 2.39 (m, 2H), 2.64 (m, 1H), 3.02 (m, 1H), 4.10–4.30 (m, 4H), 4.95 (q, 1H), 6.63 (d, 1H), 7.35 (d, 1H), 8.61 (s, 1H).

Step E:
9-Bromo-4-chloro-7-(2',3'-bis(acetoxymethyl)cyclobutyl)-7H-pyrrolo[2.3-d]pyrimidine 4-Chloro-7-(2',3'-bis(acetoxymethyl)cyclobutyl)-7H-pyrrolo[2,3-d]pyrimidine (0.77 g, 2.19 mmol) from Step D was dissolved in 20 mL of methylene chloride and 0.303 g (2.19 mmol) of N-bromoacetamide (commercially available from Sigma Chemical Company) was added. The resultant solution was stirred for 2.5 h and then diluted with methylene chloride, washed with aqueous sodium thiosulfate solution and saturated aqueous sodium bicarbonate solution, dried over anhydrous magnesium sulfate, filtered and concentrated under reduced pressure. The residue was purified on a 2×31 cm silica gel column eluted with 40% ethyl acetate in hexane to give 0.78 g (83% yield) of the title compound; MS DCI-NH$_3$ M/Z: 430 (M+H)+; $^1$H NMR (CDCl$_3$) δ2.00 (s, 3H), 2.13 (s, 3H), 2.30–2.45 (m, 2H), 2.65 (m, 1H), 2.97 (m, 1H), 4.15–4.30 (m, 4H), 4.96 (q, 1H), 7.41 (s, 1H), 8. 61 (s, 1H).

Step F:
4-Amino-9-bromo-7-(2',3'-bis(hydroxymethyl)cyclobutyl)-7H-pyrrolo[2,3-d]pyrimidine 9-Bromo-4-chloro-7-(2',3'-bis(acetoxymethyl)cyclobutyl)-7H-pyrrolo[2,3-d]pyrimidine (0.78 g, 1.82 mmol) from Step E was treated with a solution of 10 mL of ammonia in 20 mL of methanol for 6 h at 120° C in a sealed tube. The solvent was then evaporated and the residue crystallized from methanol to give 424 mg (71% yield) of the title compound; m.p. 185°–187° C.; MS DCI-NH$_3$ M/Z: 327 (M+H)+; (d6-DMSO) δ2.05 (m, 2H), 2.40 (m, 1H), 2.65 (m, 1H), 3.40–3.52 (m, 4H), 4.61 (t, 1H —OH), 4.67 (t, 1H —OH), 4.80 (q, 1H), 6.72 (bs, 2H —NH$_2$), 7.60 (s, 1H), 8.09 (s, 1H).

EXAMPLE 68

9-(2',3'-Bis(hydroxymethyl)cyclobutyl)guanine

Step A: Dimethyl 3-(phenylthio)cyclobutane-1,2-dicarboxylate

To a solution of 1.06 g (7.34 mmol) of dimethyl fumarate in 20 mL of dry 1,2-dichloroethane under nitrogen atmosphere, was added with stirring, 7.34 mmol of a 1.0 M solution of ethylaluminum dichloride in hexane. The resultant yellow solution was heated to reflux and a solution of 1.0 g (7.34 mmol) of phenyl vinyl sulfide in 4 mL of dry 1,2-dichloroethane was added dropwise, via syringe, over a period of 20 minutes. The reaction mixture was allowed to stir at reflux for 3 h. After cooling to ambient temperature, the reaction was quenched carefully with 100 mL of 1.0 N hydrochloric acid solution and the reaction mixture was extracted with 3×50 mL of ethyl acetate. The organic extract was washed with 2×50 mL of water and 50 mL of brine, dried over anhydrous magnesium sulfate, filtered and concentrated to a viscous orange oil. The oil (1.56 g) was chromatographed on silica gel (25 g) eluted with 300 mL of 3% ethyl acetate in 1,2-dichloroethane. The resultant yellow oil was purified by bulb-to-bulb distillation to give the title compound as a yellow oil; b.p 120° C. (0.05 mm Hg); EI-MS, m/e (relative intensity): 280 (M+, 18), 136 (100), 91 (13); $^1$H NMR (CDCl$_3$) δ2.20 (q, 1H), 2.61 (m, 1H), 3.22 (q, 1H), 3.34 (t, 1H), 3.66 (s, 3H), 3.67 (s, 3H), 3.87 (m, 1H), 7.30 (m, 5H).

Step B: 2,3-Dicarbomethoxycyclobutyl phenyl sulfone

To a vigorously stirred solution of 1.05 g (3.75 mmol) of dimethyl 3-(phenylthio)cyclobutane-1,2-dicarboxylate from Step A in 20 mL of methanol, was added slowly a suspension of 3.46 g (11.25 mmol) of OXONE (a commercially available mixture of sulfuric acid potassium salt and potassium hydrogen peroxymonosulfate) in 20 mL of water. The resultant cloudy suspension was stirred for 0.5 h then diluted with 50 mL of water and 100 mL of 1,2dichloroethane. The phases were allowed to separate and the aqueous phase was extracted with 20 mL of 1,2-dichloroethane. The combined organic layers were washed with 2×50 mL of dilute aqueous sodium bicarbonate solution, 2×50 mL of water and 50 mL of brine, dried over anhydrous magnesium sulfate and concentrated to give 1.10 g (94% yield) of the title compound as a viscous oil; EI-MS, m/e (relative intensity): 281 (M+—OCH₃, 9), 171 (100), 139 (24), 111 (47); ¹H NMR (CDCl₃) δ2.48 (m, 1H), 2.76 (m, 1H), 3.23 (q, 1H), 3.52 (s, 3H), 3.74 (s, 3H), 3.80 (m, 1H), 3.92 (q, 1H), 7.58 (m, 2H), 7.68 (m, 1H), 7.89 (m, 2H).

Step C:
3-(2'-Amino-6'-chloro-9'H-purin-9'-yl)-1,2-bis(carbomethoxy)cyclobutane

2-Amino-6-chloropurine (905 mg, 1.0 equiv) was dissolved in 40 mL of anhydrous N,N-dimethylformamide (DMF) with heating. To the resultant solution at ambient temperature under nitrogen atmosphere, was added a solution of 1.83 g (5.87 mmol) of 2,3-dicarbomethoxycyclobutyl phenyl sulfone from Step B in 40 mL of dry DMF. To this soluion was added 1.76 mL (2.0 equiv) of 1,8-diazabicycloundec-7-ene (DBU) and the resulting mixture was stirred for 18 h at 70° C. The reaction mixture was diluted with 250 mL of ethyl acetate, washed with 3×75 mL of saturated aqueous ammonium chloride solution, 3×75 mL of water and 75 mL of brine, dried over anhydrous sodium sulfate, filtered and concentrated in vacuo to give 1.72 g (86% yield) of the title compound; MS DCI-NH₃ M/Z (relative intensity): 342 (M+, 31), 340 (M+, 100); ¹H NMR (CDCl₃) δminor isomer: 2.5–3.6 (m, 3H), 3.69 (s, 3H), 3.78 (s, 3H), 4.46 (t, 1H), 4.94 (q, 1H), 7.80 (s, 1H); major isomer: 2.5–3.6 (m, 3H), 3.12 (s, 3H), 3.80 (s, 3H), 4.18 (t, 1H), 5.38 (q, 1H), 7.88 (s, 1H). This compound was taken on to the next step without purification.

Step D:
3-(2'-Amino-6'-methoxy-9'H-purin-9'-yl)-1,2-bis(carbomethoxy)cyclobutane Sodium methoxide (125 mL of a 0.65 M solution in anhydrous methanol) was added via syringe, under strictly anhydrous conditions, to 1.32 g (3.884 mmol) of 3-(2'-amino-6'-chloro-9'H-purin-9'-yl)-1,2-bis(carbomethoxy)cyclobutane, from Step C, contained under nitrogen atmosphere in a vacuum dried flask equipped with a magnetic stirrer and rubber septum. The resultant a slurry homogenized slowly over the 16 h reaction time. After 16 h of stirring at ambient temperature, the solution was treated with 25 mL of a 8.30 M solution of anhydrous hydrogen chloride in methanol, affording a white precipitate of sodium chloride. This mixture was stirred at ambient temperature for 2 h and then the reaction was quenched by pouring the mixture into 150 mL of saturated aqueous sodium bicarbonate solution. The methanol was removed on the rotory evaporator to give an oily aqueous mixture which was extracted with 3×100 mL of ethyl acetate. The combined organic layers were washed with 50 mL of brine, dried over anhydrous magnesium sulfate, filtered and concentrated to give 1.21 g (93% yield) of the title compound as a tan oil that slowly crystallized; m.p. 143° C.; ¹H NMR (CDCl₃) δ2.73–2.83 (m, 1H), 2.90–3.00 (m, 1H), 3.18–3.25 (m, 1H), 3.71 (s, 3H), 3.79 (s, 3H), 4.07 (s, 3H), 4.11–4.19 (m, 1H), 4.84 (bs, 2H), 4.87–4.96 (m, 1H), 7.70 (s, 1H). The product was taken on to the next step without purification.

Step E:
3-(2'-Amino-6'-methoxy-9'H-purin-9'-yl)-1,2-bis(hydroxymethyl)cyclobutane 3-(2'-Amino-6'-methoxy-9'H-purin-9'-yl)-1,2-bis(carbomethoxy)cyclobutane (0.9 g, 2.68 mmol) from Step D was dissolved in 50 mL of anhydrous THF under a nitrogen atmosphere. To this stirred solution at ambient temperature was added lithium aluminum hydride (8.5 mL of a 1.0 M solution in THF, 8.05 mmol) affording a white precipitate. This mixture was stirred at ambient temperature for 1.0 h and then the reaction was quenched by the successive dropwise addition of 0.3 mL of water, 0.3 mL of 15% aqueous sodium hydroxide solution and 0.9 mL of water. The mixture was filtered and the filter cake was washed with 50 mL of THF. The combined organic filtrates were dried over anhydrous magnesium sulfate, filtered and concentrated to give 0.735 g (99% yield) of the title compound as a slightly yellowish colored oil. ¹H NMR CD₃OD) δ2.13–2.25 (m, 1H), 2.29–2.39 (m, 1H), 2.48–2.60 (m, 1H), 2.73–2.86 (m, 1H), 3.66–3.72 (m, 4H), 4.04 (s, 3H), 4.51–4.61 (m, 1H), 4.88 (s, exchangable protons), 7.96 (s, 1H). The product was taken on to the next step without purification.

Step F: 9-(2',3'-Bis(hydroxymethyl)cyclobutyl)guanine 3-(2'-Amino-6'-methoxy-9'H-purin-9'-yl)-1,2-bis(hydroxymethyl)cyclobutane (0.711 g, 2.55 mmol) from Step E was dissolved in 50 mL of 1 N aqueous hydrochloric acid solution and the resultant solution was heated at reflux for 16 h, cooled to ambient temperature and concentrated under reduced pressure. The residue was re-dissolved in a small quantity of water and the pH of this solution was adjusted to 5.5 with 15% aqueous sodium hydroxide solution, affording a white precipitate. This material was recrystallized from 5 mL of water to give 473 mg (70% yield) of the title compound as a white powder; the ¹H NMR spectrum of the product was identical to a ¹H NMR spectrum of the product of Example 1.

EXAMPLE 69

9-(2',3'-Bis(hydroxymethyl)cyclobutyl)adenine

Step A:
3-(6'-Amino-9'H-purin-9'-yl)-1,2-bis(carbomethoxy)cyclobutane

To a mixture of 2,3-dicarbomethoxycyclobutyl phenyl sulfone (1.74 g, 5.58 mmol), the product of Step B of Example 68, and 0.753 g (5.58 mmol) of adenine, was added 70 mL of anhydrous DMF. To the resulting suspension was added 1.67 mL (2.0 equiv) of DBU and the resultant reaction mixture was stirred for 9 h at 75° C. The reaction mixture was then diluted with 250 mL of ethyl acetate, washed with 3×75 mL of half-saturated aqueous ammonium chloride, 2×75 mL of water and 75 mL of brine. The organic phase was dried over anhydrous sodium sulfate, filtered and concentrated in vacuo to give 0.651 g (38% yield) of the title compound. MS DCI-NH3 M/Z: 306 (M+H)+; ¹H NMR (CDCl₃) δminor isomer: 2.5–3.6 (m, 3H), 3.69 (s, 3H), 3.78 (s, 3H), 4.59 (t, 1H), 5.44 (q, 1H), 7.81 (s, 1H), 8.34 (s, 1H); major isomer: 2.5–3.6 (m, 3H), 3.72 (s, 3H), 3.80 (s, 3H), 4.17 (t, 1H), 5.07 (q, 1H), 7.93 (s, 1H), 8.37 (s, 1H). The product can be taken on to the next step without purification.

Step B: 9-(2',3'-Bis(hydroxymethyl)cyclobutyl)adenine 3-(6'-Amino-9'H-purin-9'-yl)-1,2bis(carbomethoxy)-cyclobutane (1.0 g, 3.28 mmol) from Step A is dissolved in 50 mL of anhydrous THF under a nitrogen atmosphere. To this stirred solution, at ambient temperature, is added lithium aluminum hydride to afford a white precipitate. This mixture is stirred at ambient temperature for 1 h and then the reaction is quenched by the successive dropwise addition of 0.3 mL of water, 0.3 mL of 15% aqueous sodium hydroxide solution and 0.9 mL of water. The mixture is filtered and the filter cake is washed with 50 mL of THF. The combined organic filtrates are dried over anhydrous sodium sulfate, filtered and concentrated to give the title compound.

EXAMPLE 70

3-(2'-Amino-6'-chloro-9'H-purin-9'-yl)-1,2-bis(carbomethoxy)cyclobutane

Step A: Dimethyl 3-bromocyclobutane-1,2-dicarboxylate

A solution of 5 g (51 mmol) of maleic anhydride and 0.5 mL (4 mmol) of acetophenone in 50 mL of ethyl acetate was added to a 100 mL pyrex photochemical reaction vessel. The vessel was sealed and purged with nitrogen for 10 min then cooled with tap water while 13.8 g (129 mmol) of vinyl bromide was being added to the ethyl acetate solution. The vessel was then irradiated for 20 h with a 450 Watt medium pressure mercury vapor lamp. The solution was concentrated in vacuo and the residue dissolved in 200 mL of methanol which had been treated with 1 mL of trimethylsilyl chloride. The solution was stirred at ambient temperature overnight and then concentrated to a brown viscous oil. The oil was chromatographed on silica gel (200 g) eluted with 20% ethyl acetate in hexane to give a yellow oil. The oil was purified by short-path distillation using a 1" fractionating column to give 2.5 g (19.5% yield) of the title compound; b.p. 75°–80° C. (0.1 mm Hg); EI-MS, m/e (rel intensity): 220 (M+—$CH_3O$, 60), 218 (60), 192 (42), 190 (39), 171 (100); $^1H$ NMR ($CDCl_3$) δ2.60 (m, 1H), 2.82 (m, 1H), 3.56 (td, 1H), 3.72 (m, 6H), 3.94 (t, 0.4H), 4.12 (q, 0.6H), 4.93 (q, 1H).

Step B: 3-(2'-Amino-6'-chloro-9'H-purin-9'-yl)-1,2-bis(carbomethoxy)cyclobutane

2-Amino-6-chloropurine (3.3 g, 19.5 mmol) was dissolved, with heating, in 100 mL of DMF under nitrogen atmosphere and the resultant solution was cooled to ambient temperature. Dimethyl 3-bromocyclobutane-1,2-dicarboxylate (4.44 g, 17.7 mmol) from Step A was added via syringe, followed by 2.91 mL (19.5 mmol) of DBU and the reaction mixture was stirred overnight at ambient temperature. The reaction was quenched in 100 mL of saturated aqueous ammonium chloride solution and the resultant aqueous solution was extracted with 3×100 mL of ethyl acetate. The combined ethyl acetate solution was washed with 3×50 mL of water and 50 mL of brine, dried over anhydrous magnesium sulfate, filtered and concentrated to a solid residue. The residue was purified on silica gel (250 g) eluted with 2% methanol in chloroform to give 2.65 g (44% yield) of the title compound and 0.64 g (11% yield) of the N-7 isomer. The $^1H$ NMR spectrum was identical to the $^1H$ NMR spectrum of the product of Step C of Example 68.

EXAMPLE 71

Dimethyl 3-phenylthiocyclobutane-1,2-dicarboxylate

To a solution of dimethyl maleate (0.50 mL, 4 mmol) and phenyl vinyl sulfide (0.52 mL, 4 mmol) in 17 mL of 1,2-dichloroethane under nitrogen atmosphere, was added 1 equivalent (4 mL of a 1 M solution in hexane) of ethylaluminum dichloride. The resultant solution was heated at 85° C. for 18 h and then diluted with 75 mL of methylene chloride. The methylene chloride solution was washed three times with saturated aqueous ammonium chloride and once with brine, dried over anhydrous sodium sulfate, filtered and concentrated to give 0.98 g of the title compound; EI-MS, m/e (rel intensity): 280 (M+, 14), 136 (100).

EXAMPLE 72

2,4-dioxo-6-phenylthio-3-oxabicyclo[3.2.0]heptane

To a solution of maleic anhydride (0.39 g, 4 mmol) and phenyl vinyl sulfide (0.52, 4 mmol) in 17 mL of 1,2-dichloroethane under nitrogen, was added 2 mL (0.5 equiv) of ethylaluminum dichloride. The resultant solution was stirred at ambient temperature for 0.5 h and then diluted with 75 mL of methylene chloride. The methylene chloride solution was washed three times with saturated aqueous ammonium chloride solution and once with brine, dried over anhydrous sodium sulfate and concentrated to give 0.85 g of the title compound; EI-MS, m/e (rel intensity): 234 (M+, 23), 136 (100), 109 (12), 91 (21).

The antiviral activity of the compounds of the invention can be determined by the following methods.

A-1. Evaluation of Compounds for Activity Against Herpes Simplex Virus Types 1 and Types 2

The challenge viruses were propagated and assayed in cells that were pregrown as monolayer cultures in plastic tissue culture flasks and 96-well plates, using cell culture media appropriate for the host cell cultures. The following viruses and host cell cultures were employed:

| Challenge Virus | Host Cell Type |
| --- | --- |
| Herpes simplex type 1 (HSV-1) strain E-377 | Continuous passage African green monkey kidney (Vero) |
| Herpes simplex type 2 (HSV-2) strain MS | Continuous passage African green monkey kidney (Vero) |
| Herpes simplex type 1 HSV-1 strain (BW10168) TK- | Continuous passage African green monkey kidney (Vero) |
| Herpes simplex type 2 HSV-2 strain (BW9787) TK- | Continuous-passage African green monkey kidney (Vero) |

On the day of use, a weighed sample of each compound to be evaluated was dissolved and diluted in serial $10^{0.5}$ dilutions in the culture medium appropriate for each virus host cell system.

CPE Inhibition Assay Procedure

Mammalian cells were pregrown as monolayers in wells of COSTAR 96-well tissue culture plates using suitable cell culture media. Stock viruses were pretitered according to the method of Reed and Muench (Amer. J. Hyg. 27:493–497, 1938) and diluted in cell culture medium to yield 32 $CCID_{50}$ (cell culture infectious dose, 50%) units per 0.1 ml. Antiviral assays were designed to test seven concentrations of each compound, from cytotoxic to noncytotoxic levels, in triplicate against each of the challenge viruses in microtiter plate wells containing suitable cell monolayers. To each of the replicate cell cultures were added 0.1 ml of the test drug solution and 0.1 ml of virus suspension. Cell controls containing medium alone, virus controls containing medium and virus, and drug cytotoxicity controls containing medium and each drug concentration were run simultaneously with the test samples assayed in each experiment. The covered plates were incubated at 37° C. in a humidified atmosphere containing 5%

$CO_2$ until maximum CPE (cytopathogenic effect) was observed in the untreated virus control cultures. The cell monolayers were examined microscopically for virus induced CPE and for drug cytotoxicity.

Antiviral activity was determined by calculating the degree of inhibition of virus induced CPE in drug treated, virus-infected cell cultures by means of a virus rating (VR). The VR is a standard weighted measurement of antiviral activity taking into account both the degree of CPE inhibition and drug cytotoxicity, and is determined by a modification of the method of Ehrlich et al. (Ann. N.Y. Acad. Sci. 130: 5–16, 1965) as described below. CPE was graded for each individual culture in each microtiter plate well according to the following scale:

4 = 100% of the cells affected by virus;
3 = 75% of the cells affected by virus;
2 = 50% of the cells affected by virus;
0 = No CPE; normal cell monolayer;

The VR was calculated as 0.1 of the sum of the numerical differences between the recorded CPE grade of each test well and that of the corresponding virus control in the culture plate. Numerical differences between the scores of test wells containing a drug concentration which was partially cytotoxic (p) and their corresponding virus controls were halved.

The minimum inhibitory drug concentration which reduced the cytopathogenic effect (CPE) by 50% ($MIC_{50}$) was calculated by using a regression analysis program for semilog curve fitting. A therapeutic index (TI) for each active compound for each susceptible virus was determined by dividing the minimum cytotoxic concentration of the test compound by the $MIC_{50}$. Test results are provided in Tables 1A and 1B.

A-2. Alternate Method for Evaluation of Compounds for Activity Against Herpes Simplex Virus Types 1 and 2

Confluent Vero cell monolayers were infected with a dilution of stock virus which yielded approximately 100 plaque forming units (pfu) per well. After the adsorption period, the infected cell monolayers were treated in duplicate with serial dilutions of the test compound. Duplicate cell controls containing medium alone and virus controls containing medium and virus were run simultaneously with the test compound. After incubation for 3 to 4 days to allow for the development of visible, discrete plaques in the untreated, virus infected control cultures, the monolayers were fixed with formaldehyde and stained with crystal violet. Plaques visible to the unaided eye were counted and the mean number of plaques in the duplicate wells for each compound concentration tested and for the untreated, virus infected controls were determined. The concentration of test compound which reduced by 50% the mean number of plaques in the untreated, virus infected control cultures was then determined and expressed as the $ID_{50}$. Test results are provided in Table 1C.

B. Evaluation of Compounds for Activity Against Human Immunodeficiency Virus Cell Lines and Virus The ATH8 human T-cell line expresses high levels of the CD4 surface antigen and is quite sensitive to the cytopathogenic effect (CPE) of HIV. The cells were propagated in RPMI 1640 medium supplemented with 4 mM glutamine, 15% heat-inactivated fetal bovine serum (Biocell), antibiotics (50 units of penicillin and 50 pg of streptomycin per ml), and 50 units of recombinant-derived human interleukin-2 (ala-125; AMGen Biologicals) per ml.

The clone H9 cell line is another CD4+ human T-cell line which is permissive for HIV replication but largely resistant to virus induced CPE. H9 cells productively infected with the HTLV-IIIB strain of HIV served as the source of infectious virus. These cells were propagated in RPMI 1640 medium supplemented with glutamine and antibiotics as described above, and with 20% heat-inactivated fetal bovine serum. Freshly harvested, undiluted culture supernatant from the H9/HTLV-IIIB producer cells was used for infectious virus inoculum. Culture supernatant collected 48 hours post cell passage showed the best infectivity.

CPE Inhibition Assay

The screening of compounds for antiviral activity was performed using a modification of the CPE-inhibition assay originally developed by Broder and co-workers. This assay is based on the ability of uninfected ATH8 cells to grow and form a pellet at the bottom of a culture tube. Starting about 4 days after HIV addition, infected ATH8 cells begin to die and the pellet starts to break up. By day 10 a clear differential is observable in the size of the cell pellet in uninfected control wells versus infected control wells. The protective effect of test compounds can be assessed by adding them at varying concentrations to the cultured cells at the time of virus infection, then monitoring the status of the cell pellet.

ATH8 cells were used as the primary target in the HIV induced CPE inhibition assay. Cells were treated with polybrene (2 ug/ml in growth medium) for 30 minutes at 37° C., then collected by gentle centrifugation (40×g for 15 minutes at room temperature) and resuspended in clarified (8000×g for 15 minutes at 4° C.) supernate freshly harvested from 48 hours post-passage $H9/HTL-III_B$ cells. Following a 60 minute adsorption period at 37° C., the cells were dispensed into the U-bottom wells of 96-well trays ($1 \times 10^4$ cells in 0.1 ml per well). An equal volume (0.1 ml) of supplemented RPMI 1640 medium containing test compound and twice the normal concentration of interleukin-2 was then added to each well. Test compounds were evaluated at seven half-log dilutions ranging from 100 ug/ml to 0.1 ug/ml Triplicate virus infected cultures and one uninfected compound cytotoxicity control culture were included at each concentration. Cultures were incubated at 37° C. in a humidified atmosphere of 5% CO2 in air.

Between 7 and 10 days post infection, all wells were visually monitored for the degree of CPE-inhibition as reflected by cell pellet size, and aliquots were taken from selected wells for determination of cell number and viability (based on trypan-blue dye exclusion). Test results are provided in Table 2.

C-1. Alternate Method for Evaluation of Compounds for Activity Against Human Immunodeficiency Virus The method of Mitsuya and Broder (AIDS: Modern Concepts and Therapeutic Challenges; Broder, S. ED.; Marcel Dekker, Inc.; New York, 1987; Chapter 18) was used to determine the in vitro anti-HIV-1 and anti HIV-2 activity in ATH8 cells of some compounds of the invention. The results of the test are expressed as the percentage of ATH8 cells that were protected from the cytopathogenic effects of HIV at various concentrations of the compound of the invention. Test results are provided in Tables 3A and 3B.

C-2. Alternate Method for In Vitro Evaluation of Compounds for Anti-HIV-½ Activity Uninfected H9 cells at $4 \times 10^5$ viable cells/ml were infected with approximately 100 viral infectious units (ifu) for 2 hrs at 37° C. The viral infectious dose (ifu) was determined by the tissue culture infectious dose ($TCID_{50}$) method for each stock of HIV-1 (HTLV-IIIB) and HIV-2. Cells were washed three times to remove residual virus, then resuspended in RPMI-1640 growth medium containinmq test compound at various concentrations, then transferred to 24 well tissue culture plates and grown at 5% $CO_2$ at 37° C. Infected cells in media containing no drug were run simultaneously as a control. Aliquots of culture supernatants were removed at 4, 6 and 10 days and monitored for HIV antigen levels by the Abbott HIV-1 antigen enzyme immunoassy (HIVAG-1). Cell viability was also determined at these time points and cells were refed with media containing test compound (except for control wells). Anti-HIV acitivity is reported as the concentration of compound causing a 50% inhibition ($IC_{50}$) in HIV antigen levels versus infected cells without test compound. Test results are provided in Table 3C.

C-3. Method for Evaluation of the Activity of Compounds Against HIV in PBMC's

Cells

Human peripheral blood mononuclear cells (PBMC) from healthy HIV-1 seronegative and hepatitis B virus seronegative donors were isolated by Ficoll-Hypaque discontinuous gradient centrifugation at $1,000 \times g$ for 30 minutes, wahed twice in phosphate buffered saline (pH 7.2; PBS), and pelleted at $300 \times g$ for 10 minutes. Before infection, the cells were stimulated by phytohemagglutinin (PHA) at a concentration of 16.7 ug/ml for three days in RPMI 1640 medium supplemented with 15% heat-inactivated fetal calf serum, 1.5 mM L-glutamine, penicillin (100 U/ml), streptomycin (100 ug/ml) and 4 mM sodium bicarbonate buffer.

Inhibition of Virus Replication in Human PBMC

Uninfected PHA-stimulated human PBMC were uniformly distributed among 25 $cm^2$ flasks to give a 5 ml suspension containing about $2 \times 10^6$ cells/ml. Suitable dilutions of virus were added to infect the cultures. The mean reverse transcriptase (RT) activity of the inocula was 60,000 dpm RT activity/$10^6$ cells. The test compounds at twice their final concentrations in 5 ml of RPMI 1640 medium, supplemented as described above, were added to the cultures. Uninfected and untreated PBMC at equivalent cell densities were grown in parallel as controls. The cultures were maintained in a humidified 5% $CO_2$-95% air incubator at 37° C. for six days after infection at which point all cultures were sampled for supernatant RT activity.

RT Activity Assay

Six milliliter supernatant from each culture was clarified from cells at $300 \times g$ for 10 minutes. Virus particles were pelleted from 5 ml samples at 40,000 rpm for 30 minutes using a Beckman 70.1 Ti rotor and suspended in 200 ul of virus disrupting buffer (50 mM Tris HCl, pH 7.8, 800 mM NaCl, 20% glycerol, 0.5 mM phenylmethyl sulfonyl fluoride and 0.5% Triton X-100).

The RT assay was perfromed in 96-well microtiter plates as described by Spira, et al. (J. Clin. Microbiol. 25 97 (1987)). The reaction mixture, which contained 50 mM Tris-HCl pH 7.8, 9 mM $MgCl_2$, 5 mM dithiotreitol, 4.7 ug/ml $(rA)_n \cdot (dT)_{12-18}$, 140 uM DATP, and 0.22 uM [$^3$H]TTP (specific activity 78.0 Ci/mmol, equivalent to 17,300 cpm/pmol); NEN Research Products, Boston, Mass.) was added to each well. The sample (20 ul) was added to the reaction mixture which was then incubated at 37° C. for 2 hours. The reaction was terminated by the adition of 100 ul 10% trichloroacetic acid (TCA) containing 0.45 mM sodium pyrophosphate. The acid insoluble nucleic acids which precipitated were collected onglass filters using a Skatron semi automatic harvester (setting 9). The filters were washed with 5% TCA and 70% ethanol, dried and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (model 2,000CA). The results were expressed in dpm/ml of original clarified supernatant. The procedures for the anti-HIV-1 assays in PBMC described above have been published (Antimicrob. Agents Chemother. 32 1784 (1988)).

Median-effect Method $EC_{50}$ values were obtained by analysis of the data using the median-effect equation (Chou, et al., Adv. Enz. Regul. 22 27 (1984)). The results of this test are provided in Table 3D.

Cytotoxicity

The test compounds were evaluated for their potential toxic effects on uninfected PHA-stimulated human PBM cells. The cells were cultured with and without test compound for 6 days at which time aliquots were counted for cell viability.

D. Evaluation of Compounds for Activity Against Human Cytomegalovirus (HCMV)—Virus Yield Reduction Assay Human diploid embryonic lung (MRC5) cells were grown in 35 mm wells of 6-well tissue culture plates. Subconfluent cell monolayers were rinsed with phosphate-buffered saline (PBS) and were exposed to 0.5 ml/well of HCMV (strain AD169) suspension for 1.5 hours at 37° C. The virus suspension was diluted in MEM +2% fetal bovine serum (FBS) to yield a multipicity of infection (MOI) of approximately 0.1 plaque forming units (PFU)/cell. Following the virus adsorption period, the inocula were removed and infected cell layers were rinsed with PBS. Aliquots (2.0 ml) of each test drug concentration (dissolved in MEM supplemented with 2% FBS) were dispensed into triplicate cell cultures: two virus-infected cultures and one uninfected cytotoxicity control culture (exposed to medium without virus for 1.5 hours). Untreated virus-infected control cultutres and untreated, uninfected cell control cutures were fed with medium alone. The culture plates were incubated at 37° C. in a humidified atmosphere of 2% $CO_2$ in air.

All cell culture fluids were replaced with fresh drug and medium 48 hours postinfection (p.i.).

On Day 6 p.i., the cell layers were examined microscopically for cytopathogenic effect (CPE) and drug cytotoxicity. The test and virus control cultures were then harvested by subjecting the cell layers to one cycle of freeze-thawing. The cellular material was scraped into the ambient medium and the contents from replicate cultures were pooled, dispensed into cryotubes and stored at −135° C.

Drug cytotoxicity was determined quantitatively by a method based on the reduction of the tetrazolium salt, 3-(4,5-dimethyl-thiazol-2-yl)-2,5-diphenyl tetrazolium bromide (MTT) by mitochondrial enzymes of viable host cells to MTT formazan (T. Mosmann, 1983). Drug cytotoxicity controls and cell controls were treated with MTT (dissolved in culture medium) followed by 20% SDS (in 0.02 N HCl) to dissove the crystals of MTT formazan. The blue color of the MTT formazan was measured spectrophotometrically at 570 nm. Drug cytotoxicity was determined by comparing the absorbance (O.D.) of each drug cytotoxicity control with the mean O.D. of the cell control cultures and expressed as percent of control.

The harvested test and virus control samples were thawed and the infectious virus yield was determined by plaque assay in MRC5 cells grown in 12-well cluster plates. Inhibiton of HCMV replication by each test compound was determined by comparing the progeny virus yields in the drug-treated cultures with the progeny virus yield in the untreated, virus-infected control cultures. Test results are provided in Table 4.

E. Evaluation of Compounds for In Vivo Activity Against Herpesvirus 1 in Mice Four-week-old female outbred Swiss mice (CD-1, VAF+, Charles River Labs) were housed 5 per Microisolator ® cage. Feed and water were supplied ad libitum. Fifteen mice were randomly assigned to each of the following treatment groups:

1. untreated controls
2. diluent (0.4% CMC/PBS controls)
3. 100 mg/kg test compound
4. 32 mg/kg test compound
5. 10 mg/kg test compound
6. 3.2 mg/kg test compound Test compounds were diluted in 0.4% caboxymethylcellulose (CMC) prepared in phosphate buffered saline (PBS) at aconcentrations consistent with dosing at 0.1 ml per 10 g of body weight. Compounds were administered subcutaneously once daily for a total of 7 doses. Five mice in each treatment group served as uninfected toxicity controls. The remaining ten mice in each group were challenged intraperitoneally with an $LD_{90}$ dose of the twelfth in vivo passage of Herpesvirus 1 (strain 123). Virus challenge was administered two hours after the first dose of compound was given. Mortality was monitored daily for 21 days. The mortality rates, average day of death, geometric mean time to death and virus rating were calculated for each treatment group. The results of this test are presented in Table 5.

F. Evaluation of Compounds for Efficacy Against Hepatitis B Virus In Vivo in Ducklings The test method is an adaptation of the method of Smee, et al., Antimicrob. Agents Chemotherap. 27 277 (1985). The serum level of duck hepatitis B virus (DHBV) DNA was monitored in 6 infected Pekino ducklings from age 6 days to age 27 days. Four ducklings were treated with 70 mg/kg/day IP, b.i.d. of the test compound as a 3 mg/ml solution in 0.9% aqueous NaCl on days 10–17. Two control ducklings were treated with 23 ml/kg/day IP, b.i.d. of 0.9% aqueous NaCl on days 10–17. The level of DHBV DNA in the duckling serum was measured daily. The results of this test are presented in Table 6.

G. Evaluation of Compounds for Activity Against Epstein-Barr Virus (EBV) In Vitro Virus producing cells (P3HR-1) were exposed to test compound for 14 days and EBV genome copies per cell were determined by EBV-specific cRNA-DNA hybridization (Lin, et al., J. Virology 50 50–55 (1984). The results of this test are presented in Table 7.

H. Evaluation of Compounds for Selective Inhibition of Varicella-Zoster Virus Plaque Formation in Cell Culture For the plaque reduction assay, secondary human foreskin fibroblasts were seeded in wells of 12-well tissue culture plates and incubated at 37° C. in a humidified atmosphere containing 2% $CO_2$ in air. Subconfluent HFF were rinsed with MEM and exposed to 0.25 ml/well of a suspension of VSV (a clinical isolate designated DM625 obtained from Dr. Richard Whitley of the University of Alabama Hospitals, Birmingham, Ala.) diluted in MEM+2% FBS for 2 hours at 37° C. Following the virus adsorption period, the inocula were removed and infected cell layers were rinsed with MEM. Triplicate VZV infected cell culture wells were treated with 1.0 ml of each test compound concentration (in MEM +2% FBS). Six untreated virus infected cell cultures and triplicate untreated uninfected cell cultures were fed with 1.0 ml of MEM+2% FBS to serve as controls. Wells containing uninfected HFF were treated with each test compound concentration to monitor the cytotoxicity of the test compounds. The 12-well plates were incubated at 37° C. in the $CO_2$ incubator. At 48 hours postvirus infection (p.i.) fluids were replcaed with fresh test compound and/or culture medium.

Five days p.i. the VZV plaques were counted (unstained, using low magnification). The effect of each test compound concentration on plaque formation was determined by comparing the mean number of plaques in the replicate drug-treated cultures with the mean plaque counts of the untreated virus control cultures.

The test compound cytotoxicity control cutures were examined microscopically for gross morphologic changes, then treated with MTT and 20% SDS. The blue color of the MTT formazan was measured spectrophotometrically at 570 nm. Drug cytotoxicity was determined by comparing the absorbance (O.D.) of each test compound cytotoxicity control with the mean O.D. of the cell control cultures and expressed as percent of control. Test results are provided in Table 8.

I. Evaluation of Compounds for Cytotoxic Activity Against Cultured Tumor Cells Test compunds were dissolved in DMSO, ethanol, water or other suitable solvent. This stock solution was diluted in culture medium to twice the highest concentration to be tested. From this 2×stock, two-fold serial dilutions were prepared in 96-well microtiter trays, each well containing twice the desired final concentration. Each concentration was tested in triplicate and compared to triplicate drug-free controls.

Cells were grown and tested in RPMI 1640 supplemented with 10% fetal calf serum. After harvesting, viable cell counts were determined by hemacytometer or coulter counter and cell density was adjusted to 25,000 per milliliter. One tent milliliter of inoculum was added to each well for a final concentration of 2,500 cells per well. Addition of the inoculum dilutes the test compunds to the desired final concentration.

Microtiter trays were incubated for three days at 37° C. in a humidified atmosphere containing 5% $CO_2$.

After three days, 20 ul of 5 mg/ml MTT in phosphate buffered saline (pH 7.2) was added to each well. Trays were returned to the incubator for ninety minutes to allow the surviving cells to reduce the dye. Medium and unreduced dye were removed by aspiration or inversion. DMSO was added to each well to dissolve the water insoluble, colored end-product of the dye reducton. Absorbance was measured spectrophotometrically at 570 nm. This method is a modification of the method reported by Mosmann, J. Immunol. Meth., 65 55 (1983). Test results are provided in Table 9.

TABLE 2

Antiviral Activity of Compounds of Formula I Against Human Immunodeficiency Virus (HIV) In ATH8 Cells**

| Compound of Example No. | Protocol | VR | ID50 | MTC | TI |
|---|---|---|---|---|---|
| 4B | CPE Inhibition | 1.1 | — | 10.0 | — |
| 4C | CPE Inhibition | 3.5 | <0.1 | 3.2 | 32 |

**Using method of section B from above

TABLE 3A

Antiviral Activity of Compounds of Formula I Against Human Immunodeficiency Virus (HIV-1) In ATH8 Cells**

| Compound | Concentration (uM) | Protective Effect (%) | Cytotoxicity (%) |
|---|---|---|---|

TABLE 1A

Antiviral Activity of Compounds of Formula I Against Herpes Simplex

| | Herpes Simplex Type 1 (E-377) Vero | | | | Herpes Simplex Type 2 (MS) Vero | | | |
|---|---|---|---|---|---|---|---|---|
| Compound of Example No. | VR[1] | ID50[2] | MTC[3] | TI[4] | VR | ID50 | MTC | TI |
| 1I | 5.7 | 1.5 | 320 | 213 | 4.1 | 6.4 | 320 | 50 |
|  | 5.1 | 2.5 | 320 | 129 | 3.4 | 10.6 | 320 | 30 |
| 1H | 1.5 | 83 | 320 | 3.9 | 0.6 | 179 | 320 | 1.8 |
|  | 1.4 | 89 | 320 | 3.6 | 0.5 | 217 | 320 | 1.5 |
| 3 | 3.6 | 10.07 | 320 | 31.8 | 2.0 | 50.5 | 320 | 6.34 |
| 4C | 2.1 | 8.7 | 32 | 3.7 | 1.8 | 18.1 | 100 | 5.5 |
| 5G | 2.1 | 146 | >320 | >2.2 | 0.9 | — | >320 | >1.0 |
| 6 | 2.4 | 31.7 | 320 | 10.1 | 1.6 | 71.8 | 320 | 4.5 |
| 7 | 0.55 | 270.9 | 320 | 1.2 | | | | |
| 8E | 0.9 | — | | 320 | — | 1.35 | 54.7 | 100 | 1.8 |
| 20 | 2.2 | 12.1 | 100 | 8.2 | 1.9 | 15.7 | 100 | 6.4 |
| 21 | 1.0 | 88 | 320 | 3.6 | 1.2 | 75 | 320 | 4.3 |
| 23 | 1.7 | 100 | >320 | 3.2 | 0.7 | — | >320 | — |
| 67C | 1.2 | 11.1 | 32 | 2.9 | 0.9 | 14.9 | 32 | 2.1 |

TABLE 1B

Antiviral Activity of Compounds of Formula I Against Herpes Simplex

| | Herpes Simplex Type 1 (BW10168) TK- Vero | | | | Herpes Simplex Type 2 (BW9787) TK- Vero | | | |
|---|---|---|---|---|---|---|---|---|
| Compound of Example No. | VR[1] | ID50[2] | MTC[3] | TI[4] | VR | ID50 | MTC | TI |
| 1I | 3.3 | 4.06 | 100 | 24.6 | 5.4 | 0.79 | 100 | 127 |

[1]VR = Virus Rating: A measurement of selective antiviral activity which takes into account the degree of virus- induced cytopathogenic effects (CPE) and the degree of cytotoxicity produced by the test compound, determined by a modification of the method of Ehrlich et al. (Ann. N.Y. Acad. Sci. 130: 5–16, 1965). A VR > 1.0 indicates definite (+) antiviral activity, a VR of 0.5–0.9 indicates marginal to moderate antiviral activity, and a VR < 0.5 usually indi cates no significant antiviral activity.
[2]ID50 = The minimum drug concentration (ug/ml) that inhibited the CPE by 50%, calculated by using a regression analysis program for semilog curve fitting.
[3]MTC = The minimum drug concentration (ug/ml) causing any cytotoxicity.
[4]TI = Therapeutic Index, calculated by dividing the minimum cytotoxic drug concentration by the ID50.
The results indicate that the compounds are active against HSV-1 and HSV-2.

TABLE 1C

Antiviral Activity of Compounds of Formula I Against Herpes Simplex

| Challenge Virus: | HSV-1 (E-377) | HSV-1 (123) | HSV-2 |
|---|---|---|---|
| Host Cell Type: | Vero | Vero | Vero |
| Compound of Example No. | MIC50 (ug/ml) | MIC50 (ug/ml) | MIC50 (ug/ml) |
| 1I | 0.5 | 1.0 | 1.0 |
| 42P | 1.0 | 3.0 | 1.0 |

The results indicate that the compounds are active against HSV-1 and HSV-2.

| | | | |
|---|---|---|---|
| Ex. 1I | 1 | 51 | 0 |
| | 10 | 90 | 0 |
| Ex. 4C | 1 | 48 | 12 |
| | 10 | 63 | 33 |
| | 100 | 76 | 34 |
| Ex. 6 | 1 | 21 | 0 |
| | 10 | 48 | 4 |
| | 100 | 46 | 32 |
| | 500 | 57 | 38 |

**Using method of section C from above

TABLE 3B

Antiviral Activity of Compounds of Formula I Against Human Immunodeficiency Virus (HIV-2) In ATH8 Cells**

| Compound | Concentration (uM) | Protective Effect (%) | Cytotoxicity (%) |
|---|---|---|---|
| Ex. 11 | 1 | 24 | 11 |
|  | 10 | 65 | 11 |
| Ex. 4C | 1 | 33 | 9 |
|  | 10 | 70 | 15 |

**Using method of section C from above

The results indicate that the compounds are active against HIV-2 and/or HIV-1.

TABLE 3C

Antiviral Activity of Compounds of Formula I Against Human Immunodeficiency Virus (HIV-1) in H9 Cells

| Compound | Concentration (uM) | % Inhibition | $IC_{50}$(uM) |
|---|---|---|---|
| Ex. 4C | 10 | 98 | 2.1 |
|  | 5 | 96 |  |
|  | 2.5 | 62 |  |
|  | 0.625 | 0 |  |
| Ex. 11 | 10 | 88 | 1.1 |
|  | 2.5 | 75 |  |
|  | 1.25 | 63 |  |
|  | 0.625 | 19 |  |
|  | 0.312 | 0 |  |

The results indicate that the compounds are active against HIV-1.

TABLE 3D

Antiviral Activity of Compounds of Formula I Against Human Immunodificiency Virus (HIV-1) in PBMC Cells

| Compound | $EC_{50}$(uM) | Cytotoxicity in PBMC $IC_{50}$(uM) |
|---|---|---|
| Ex. 4C | 0.96 | 23 |
| Ex. 11 | 0.98 | 38.8 |

The results indicate that the compounds are active against HIV-1.

TABLE 4

Antiviral Activity of Compounds of Formula I Against Human Cytomegalovirus (HCMV) In MRC5 Cells

| Compound | Drug Conc. (ug/ml) | HCMV yield (log10 PFU/ml) | HCMV yield reduction (log10 PFU/ml) | MTT assay Percent of control |
|---|---|---|---|---|
| Ex. 11 | 1.0 | 3.12 | 1.15 | 100 |
|  | 3.2 | 2.43 | 1.84 | 100 |
|  | 10 | 1.63 | 2.64 | 100 |
|  | 32 | <0.6* | >3.7 | 100 |
| Ex. 4C | 0.32 | 3.3 | 1.4 |  |
|  | 1.0 | 2.6 | 2.1 |  |
|  | 3.2 | <0.6 | >4.1 | 95 |
|  | 10 | <0.6 | >4.1 | 90 |
|  | 32 | <0.6 | >4.1 | 67 |
| Ex. 67B | 3.2 | 4.9 | 0.4 | — |
|  | 10 | 4.0 | 1.3 | 86 |
|  | 32 | 3.1 | 2.2 | 68 |
| Virus control | 0 | 4.27 |  |  |

*below limit of detection

The results indicate that the compound is active against HCMV.

TABLE 5

Antiviral Efficacy of Compounds of Formula I Against Intraperitoneal Challenge with Herpesvirus 1 in Mice

| Compound | Dose mg/kg | No. Dead/ No. Uninfected | No. Dead/ No. Infected | GMTD* | VR** |
|---|---|---|---|---|---|
| untreated |  | 0/5 | 10/10 | 8.8 | NA |
| 0.4% CMC/PBS |  | 0/5 | 10/10 | 8.3 | NA |
| Example 11 | 3.2 | 0/5 | 8/10 | 10.8 | 1.3 |
|  | 10 | 0/5 | 5/10 | 13.0 | 1.6 |
|  | 32 | 0/3 | 0/10 | 21.0 | 2.5 |

*GMTD = geometric mean time to death
**VR (virus rating) = GMTD of experimental/GMTD of diluent-treated control The results indicate that the compounds is active in vivo against Herpesvirus 1.

TABLE 6

Antiviral Efficacy of Compounds of Formula I Against Hepatitis B Virus in Ducklings

| Compound | Age of Ducks (days) | Administration | Duck # 1 | 2 | 3 | 4 | (5) | (6) |
|---|---|---|---|---|---|---|---|---|
| Example 11 | 6 |  | 187 | 143 | 520 | 288 | 518 | 206 |
|  | 7 |  | 156 | 111 | 311 | 215 | 513 | 200 |
|  | 8 |  | 168 | 121 | 277 | 256 | 228 | 103 |
|  | 9 |  | 233 | 102 | 412 | 311 | 300 | 147 |
|  | 10 | * | 213 | 120 | 377 | 333 | 310 | 155 |
|  | 11 | * | 155 | 61 | 130 | 132 | 304 | 69 |
|  | 12 | * | 64 | 27 | 77 | 21 | 119 | 35 |
|  | 13 | * | 11 | 2 | 16 | 2 | 85 | 43 |
|  | 14 | * | 6 | 1 | 2 | 1 | 62 | 27 |
|  | 15 | * | <1 | <1 | 2 | 1 | 48 | 39 |
|  | 16 | * | <1 | <1 | <1 | 1 | 24 | 48 |
|  | 17 | * | <1 | <1 | <1 | <1 | 107 | 16 |
|  | 18 |  | <1 | <1 | <1 | <1 | 146 | 21 |
|  | 19 |  | <1 | <1 |  | <1 | 155 | 12 |

TABLE 6-continued

Antiviral Efficacy of Compounds of Formula I Against Hepatitis B Virus in Ducklings

| Compound | Age of Ducks (days) | Administration | Serum DHBV DNA (ng/ml) Duck # | | | | | |
|---|---|---|---|---|---|---|---|---|
| | | | 1 | 2 | 3 | 4 | (5) | (6) |
| | 20 | | <1 | <1 | | <1 | 190 | 62 |
| | 21 | | <1 | <1 | | <1 | 221 | 190 |
| | 22 | | 3 | <1 | | <1 | 297 | 196 |
| | 23 | | 12 | <1 | | <1 | 266 | 200 |
| | 24 | | 16 | <1 | | <1 | 175 | 182 |
| | 25 | | 31 | 2 | | <1 | 192 | 323 |
| | 26 | | 71 | 2 | | | 283 | 340 |
| | 27 | | 134 | 7 | | | 357 | 263 |

Remark: ducks 3 and 4 died on day 18 and day 26, respectively. Ducks (5) and (6) are the saline treated, placebo controls.

The results indicate that the compound is active against hepatitis B virus in vivo.

TABLE 7

Antiviral Activity of Compounds of Formula I Against Epstein-Barr Virus In Vitro

| Compound | concentration (uM) | EBV genome copies/cell |
|---|---|---|
| Example 11 | 0.01 | 223 |
| | 0.10 | 181 |
| | 1.00 | 40 |
| | 5.00 | 12 |
| | 10.00 | 10 |
| | 50.00 | ** |
| control | | 214 |

**This drug concentration was toxic.

The results indicate that the compound is active against Epstein-Barr virus.

TABLE 8

Antiviral Activity of Compounds of Formula I Against Varicella-Zoster Virus Plaque Formation in Human Foreskin Monolayer Cultures

| Compound | Concentration ug/ml | Plaque Reduction % | MTT Assay (% of control) | $MIC_{50}$ ug/ml |
|---|---|---|---|---|
| 11 | 100 | 100 | 62 | 1.4 |
| | 32 | 100 | 72 | |
| | 10 | 100 | 76 | |
| | 3.2 | 97.7 | 79 | |
| | 1.0 | 47.1 | — | |
| | 0.32 | 18.0 | — | |
| | 0.1 | 11.5 | — | |

Average number of plaques in untreated virus control cultures = 87

The results indicate that the compound is active against Varicella-Zoster virus.

TABLE 9

Antitumor Activity of Compounds of Formula I Against Cultured Tumor Cells

| Cell Line: Compound | A549 IC50 (ug/ml) | HCT-8 IC50 (ug/ml) | P388-D1 IC50 (ug/ml) |
|---|---|---|---|
| 4C | 49.1 | 71.4 | 0.64 |
| 11 | 94.6 | >100 | 2.8 |
| 67B | 18.8 | 0.63 | 4.9 |
| 67F | 3.1 | 5.9 | 5.2 |
| 67C | 18.4 | 4.3 | 16.4 |

IC50: The concentration of test compound needed to reduce the absorbance at 570 nm in a colorimetric assay by 50%
A549: Lung carcinoma, Human (acquired from ATCC, Catalog #CCL 185)
HCT-8: Adenocarcinoma, ileocecal, Human (acquired from ATCC, Catalog #CCL 244)
P388-D1: (Mouse, Lymphocytic Leukemia) (acquired from ATCC, Catalog #CCL 46)

The results indicate that the compounds are active against the indicated tumors.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate. heptonate, hexanoate, fumarate, hydrochloride, hydrobromide, hydroiodide, 2-hydroxy ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The novel compounds of the present invention possess antiviral activity and are useful for treating or preventing virus related diseases. Compounds of the invention are effective against herpes simplex viruses, human cytomegalovirus, hepatitis B virus, Epstein-Barr virus and Varicella Zoster virus.

Total daily dose administered to a host in single or divided doses may be in amounts, for example, from 0.1 to 2000 mg/kg body weight daily and more usually 1.0 to 500 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of ointments, creams or ophthalmically acceptable solutions, suspensions, emulsions, ointments and solid inserts. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents. emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

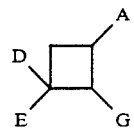

wherein A is

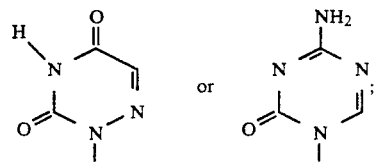

E is hydrogen, —$CH_2OH$ or —OH; and

G and D are independently selected from hydrogen, $C_1$ to $C_{10}$ alkyl, —OH, —$CH_2OH$, —$CH_2OR_{20}$ wherein $R_{20}$ is $C_1$ to $C_6$ alkyl, —$CH_2OC(O)R_{21}$ wherein $R_{21}$ is $C_1$ to $C_{10}$ alkyl, —$CH_2OC(O)CH(R_{22})(NHR_{23})$ wherein $R_{22}$ is the side chain of any of the naturally occuring amino acids and $R_{23}$ is hydrogen or —$C(O)CH(R_{24})(NHR_2)$ wherein $R_{24}$ is the side chain of any of the naturally occuring amino acids, —$CH_2SH$, —$CH_2Cl$, $CH_2F$, —$CH_2Br$, —$CH_2I$, —$C(O)H$, —$CH_2CN$, —$CH_2N_3$, —$CH_2NR_1R_2$, —$CO_2R_1$, —$CH_2CH_2OH$, —$CH_2CH_2OR_{20}$ wherein $R_{20}$ is as defined above, —$CH_2CH_2OC(O)R_{21}$ wherein $R_{21}$ is as defined above, —$CH_2CH_2OC(O)CH(R_{22})(NHR_{23})$ wherein $R_{22}$ and $R_{23}$ are as defined above, —$CH_2CH_2PO_3H_2$, —$CH_2OPO_3H_2$, —$OCH_2PO_3H_2$ and —$CH_2CO_2R_3$ wherein $R_1$ and $R_2$ are independently selected from hydrogen and $C_1$ to $C_{10}$ alkyl, —$NHC(O)R_3$ wherein $R_3$ is hydrogen, $C_1$ to $C_{10}$ alkyl, carboxyalkyl or aminoalkyl, —$N=CHNR_4R_5$ wherein $R_4$ and $R_5$ are independently selected from $C_1$ to $C_{10}$ alkyl, —$N(R_6)OR_7$ wherein $R_6$ and $R_7$ are independently selected from hydrogen and $C_1$ to $C_{10}$ alkyl, and —$N(R_8)NR_9R_{10}$ wherein $R_8$, $R_9$ and $R_{10}$ are independently selected from hydrogen and $C_1$ to $C_{10}$ alkyl, with the provide that when E is —OH then D is not —OH and with the proviso that when E is hydrogen and D is hydrogen or $C_1$ to $C_{10}$ alkyl then G is not hydrogen or $C_1$ to $C_{10}$ alkyl; or a pharmaceutically acceptable salt thereof.

2. A compound of the formula:

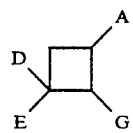

wherein A is

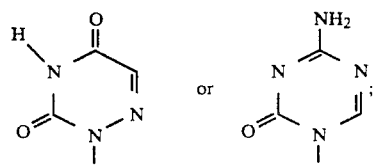

E is hydrogen, —CH₂OH or —OH; and G and D are independently selected from hydrogen, C₁ to C₁₀ alkyl, —OH, —CH₂OH, —CH₂OR₂₀ wherein R₂₀ is C₁ to C₆ alkyl, —CH₂OC(O)R₂₁ wherein R₂₁ is C₁ to C₁₀ alkyl, —CH₂OC(O)CH(R₂₂) (NHR₂₃) wherein R₂₂ is the side chain of any of the naturally occuring amino acids and R₂₃ is hydrogen or —C(O)CH(R₂₄) (NH₂) wherein R₂₄ is the side chain of any of the naturally occuring amino acids, —CH₂SH, —CH₂Cl, —CH₂F, —CH₂Br, —CH₂I, —C(O)H, —CH₂CN, —CH₂N₃, —CH₂NR₁R₂, —CO₂R₁, —CH₂CH₂OH, —CH₂CH₂OR₂₀ wherein R₂₀ is as defined above, —CH₂CH₂OC(O)R₂₁ wherein R₂₁ is as defined above, —CH₂CH₂OC(O)CH(R₂₂) (NHR₂₃) wherein R₂₂ and R₂₃ are as defined above, —CH₂CH₂PO₃H₂, —CH₂OPO₃H₂, —OCH₂PO₃H₂ and —CH₂CO₂R₃ wherein R₁ and R₂ are independently selected from hydrogen and C₁ to C₁₀ alkyl, —NHC(O)R₃ wherein R₃ is hydrogen, C₁ to C₁₀ alkyl, carboxyalkyl or aminoalkyl, —N=CHNR₄R₅ wherein R₄ and R₅ are independently selected from C₁ to C₁₀ alkyl, —N(R₆)OR₇ wherein R₆ and R₇ are independently selected from hydrogen and C₁ to C₁₀ alkyl, and —N(R₈)NR₉R₁₀ wherein R₈, R₉ and R₁₀ are independently selected from hydrogen and C₁ to C₁₀ alkyl, with the proviso that when E is —OH then D is not —OH and with the proviso that when E is hydrogen and D is hydrogen or C₁ to C₁₀ alkyl then G is not hydrogen or C₁ to C₁₀ alkyl; and with the proviso that when E is hydrogen and G is —OH, then D is other that —CH₂OH, —CH₂OC(O)R₂₁ or —CH₂OPO₃H₂ or a pharmaceutically acceptable salt thereof.

3. A compound of the formula

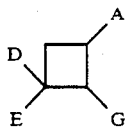

wherein A is

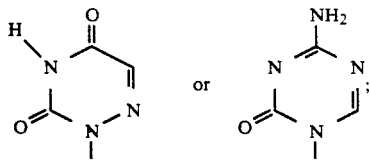

E is hydrogen; and G is —OH and D is —CH₂OH, —CH₂OC(O)R₂₁ wherein R₂₁ is C₁ to C₁₀ alkyl or —CH₂OPO₃H₂; or a pharmaceutically acceptable salt thereof.

4. A compound of the formula

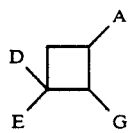

wherein A is

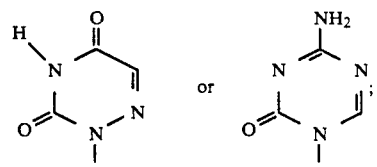

E is hydrogen, —CH₂OH or —OH; and G and D are independently selected from hydrogen, C₁ to C₁₀ alkyl, —OH, —CH₂OH, —CH₂OR₂₀ wherein R₂₀ is C₁ to C₆ alkyl, —CH₂OC(O)R₂₁ wherein R₂₁ is C₁ to C₁₀ alkyl, —CH₂OC(O)CH(R₂₂)(NHR₂₃) wherein R₂₂ is the side chain of any of the naturally occuring amino acids and R₂₃ is hydrogen or —C(O)CH(R₂₄) (NH₂) wherein R₂₄ is the side chain of any of the naturally occuring amino acids. —CH₂SH, —CH₂Cl, —CH₂F, —CH₂Br, —CH₂I, —C(O)H, —CH₂CN, —CH₂N₃, —CH₂NR₁R₂, —CO₂R₁, —CH₂CH₂OH, —CH₂CH₂OR₂₀ wherein R₂₀ is as defined above. —CH₂CH₂OC(O)R₂₁ wherein R₂₁ is as defined above, —CH₂CH₂OC(O)CH(R₂₂) (NMR₂₃) wherein R₂₂ and R₂₃ are as defined above, —CH₂CH₂PO₃H₂, —CH₂OPO₃H₂, —OCH₂PO₃H₂ and —CH₂CO₂R₃ wherein R₁ and R₂ are independently selected from hydrogen and C₁ to C₁₀ alkyl, —NHC(O)R₃ wherein R₃ is hydrogen, C₁ to C₁₀ alkyl, carboxyalkyl or aminoalkyl, —N=CHNR₄R₅ wherein R₄ and R₅ are independently selected from C₁ to C₁₀ alkyl, —N(R₆)OR₇ wherein R₆ and R₇ are independently selected from hydrogen and C₁ to C₁₀ alkyl, and —N(R₈)NR₉R₁₀ wherein R₈, R₉ and R₁₀ are independently selected from hydrogen and C₁ to C₁₀ alkyl; with the proviso that when E is —OH then D is not —OH and with the proviso that when E is hydrogen and D is hydrogen or C₁ to C₁₀ alkyl then G is not hydrogen or C₁ to C₁₀ alkyl; and with the proviso that when E is hydrogen and D is —CH₂OH, —CH₂OPO₃H₂ or —CH₂OC(O)R₂₁ then G is other than —CH₂OH, —CH₂OPO₃H₂ or —CH₂OC(O)R₂₁ or when E is hydrogen and G is —CH₂OH, —CH₂OPO₃H₂ or —CH₂OC(O)R₂₁ then D is other that —CH₂OH, —CH₂OPO₃H₂ or —CH₂OC(O)R₂₁; or a pharmaceutically acceptable salt thereof.

5. A compound of the formula:

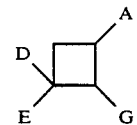

wherein A is

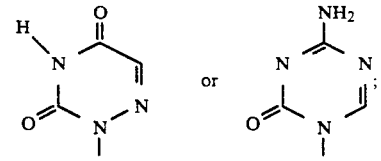

E is hydrogen; and
G and D are independently selected from —CH₂OH, —CH₂OPO₃H₂ and —CH₂OC(O)R₂₁ wherein R₂₁ is C₁ to C₁₀ alkyl; or a pharmaceutically acceptable salt thereof.

6. An antiviral pharmaceutical composition comprising a pharmaceutical carrier and a pharmaceutically effective amount of a compound of claim 1.

* * * * *